US008119672B2

(12) United States Patent
Rys et al.

(10) Patent No.: US 8,119,672 B2
(45) Date of Patent: Feb. 21, 2012

(54) COMPOUNDS, COMPOSITIONS AND METHODS FOR TREATING OR PREVENTING PNEUMOVIRUS INFECTION AND ASSOCIATED DISEASES

(75) Inventors: David J. Rys, Phialdelphia, PA (US); Theodore J. Nitz, Pottstown, PA (US); Janet A Gaboury, Blue Bell, PA (US); Christopher J. Burns, Malvern, PA (US); Daniel C. Pevear, Harleysville, PA (US); Thomas A. Lessen, Langhorne, PA (US); Torsten Herbertz, Honey Brook, PA (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 392 days.

(21) Appl. No.: 10/524,313

(22) PCT Filed: Aug. 11, 2003

(86) PCT No.: PCT/US03/25166
§ 371 (c)(1),
(2), (4) Date: Jul. 15, 2005

(87) PCT Pub. No.: WO2004/014317
PCT Pub. Date: Feb. 19, 2004

(65) Prior Publication Data
US 2005/0288345 A1 Dec. 29, 2005

Related U.S. Application Data

(60) Provisional application No. 60/402,402, filed on Aug. 9, 2002.

(51) Int. Cl.
*A61K 31/41* (2006.01)
*C07D 43/02* (2006.01)
(52) U.S. Cl. .......................................... 514/381; 548/282
(58) Field of Classification Search .................. 514/381; 548/252
See application file for complete search history.

(56) References Cited

U.S. PATENT DOCUMENTS

| | | | |
|---|---|---|---|
| 3,954,398 A | 5/1976 | Ramanathan | .................... 8/41 |
| 4,308,382 A | 12/1981 | Zenith | |
| 4,324,794 A | 4/1982 | Tidwell et al. | |
| 4,943,574 A | 7/1990 | Raeymaekers et al. | |
| 5,098,920 A | 3/1992 | Reitz | |
| 5,227,429 A | 7/1993 | Kawamura | .................... 525/92 |
| 5,773,646 A | 6/1998 | Chandrakumar et al. | |
| 6,495,580 B1 | 12/2002 | Nitz et al. | |
| 2005/0288344 A1 | 12/2005 | Nitz et al. | |

FOREIGN PATENT DOCUMENTS

| | | | |
|---|---|---|---|
| EP | 0 795 549 | | 9/1997 |
| GB | 1 508 391 | | 4/1978 |
| JP | 60-237047 | | 11/1985 |
| WO | WO95/00131 | | 1/1995 |
| WO | 97/05125 | | 2/1997 |
| WO | WO97/05125 | | 2/1997 |
| WO | WO 9938508 | * | 8/1999 |
| WO | WO01/00611 | | 1/2001 |
| WO | WO01/00612 | | 1/2001 |
| WO | WO01/00615 | | 1/2001 |
| WO | 02/059132 | | 8/2002 |

OTHER PUBLICATIONS

Avis, Kenneth, 1999, Pharmaceutical Dosage Forms vol. 1: Parenteral Medications, Marrcel Dekker, 173-175.*
Cammarata, Journal of Medicinal Chemistry, 1972, 15(6), 573-577.*
Abstract/Poster presented by T.J. Nitz at $40^{th}$ Inter-science Conference on Antimicrobial Agents and Chemotherapy (Toronto, Ont.) on Sep. 16, 2000.
Schlegel, D.C. et al. "Bulky Amine Analogues of Ketoprofen: Potent Antiinflammatory Agents"; J. Med. Chem. 27: 1690-1701 (1984).
Baker, B.R. et al. "Irreversible Enzyme Inhibitors. 181. Inhibition of Brain Choline Acetyltransferase by Derivatives of 4-Stilbazole"; J. Med. Chem. 14(4): 315-322-(1971).
DeClercq, E. "Perspectives for the chemotherapy of respiratory Synctial virus (RSV) infections"; International Journal of Antimocrobial Agents 7: 193-202 (1996).
DeLuca et al. "Formations of Small Volume Parenterals" Pharmaceutical Dosage Forms vol. 1: Parenteral Medications, Marcell Dekker, 1992, pp. 173-175.
Canadian Examiner's Requisition, dated Jun. 17, 2010 (3 pages).

* cited by examiner

*Primary Examiner* — Sharmila G Landau
*Assistant Examiner* — Kyle Purdy
(74) *Attorney, Agent, or Firm* — Hayes Soloway P.C.

(57) ABSTRACT

Compounds, compositions and methods are provided for the prophylaxis and treatment of infections caused by viruses of the Pneumovirinae subfamily of Paramyxoviridae and diseases associated with such infections.

15 Claims, No Drawings

COMPOUNDS, COMPOSITIONS AND METHODS FOR TREATING OR PREVENTING PNEUMOVIRUS INFECTION AND ASSOCIATED DISEASES

This application is a 35 U.S.C. §371 application based on PCT/US03/25166, filed 11 Aug. 2003, which in turn claims the benefit of U.S. Provisional Application 60/402,402 filed 9 Aug. 2002. The entire disclosure of each of the above identified applications is incorporated by reference herein.

FIELD OF THE INVENTION

The present invention relates to compounds, compositions and methods for preventing and treating viral infections, and the diseases associated therewith, particularly those viral infections and associated diseases caused by pneumoviruses.

BACKGROUND OF THE INVENTION

The Pneumovirinae subfamily of the Paramyxoviridae family consists of pneumoviruses that cause significant disease in humans and a number of animal species including cattle, goats, sheep, mice and in avian species.

Human respiratory syncytial virus (RSV), the prototypic member of the pneumovirus group, is the major pediatric viral respiratory tract pathogen, causing pneumonia and bronchiolitis in infants and young children. RSV disease is seasonal, with outbreaks in the U.S. typically beginning in November and continuing through April. During these yearly epidemics, approximately 250,000 infants contract RSV pneumonia, and up to 35% are hospitalized. Of those hospitalized, mortality rates of up to 5% have been reported. Children with underlying conditions such as prematurity, congenital heart disease, bronchopulmonary dysplasia and various congenital or acquired immunodeficiency syndromes are at greatest risk of serious RSV morbidity and mortality. In adults, RSV usually causes upper respiratory tract manifestations but can also cause lower respiratory tract disease, especially in the elderly and in immunocompromised persons. Infection in elderly and immunocompromised persons can be associated with high death rates. Natural infection with RSV fails to provide full protective immunity. Consequently, RSV causes repeated symptomatic infections throughout life.

The pneumoviruses of animals and avian species are similar to the human virus antigenically, in polypeptide composition and in disease causation.

Attempts to develop vaccines for RSV are ongoing, but none have yet been demonstrated to be safe and efficacious. Vaccine development has been overshadowed by adverse reactions exhibited by the initial formalin-inactivated RSV vaccine introduced in the late 1960s. Immunized children showed an increased incidence of RSV lower respiratory tract disease and developed abnormally severe illnesses, including death.

Chemotherapy with ribavirin [1-beta-D-ribofuranosyl-1H-1,2,4-triazole-3-carboxamide], an antiviral nucleoside which is the only pharmaceutical approved by the U.S. Food and Drug Administration (FDA) for treatment of RSV disease, is considered only for certain RSV patients (for example, those at high risk for severe complications or who are seriously ill with this infection). However, its efficacy and value are controversial. Recent studies have reported a failure to demonstrate either clinical or economic benefit to patients of ribavirin treatment. Moreover, ribavirin has certain toxic side-effects and, in order to minimize these, must be administered by inhalation as an aerosol in an enclosed environment. However, drug delivery as an aerosol in general can be hampered by low solubility of the drug in the carrier solvent.

A human intravenous immune globulin (IVIG) preparation is licensed for prophylactic use in certain patients at high-risk for RSV disease. Administration of this drug requires intravenous infusion of a large volume over a 2 to 4 hour period in children who have limited venous access due to prior intensive therapy, as well as compromised cardiopulmonary function. Moreover, intravenous infusion necessitates monthly hospital visits during the RSV season, which in turn places children at risk of nosocomial infections.

Thus, a need exists for new anti-viral agents and treatments for RSV infection that overcome the shortcomings of existing pharmaceutical preparations.

International Patent Application No. PCT/US99/01985 (filed on Jan. 29, 1999, now published as WO 99/38508) discloses compounds, compositions, and methods for treating or preventing pneumovirus infections and associated diseases, and is hereby expressly incorporated-by-reference in its entirety. International Patent Application No. PCT/US02102338 (filed on Jan. 28, 2002, now published as WO 02/059132) discloses intermediate compounds useful for making antiviral compounds.

It has been surprisingly discovered that the compounds of the instant invention have improved solubility characteristics which are useful for treating and preventing RSV disease.

SUMMARY OF THE INVENTION

The invention provides a compound of the formula:

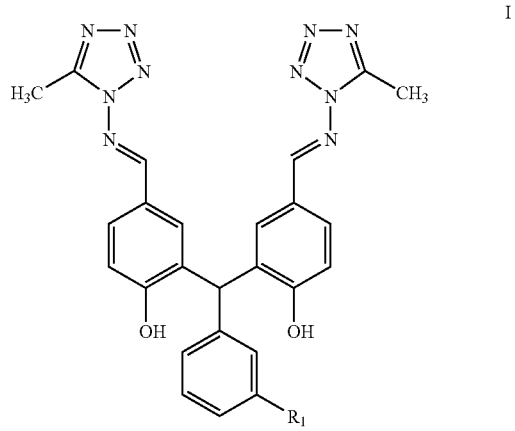

wherein:

$R_1$ represents a radical selected from the group consisting of alkoxy, alkoxyalkyl, halogen, nitro, carboxy, carboxyalkyl, carbalkoxy, carbalkoxyalkyl, carboxamide, carboxamidoalkyl, alkyl, cycloalkyl, alkylthio, alkylsulfinyl, alkylsulfonyl, sulfonamide, amidino, cyano, amino, amido, alkylamino, dialkylamino, alkylaminoalkyl, and alkoxy monosubstituted with a substituent selected from the group consisting of carboxy, amino, alkylamino and dialkylamino; and pharmaceutically acceptable salts of said compound.

The invention also relates to pharmaceutical compositions containing the antiviral compounds of Formula I and the corresponding methods of use for treating and preventing infections caused by viruses from the Pneumovirinae family, as well as the intermediate compounds and related methods of preparing the antiviral compounds described herein.

DETAILED DESCRIPTION OF THE INVENTION

In one aspect, the instant invention provides compounds of Formula I:

I wherein $R_1$ is as defined above.

A preferred aspect of the invention includes the compound of Formula I selected from the group consisting of:
2,2'-[(3-Propylphenyl)methylene]bis[4-[[(5-methyl-1H-tetrazol-1-yl)imino]methyl]]phenol,
2,2'-[[(3-Dimethylamino)phenyl]methylene]bis[4-[[(5-methyl-1H-tetrazol-1-yl)imino]methyl]]phenol,
2,2'-[[3-(Methylethyl)phenyl]methylene]bis[4-[[(5-methyl-1H-tetrazol-1-yl)imino]methyl]]phenol,
2,2'-[[(3-Methoxyethyl)phenyl]methylene]bis[4-[[(5-methyl-1H-tetrazol-1-yl)imino]methyl]phenol,
2,2'-[[[3-Ethyl(methylethyl)amino]phenyl]methylene]bis[4-[[(5-methyl-1H-tetrazol-1-yl)imino]methyl]]phenol, and
2,2'-[[(3-Diethylamino)phenyl]methylene]bis[4[[(5-methyl-1H-tetrazol-1-yl)imino]methyl]]phenol.

The compound of Formula I is useful for treating and preventing RSV disease and has improved solubility in pharmaceutical formulations. In particular, the compounds of Formula I have improved solubility in ethanolic solvents (see Table 2). The indicated improved solubility characteristics facilitate the preparation of pharmaceutical formulations and the delivery of the pharmaceutical formulations to a patient's pulmonary system using electrohydrodynamic (EHD) technology. Electrohydrodynamic spraying is a known process whereby solutions are aerosolized using electrical forces. In an EHD spray nozzle, the fluid to be aerosolized flows over a region of high electric field strength and receives a net electrical charge that remains on the surface of the fluid. As the solution exits the nozzle, the repelling force of the surface charge generates a thin jet of fluid. The jet breaks up into droplets of uniform size that collectively form a cloud. The result is an aerosolized solution having a monodispersed particle size distribution and near zero velocity. The improved solubility of the compound of Formula I in the formulations used in an EHD device facilitates the delivery of higher concentrations of the desired compound to the patient pulmonary tissue with fewer numbers of actuations of the EHD device. One of ordinary skill in the art may practice the instant invention with EHD devises that are commercially available or otherwise with known EHD technology.

In accordance with another aspect, the present invention provides a class of novel intermediates that are useful in preparing the anti-viral agents described herein. These intermediates have the general formula:

II wherein:
$R_2$ represents a radical selected from the group consisting of alkoxy, alkoxyalkyl, halogen, nitro, carboxy, carboxyalkyl, carbalkoxy, carbalkoxyalkyl, carboxamide, carboxamidoalkyl, alkyl, cycloalkyl, alkylthio, alkylsulfinyl, alkylsulfonyl, sulfonamide, amidino, cyano, amino, amido, alkylamino, dialkylamino, alkylaminoalkyl, and alkoxy monosubstituted with a substituent selected from the group consisting of carboxy, amino, alkylamino and dialkylamino; and pharmaceutically acceptable salts of said compound.

In accordance with another aspect, the present invention provides a class of novel intermediates that are useful in preparing the anti-viral agents described herein. These intermediates have the general formula:

III wherein $R_b$ is selected from the group consisting of $-CH_2OCH_3$, $-CH_2OCH_2CH_3$, $-CH(CH_3)OCH_2CH_3$, $-CH_2-OCH_2CH_2-OCH_3$, $-CH_2-OCH_2CH_2-Si(CH_3)_3$, $-CH_3$, $-CH_2C_6H_5$, $-(CH_2)_2Si(CH_3)_3$, $-CON(R_cR_d)_2$, $-CSN(RR)_2$, and $-PO(NR_cR_d)_2$;

$R_c$ and $R_d$ are independently selected from an alkyl group;
$R_3$ represents a radical selected from the group consisting of alkoxy, alkoxyalkyl, halogen, carboxyalkyl, carbalkoxy, carbalkoxyalkyl, carboxamide, carboxamidoalkyl, alkyl, cycloalkyl, alkylthio, alkylsulfinyl, alkylsulfonyl, sulfonamide, amidino, cyano, amino, amido, alkylamino, dialkylamino, alkylaminoalkyl, and alkoxy monosubstituted with a substituent selected from the group consisting of carboxy, dialkylamino and

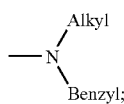

and P is a protected formaldehyde group such as:

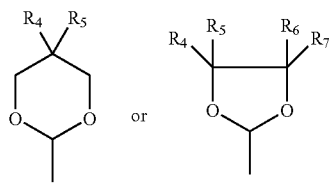

wherein $R_4$, $R_5$, $R_6$ and $R_7$ are independently selected from the group consisting of hydrogen and alkyl; and pharmaceutically acceptable salts of said compound.

The present invention also provides new synthetic methods useful for preparation of the compounds described herein.

One method comprises making the antiviral compounds of Formula I, from the compounds of Formula II, by reacting the aldehyde moieties in Formula II with 1-amino-5-methyltetrazole to produce the desired product as shown below:

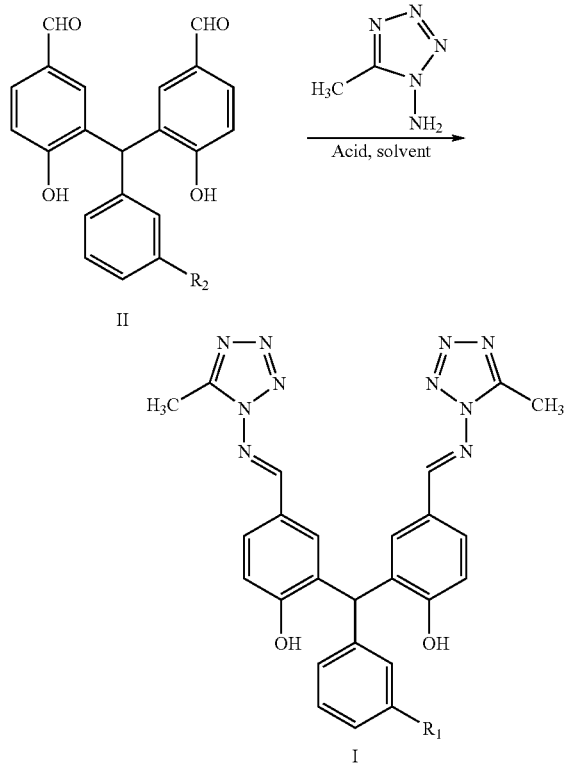

A method useful in the ultimate preparation of antiviral compounds involves deprotection and reduction of the $R_3$-substituted triphenylcarbinol derivative of Formula III with hydriodic acid and acetic acid, preferably at room temperature, to generate the aldehyde of Formula II as shown below:

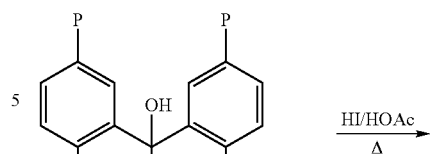

Another method useful in the ultimate preparation of antiviral compounds involves the preparation of the compound of the Formula III via the reaction shown below:

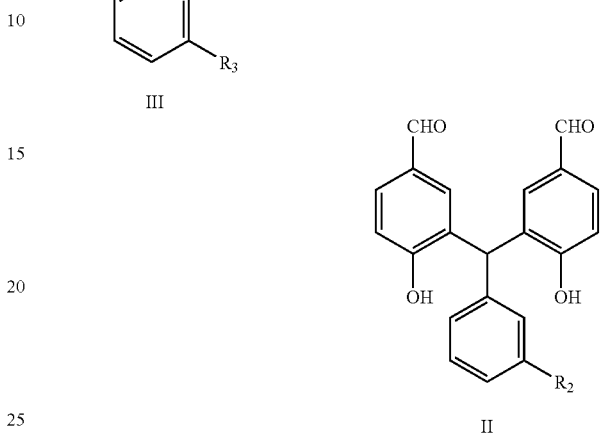

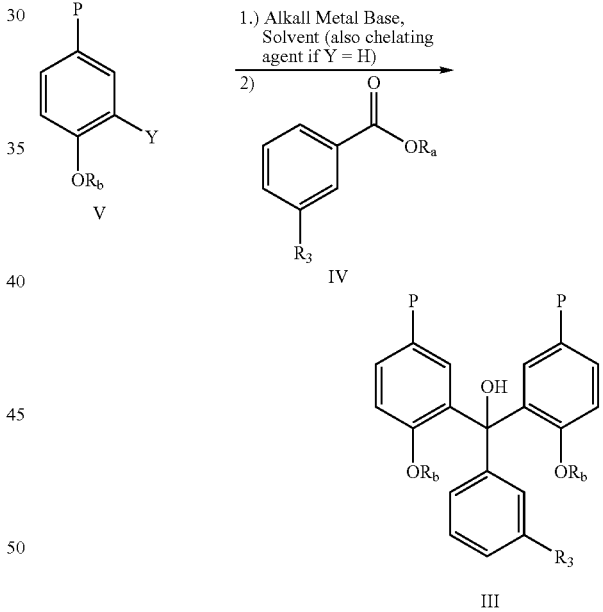

wherein Y is hydrogen, bromo or iodo and $R_b$ and P are as described above, and $R_a$ is a lower alkyl group According to still another aspect, the present invention provides pharmaceutical compositions comprising one or more of the above-described compounds in combination with a pharmaceutically acceptable carrier medium.

In accordance with a further aspect, the present invention provides a method for preventing and treating pneumovirus infection and for preventing and treating diseases associated with pneumovirus infection in living hosts, by administering to a living host susceptible to pneumovirus infection a therapeutically effective amount of a compound of the above structures and/or the isomers and pharmaceutically acceptable salts of said compounds, or pharmaceutical compositions containing same.

The starting materials for preparing the compounds of the invention are either commercially available or can be conveniently prepared according to one of the synthetic schemes and/or examples set forth below or otherwise using known chemistry procedures.

1) Preparation of the benzoate ester intermediate: The ester intermediates of Formula IV may be purchased from commercial sources or alternatively can be readily synthesized by standard procedures which are well known to those of ordinary skill in the art, or otherwise by following one of the general synthetic schemes shown below:

a) The compound of Formula IV(a), can be prepared via the reaction show below, wherein X is a bromo or iodo, $R_a$ is a lower alkyl group, and $R_3$ is alkyl or cycloalkyl. The reaction is conducted in the presence of a catalyst, such as 1,1'-bis(diphenylphosphino)ferrocene]dichloropalladium(II), complex with dichloromethane (1:1); in an inert solvent, such as tetrahydrofuran:

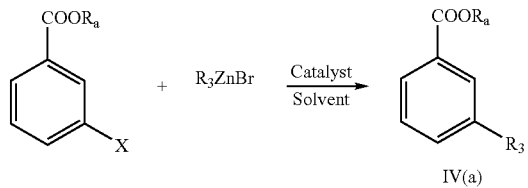

As an alternative, the compound of Formula IV(a) can be prepared by reacting the appropriate 3-bromobenzene wherein $R_3$ is alkoxy, alkoxyalkyl, carboxyalkyl, carbalkoxy, carbalkoxyalkyl, carboxamidoalkyl, alkyl, cycloalkyl, alkylthio, alkylsulfinyl, alkylsulfonyl, dialkylamino, alkylaminoalkyl, or alkoxy monosubstituted with a substituent selected from the group consisting of alkylamino or dialkylamino; with magnesium, isopropylmagnesium bromide, or isopropylmagnesium chloride; in an inert solvent, such as tetrahydrofuran; followed by the addition of the appropriate dialkyl carbonate (see below):

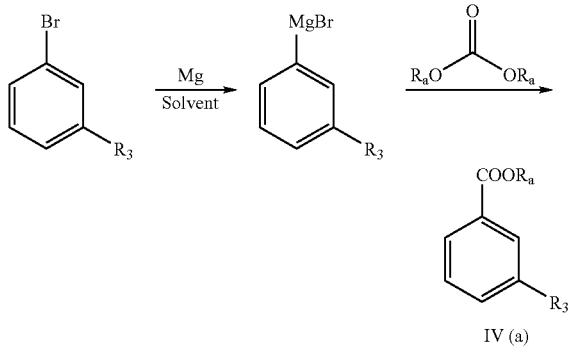

b) The compound of Formula IV(b) can be prepared according to the reaction shown below, wherein $R_z$ is the desired alkyl substituent, $R_a$ is as defined above, and X' is a bromo or iodo group. The reaction is conducted in an inert solvent, such as acetonitrile, toluene, or 1-methyl-3-pyrrolidinone; in the presence of a base, such as N,N-diisopropylethylamine:

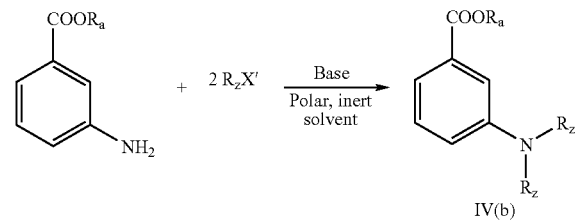

c) The compound of Formula IV(c) can be prepared according to the reaction shown below wherein $R_a$ is as defined above, and $R_y$ is an alkyl group or hydrogen and $R_z$ is an alkyl group. The reaction is conducted in the presence of sodium borohydride or sodium cyanoborohydride in an inert solvent, such as tetrahydrofuran (THF). A preferred method involves the addition of a small amount of water to solubilize the sodium borohydride and initiate the reaction:

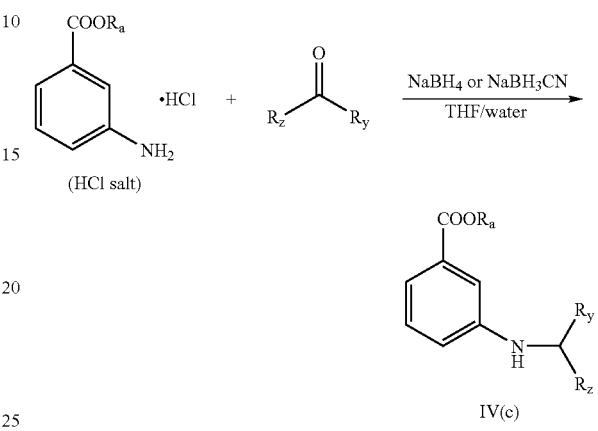

d) The compound of Formula IV(d) can be prepared according to the reaction shown below, wherein $R_a$ is as defined above and Alk is an alkyl group. The reaction is conducted with an alcohol (Alk-OH), such as ethanol or propanol; in the presence of Raney Nickel, and at elevated temperatures:

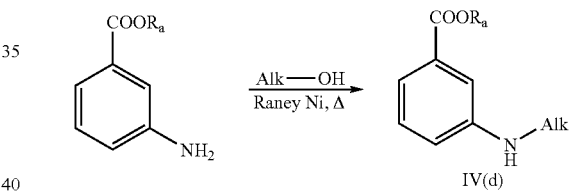

e) The compound of Formula IV(e) can be prepared according to the reaction shown below wherein $R_a$ is as defined above, Alk is an alkyl group, $R_z$ is the desired alkyl substituent, and X' is a bromo, iodo or sulfonate group; in an inert polar solvent, such as acetonitrile or 1-methyl-3-pyrrolidinone; in the presence of a base, such as N,N-diisopropylethylamine:

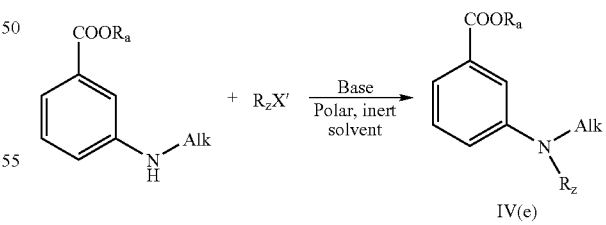

f) The compound of Formula IV(f) can be prepared according to the reaction shown below wherein $R_a$ is as defined above, BnCl is benzyl chloride (also benzyl bromide may be used). The reaction is conducted in the presence of a base, such as potassium carbonate (or sodium carbonate may be used), and in a polar solvent, such as ethanol; followed by a reaction with an alkylhalide, $R_zX'$, wherein $R_z$ is the desired alkyl substituent, and X' is a bromo or iodo group, in a polar inert solvent, such as ethanol:

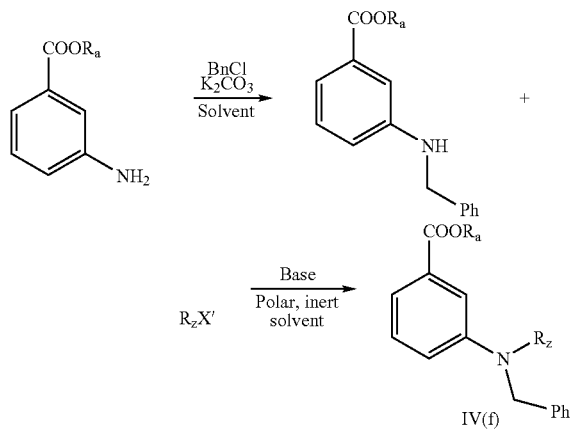

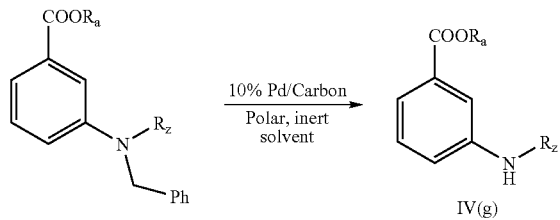

g) The compound of Formula IV(g) can be prepared according to the hydrogenation (deprotection) reaction shown below, where in $R_a$ is as defined above, and $R_z$ is the desired alkyl substituent. The reaction is conducted with 10% palladium on carbon in an alcoholic solvent, such as methanol or ethanol.

The hydrogenation (deprotection) reaction can be performed after the compound of Formula IV(f) is used to prepare a tri-aryl methanol intermediate of Formula III.

h) The compound of Formula IV(h) can be prepared according to the reaction shown below, by adding 3-chlorosulfonyl benzoic acid to a mixture of the indicated amine and an amine base, such as triethylamine; and in an inert solvent, for example, tetrahydrofuran; followed by dissolving the resulting sulfonamide benzoic acid in alcohol of the formula $R_a$ OH, wherein $R_a$ is as defined above, and $R_y$ and $R_z$ independently represent hydrogen or alkyl; preferably in the presence of a catalytic amount of thionyl chloride:

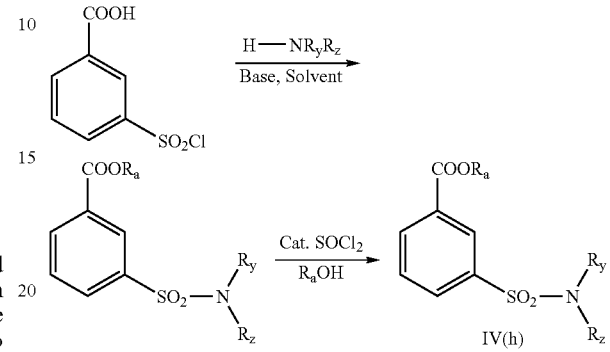

2) Preparation of di-protected compound of Formula V:

The compounds of Formula V can be prepared according to reaction schemes (a), (b) and (c) shown below. The order of the protection conditions for the preparation of the di-protected compound of Formula V may be reversed as shown in the reactions in (a) and (b) below, and the single-protected intermediates of Formula VII(a-d) prepared therein may be isolated and/or purified if desired prior to preparation of the compound of Formula V. The 3-substituted 4-hydroxybenzaldehyde of Formula III may be purchased from commercial sources or alternatively is readily synthesized by standard procedures which are well known to those of ordinary skill in the art.

(a) The compounds of Formula V can be prepared according to the reactions shown below.

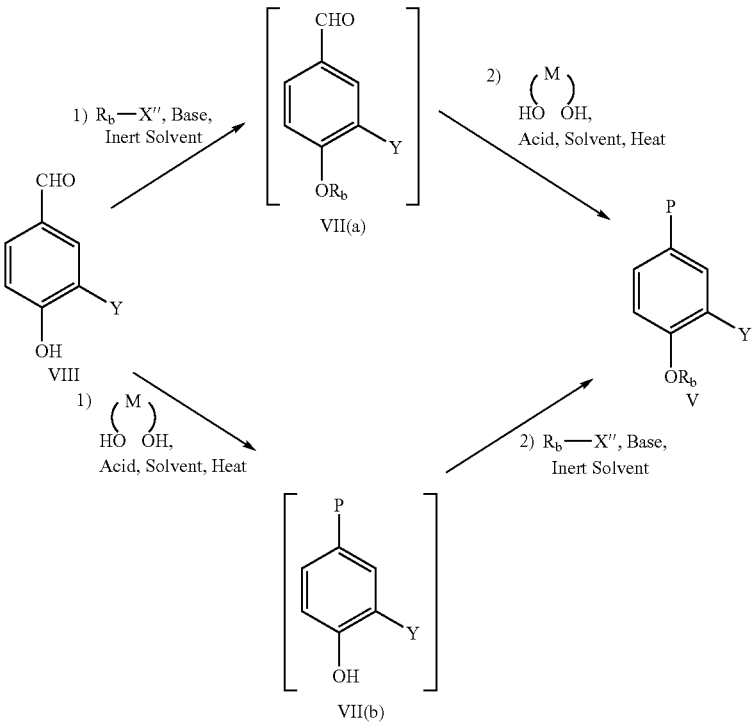

The intermediate compound of Formula VII(a), wherein Y is hydrogen, bromo or iodo, $R_b$ is —$CH_2OCH_3$, —$CH_2OCH_2CH_3$, —$CH_2$—$OCH_2CH_2$—$OCH_3$, —$CH_2$—$OCH_2CH_2$—$Si(CH_3)_3$, —$CH_3$, —$CH_2C_6H_5$, —$(CH_2)_2Si(CH_3)_3$, —$CON(R_cR_d)_2$, —$CSN(R_cR_d)_2$, wherein $R_c$ and $R_d$ and —$PO(NR_cR_d)_2$, wherein $R_c$ and $R_d$ are independently selected from an alkyl group, X" is a halogen such as chloro, bromo, or iodo, may be prepared according to the reaction shown above. The reaction is conducted in the presence of a base such as diisopropylethylamine, triethylamine, potassium carbonate, sodium hydride, or pyridine; in an inert solvent; and preferably at temperatures ranging from −20° C. to 100° C. Depending on the base, a preferable inert solvent may be one or more of the following: dichloromethane, tetrahydrofuran, 1-methyl-2-pyrrolidinone, dimethyl sulfoxide, acetone, or N,N-dimethylformamide.

The intermediate of Formula VII(a) may be used to prepare the compound of Formula V according the reaction shown above, wherein P is a protected formaldehyde group such as:

such as, pyridinium para-toluenesulfonate, pyridinium hydrochloride, p-toluenesulfonic acid monohydrate, 2,4,6-trimethylpyridinium p-toluenesulfonate, camphorsulfonic acid, or Amberlyst®-15; and in an inert solvent, such as benzene, toluene, cyclohexane or tetrahydrofuran, preferably with the azeotropic removal of water. The acid is preferably a mild acid and/or preferably used in a catalytic amount.

Alternatively, the intermediate compound of Formula VII (b), wherein Y, M and P are as previously defined may be prepared according to the reaction shown above. The intermediate of Formula VII(b) then may be used to prepare the compound of Formula V, wherein $R_b$ is defined above. The reaction conditions of the protection steps are analogous to those used for preparing compound VII(a) and preparing compound V therefrom.

(b) The compounds of Formula V also may be conveniently prepared according to the reactions below.

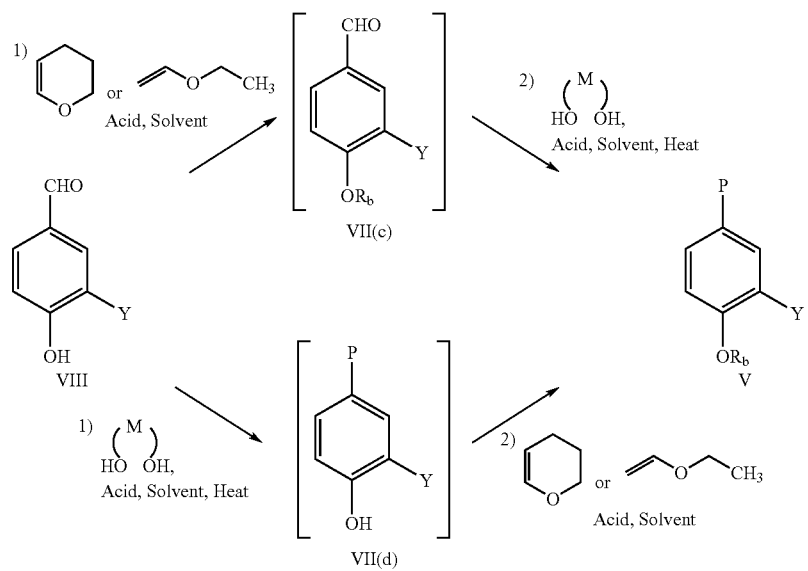

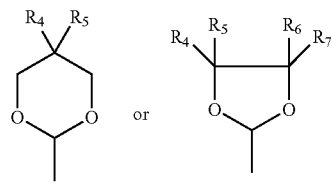

wherein $R_4$, $R_5$, $R_6$ and $R_7$ are independently selected from the group consisting of hydrogen or alkyl. The reaction is conducted by refluxing VII(a) with

where M is ($CH_2$—$CR_4R_5$—$CH_2$) or ($CR_4R_5$—$CR_6R_7$) and $R_4$, $R_5$, $R_6$ and $R_7$ are independently selected from the group consisting of hydrogen or alkyl; in the presence of an acid, The intermediate compound of Formula VII(c), wherein $R_b$ is

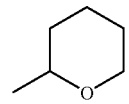

or —$CH(CH_3)OCH_2CH_3$, Y is hydrogen, bromo or iodo, and M and P are as defined above may be prepared according to the reaction shown above. The reaction is conducted in the presence of an acid catalyst, such as pyridinium para-toluenesulfonate, dry hydrochloric acid, pyridinium hydrochloride, camphorsulfonic acid, 2,4,6-trimethylpyridinium p-toluenesulfonate, Amberlyst®-15, or p-toluenesulfonic acid monohydrate; and in a non-polar inert solvent, such as dichloromethane, ethyl acetate, dimethoxyethane, p-dioxane, chloroform, dichloroethane, or tetrahydrofuran; at temperatures between −20° C. and 140° C., or otherwise above the freezing point and up to the reflux temperature of the solvent. The compound of Formula V then may be prepared by protecting the aldehyde group of Formula VII(c) as analogously described above in paragraph 2(a). Similarly the protection steps may be conducted in reverse order so as to make the compound of Formula V via the intermediate of Formula VII(d).

(c) The compound of Formula V, wherein $R_b$ is —$CH_2OCH_3$, also may be prepared according to the reaction shown below, by reacting the 3-substituted 4hydroxybenzaldehyde of Formula VIII, wherein Y is hydrogen, bromide, or iodide; with dimethoxymethane and $P_2O_5$, in an inert solvent such as dichloromethane, chloroform, toluene, and cyclohexane; preferably at room temperature, and preferably in the presence of diatomaceous earth (or Celite™). The aldehyde group of Formula VII(e) is protected as described in paragraph 2(a) above.

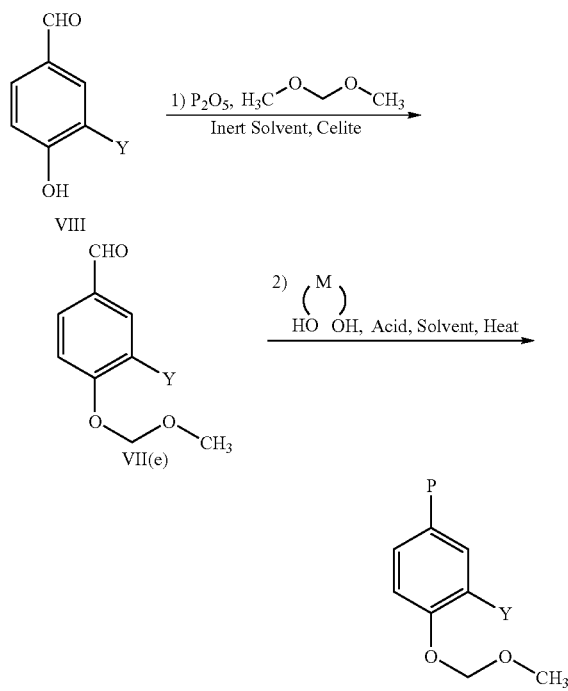

3) Preparation of the tri-aryl methanol compounds of Formula III:

(a) Direct Metalation:

The tri-aryl methanol of Formula III can be prepared by direct metalation of two equivalents of a di-protected benzaldehyde of Formula V(a) according to the reaction shown below:

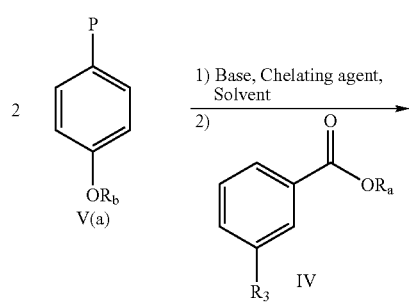

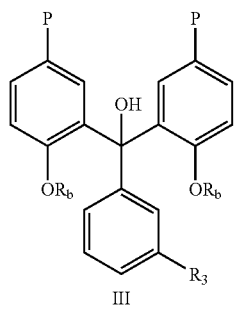

wherein $R_b$ is —$CH_2OCH_3$, —$CH_2OCH_2CH_2$, —$CH_2$—$OCH_2CH_2$—$OCH_3$, $CH_2$—$OCH_2CH_2$—$Si(CH_3)_3$, —$CH_3$, —$(CH_2)_2Si(CH_3)_3$, —$CON(R_cR_d)_2$, —$CSN(R_cR_d)_2$, —$PO(NR_cR_d)_2$,

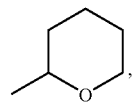

and —$CH(CH_3)OCH_2CH_3$, and P, $R_c$ and $R_d$ are as defined above. The compound of formula V(a) is treated first with an alkyl metal base, for example n-butyllithium, sec-butyllithium, t-butyllithium, or a metal amide base, for example, lithium diisopropylamide; and preferably in the presence of a chelating agent, such as, tetramethylethylenediamine (TMEDA) or hexamethylenephosphoramide (HMPA); then the appropriate benzoate ester of formula IV, where $R_a$ is an alkyl group and $R_3$ is selected as appropriate to obtain the desired product; is added to the reaction mixture to yield the tri-aryl methanol of Formula III. The reaction may be conducted preferably in the presence of an aprotic organic solvent, for example tetrahydrofuran, 2-methyltetrahydrofuran, diethylether, or t-butyl methyl ether; and preferably at reduced temperatures, for example between −78° C. and room temperature. It is also preferable to conduct the reaction under anhydrous or substantially anhydrous conditions.

(b) Metal Exchange (with a Halogen):

The tri-aryl methanol intermediate of Formula III can be prepared by halogen-metal exchange according to the reaction shown below:

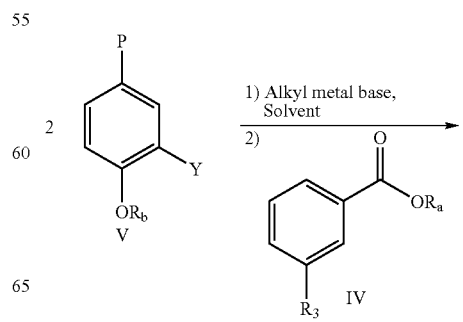

-continued

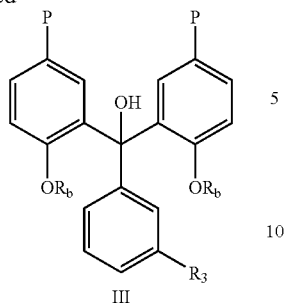
III where $R_b$ is —$CH_2OCH_3$, —$CH_2OCH_2CH_3$, —$CH(CH_3)$ $OCH_2CH_3$, —$CH_2$—$OCH_2CH_2$—$OCH_3$, —$CH_2$— $OCH_2CH_2$—$Si(CH_3)_3$, —$CH_3$, —$CH_2C_6H_5$, —$(CH_2)_2Si(CH_3)_3$, —$CON(R_cR_d)_2$, —$CSN(R_cR_d)_2$, or —$PO(NR_cR_d)_2$,

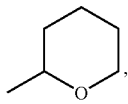

Y is bromo or iodo, and P is as defined above. Two equivalents of the compound of Formula V, wherein Y is as defined above, is treated with an alkyl metal base, for example n-butyllithium; followed by the reaction with approximately one equivalent of the desired compound of Formula IV, wherein $R_a$ is as defined above; to provide the corresponding tri-aryl methanol compound of Formula III. The reaction may be conducted preferably in the presence of an aprotic organic solvent, for example tetrahydrofuran, 2-methyltetrahydrofuran, diethylether, or t-butyl methyl ether; and preferably at reduced temperatures, for example between −78° C. and room temperature. It is also preferable to conduct the reaction under anhydrous or substantially anhydrous conditions.

(c) Reaction with di-aryl ketone:

The tri-aryl methanol intermediate of Formula III, wherein $R_b$ is —$CH_2OCH_3$, —$CH_2OCH_2CH_3$, —$CH(CH_3)$ $OCH_2CH_3$, —$CH_2$—$OCH_2CH_2$—$OCH_3$, —$CH_2$— $OCH_2CH_2$—$Si(CH_3)_3$, —$CH_3$, —$CH_2C_6H_5$, or —$(CH_2)_2Si(CH_3)_3$, or

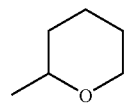

and $R_3$ is alkoxy, alkoxyalkyl, alkyl, cycloalkyl, dialkylamino, alkylthio, or alkoxy monosubstituted with dialkylamino, and P is as defined above; can also be prepared according to the reaction shown below by reacting a di-aryl ketone of Formula VI. First, the bromobenzene is treated with an alkyl metal base, for example n-butyllithium, in an inert organic solvent under anhydrous conditions; followed by reaction with the compound of Formula VI:

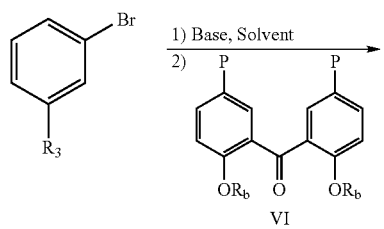

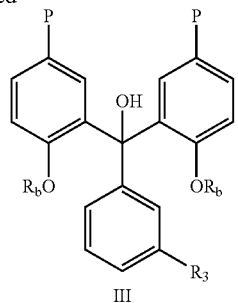
III

The diarylketone of Formula VI may be conveniently prepared according the reaction shown below:

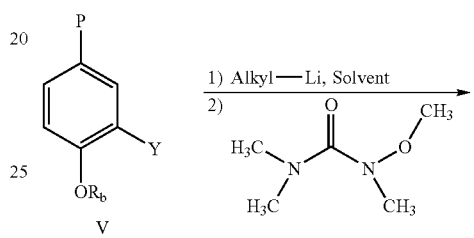

where P and $R_b$ are as defined above. First, the di-protected compound of Formula V, where Y is bromo or iodo, is treated with alkyl lithium base, for example n-butyllithium; in an inert organic solvent under anhydrous conditions, followed by reaction with N-methoxy-N,N',N'-trimethylurea so as to yield the compound of Formula VI.

The compounds of Formula III can be used as intermediates in accordance with the examples below, to form compounds of Formula II.

4) Preparation of Compounds of Formula I:

The compound of Formula I wherein $R_1$ is defined above, may be readily obtained by condensation of the aldehyde of Formula II, wherein $R_2$ is as defined above, with two equivalents of 1-amino-5-methyltetrazole, in the presence of an acid, such as p-toluenesulfonic acid monohydrate, methanesulfonic acid, benzenesulfonic acid, 2,4,6-trimethylpyridinium p-toluenesulfonate or pyridinium para-toluenesulfonate, at elevated temperatures, such as from room temperature to 90° C.; in a solvent such as an alcoholic solvent like ethanol, or in 1-methyl-2-pyrrolidinone, dimethyl sulfoxide, or N,N-dimethylformamide:

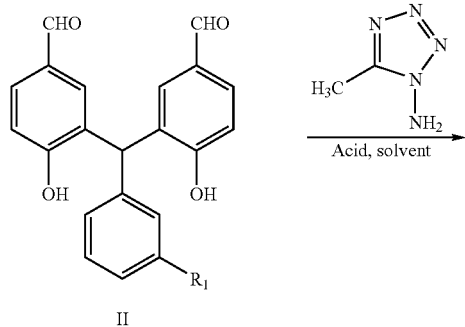

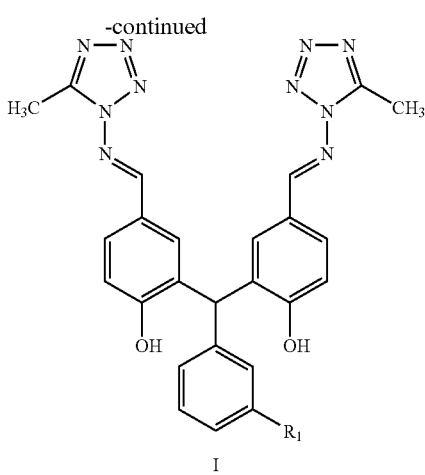

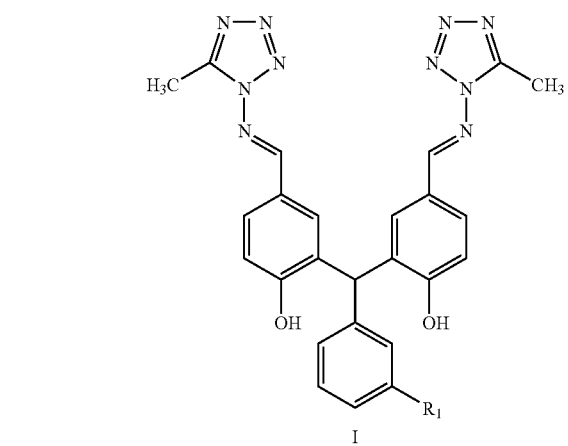

In the reaction shown above, the compound of Formula I where $R_1$ is a di-substituted amino may be isolated as a salt, for example, a tosic acid salt. The free-base compound is obtained under basic conditions, such as in the presence of sodium bicarbonate, by the reaction shown below:

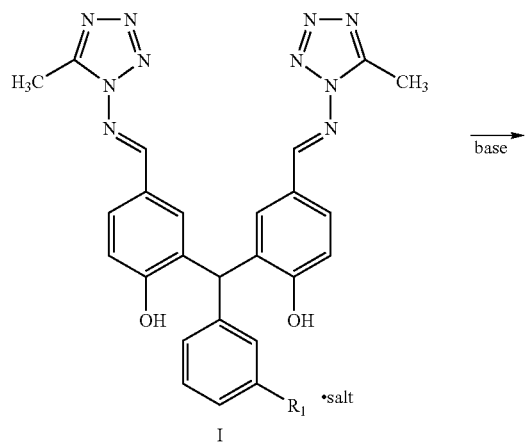

The term "alkyl," as used herein, refers to aliphatic hydrocarbon radicals of one to six carbon atoms in length, and may be straight or branched. Similarly, the term "alkyl," or any variation thereof, used in combination form to name substituents, such as alkoxy (—O-alkyl), alkylthio (—S-alkyl), alkylamino (—NH-alkyl), alkylsulfonyl (—S(O)$_2$-alkyl), carboxyalkyl (-alkyl-COOH), or the like, also refers to aliphatic hydrocarbon radicals of one to six carbon atoms in length, and preferably of one to four carbon atoms in length. Also "alk" in structural formula denotes an alkyl group, unless divalency is indicated in which case the "alk" denotes the corresponding alkylene group(s).

The term "lower alkyl" denotes a $C_1$-$C_4$ alkyl group.

The term "amido," as used herein, refers to a radical or substituent of the formula —NR"C(=O)R'", wherein R" and R'" represent hydrogen or alkyl.

The term "carboxamide," as used herein, refers to a radical or substituent of the formula —C(=O)—NR"R'", wherein R' and R'" are as previously defined.

The term "sulfonamide," as used herein, refers to a radical or substituent of the formula —SO$_2$NR'R'" or —NR"SO$_2$R'", wherein R' and R'" are as previously defined.

The term "carbalkoxy," as used herein, refers to a radical or substituent —C(=O)—OR", wherein R" is a previously defined.

The term "TBDMS" as used herein refers to a t-butyldimethylsilyl group.

The symbol "Δ" as used herein the schemes denotes heating to an elevated temperature.

The term "hexanes" as used herein refers to a solvent mixture of straight and branched chain hexane hydrocarbons, wherein the solvent mixture contains mostly n-hexane and some minor amounts of branched hexanes.

The abbreviation "Ph" when used herein the schemes and examples denotes a phenyl group.

The term "chloroform" as used herein denotes trichloromethane.

Percentage (%) of a solvent shown in the examples is by volume.

Preparation of specific embodiments of anti-pneumovirus compounds within the scope of the invention are exemplified below.

In vitro studies have been performed demonstrating the usefulness of compounds described herein as antiviral agents against pneumoviruses. Antiviral activity was measured on the basis of activity against RSV in a cell culture assay.

All possible isomers of the compounds described herein are within the scope of the present invention. Representative examples of such isomers include, without limitation, cis and trans isomers.

The compounds described herein, their isomers and pharmaceutically acceptable salts exhibit antiviral activity against pneumoviruses and are within the scope of the present invention.

The compounds of the invention can form useful salts with inorganic and organic acids, including, for example, hydrochloric acid, hydrobromic acid, methanesulfonic acid salts, or the like, as well as with inorganic bases, such as sodium or potassium salts.

The pharmaceutically acceptable salts of the compounds of the invention are prepared following procedures which are familiar to those skilled in the art.

The antiviral pharmaceutical compositions of the present invention comprise one or more of the above-described compounds or precursors thereof, as the primary active ingredient in combination with a pharmaceutically acceptable carrier medium and, optionally one or more supplemental active agents.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences*, Twentieth Edition, A. R. Gennaro (William and Wilkins, Baltimore, Md., 2000) discloses various carriers used in formulating pharmaceutical compositions and known techniques for the preparation thereof. Except insofar as any conventional carrier medium is incompatible with the antiviral compounds of the invention, such as by producing any undesirable biological effect or otherwise interacting in a deleterious manner with any other component(s) of the pharmaceutical composition, its use is contemplated to be within the scope of this invention.

The compounds of the invention, any precursors thereof and their isomers and pharmaceutically acceptable salts are also useful in treating and preventing pneumovirus infections and diseases when used in combination with supplemental active agents, which may be optionally incorporated into the pharmaceutical composition of the invention, or otherwise administered during a course of therapy. These include, without limitation, interferons, ribavirin, and immunomodulators, immunoglobulins, anti-flammatory agents, antibiotics, antivirals, anti-infectives, and the like, the combination of which with one or more compounds of the invention offers additive or synergistic therapeutic benefit.

In the pharmaceutical compositions of the invention, the active agent may be present in any therapeutically effective amount, which is typically at least 0.1% and generally not more than 90% by weight, based on the total weight of the composition, including carrier medium and/or supplemental active agent(s), if any. Preferably, the proportion of active agent varies between 1-50% by weight of the composition.

Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known carriers or excipients for medicaments may all be suitable as carrier media Compounds of the invention are useful in treating and preventing pneumovirus infections (and diseases) in humans, as well as in livestock, and may be used to treat cattle, swine and sheep, or to treat avian species such as turkeys, or for other animals susceptible to pneumovirus infection. Thus, the term "patient" as used herein includes, without limitation, all of the foregoing.

Compounds described herein are also useful in preventing or resolving pneumoviral infections in cell cultures, tissue cultures and organ cultures, as well as other in vitro applications. For example, inclusion of compounds of the invention as a supplement in cell or tissue culture growth media and cell or tissue culture components will prevent pneumoviral infections of cultures not previously infected with pneumoviruses. Compounds described above may also be used to eliminate pneumoviruses from cultures or other materials infected or contaminated with pneumoviruses, after a suitable treatment period, under any number of treatment conditions as determined by the skilled artisan.

The compounds of the invention may be administered using any amount and any route of administration effective for attenuating infectivity of the pneumovirus. Thus, the expression "amount effective to attenuate infectivity of pneumovirus," as used herein, refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like.

The compounds of the invention may be administered as an inhaled aerosol. The aerosol may be prepared and administered using an electrohydrodynamic device PHD). Preferred pharmaceutical formulations of the compound of Formula I for use in an EHD device are ethanol solutions. A preferred feature of the invention is a pharmaceutical composition that contains at least 50% ethanol (by volume). Other preferred features of the invention include pharmaceutical compositions containing at least 60% ethanol, at least 70% ethanol, at least 80% ethanol or at least 90% ethanol (by volume). Other features of the invention include a pharmaceutical formulation comprising water and ethanol and a pharmaceutical formulation comprising propylene glycol and water. A preferred feature of the invention is a pharmaceutical composition comprising ethanol, propylene glycol, and water. Another preferred feature of the invention is a pharmaceutical formulation comprising at least 90% ethanol and less than 5% water (by volume). An ultimately preferred feature of the invention is the pharmaceutical composition comprising about 85% ethanol, about 10% propylene glycol, and about 5% water (by volume). NaCl (in the form of a standard saline solution) may be used to adjust the solution resistivity in an EHD device. Other acceptable excipients that may be used in pharmaceutical formulations of Formula I for use in an EHD device are glycerol, dextrose, and lecithin.

An example for preparing a pharmaceutical composition for use in an EHD device is as follows:

1. Dispense the quantities of Ethyl Alcohol, USP and Propylene Glycol, USP into a clean 1 L glass bottle.
2. Stir solution from Step 1 for 5 minutes.
3. Add quantity of compound of Formula I to solution from Step 2.
4. Stir solution from Step 3 for a minimum of 2 hours at a temperature ranging from room temperature to 60° C., preferably from 50-60° C., until complete dissolution of the compound.

5. Adjust resistivity of solution with 0.9% Sodium Chloride for Injection, USP.
6. Filter bulk solution using a 0.2μ filter.
7. Fill and seal the cartridges for use in the EHD device (target fill volume 3 mL±0.1 mL)
8. Visually inspect each cartridge.
9. Label each cartridge.

The anti-pneumovirus compounds are preferably formulated in dosage unit form for ease of administration and uniformity of dosage. Dosage unit form as used herein refers to a physically discrete unit of antiviral agent appropriate for the patient to be treated. Each dosage should contain the quantity of active material calculated to produce the desired therapeutic effect either as such, or in association with the selected pharmaceutical carrier medium. Typically, the antiviral compounds of the invention will be administered in dosage units containing from about 0.1 μg to about 50 mg of the antiviral agent, with a range of about 0.001 mg to about 25 mg being preferred.

The compounds of the invention, including their isomers and pharmaceutically acceptable salts, may be administered as such, or in the form of a precursor from which the active agent can be derived, such as a prodrug. A prodrug is a derivative of a compound described herein, the pharmacologic action of which results from the conversion by chemical or metabolic processes in vivo. Prodrugs of the compounds of the invention may include, but are not limited to mono-, di- or tri-esters of simple or functionalized aliphatic carboxylic acids; esters of carbamic acids ($R_e$—(O—CO—$NR_fR_g)_n$); esters of amino acids ($R_c$—(O—CO—CH($NH_2$)$R_f)_n$); esters of unsubstituted or substituted aromatic acids ($R_e$—(O—CO-aryl$)_n$), wherein the aryl ring may be substituted with hydroxy, carboxy, alkyl, alkylthio, alkylsulphinyl, alkylsulphonyl, phosphoric acid, amino, alkylamido and halogen groups; esters of derivatized phosphoric acids; (acyloxy)methyl or acyloxy(ethyl)ethers ($R_e$—(O—$CH_2$—O—CO—$R_f)_n$ or $R_e$—(O—CH($CH_3$)—O—CO—$R_f)_n$); (alkoxycarbonyloxy)methyl or (alkoxycarbonyloxy)ethyl ethers ($R_e$—(O—$CH_2$—O—CO—O—$R_f)_n$); and O-glycosides, wherein $R_e$ is a residue of a compound of the invention, $R_f$ and $R_g$ are aliphatic radicals ($C_1$-$C_{10}$) and n is an integer from 1 to 3. Such prodrugs may be prepared according to procedures well known in the field of medicinal chemistry and pharmaceutical formulation science and are within the scope of the present invention.

The compounds of the invention may be administered orally, parenterally, such as by intramuscular injection, intraperitoneal injection, intravenous infusion or the like, or by inhalation, such as by aerosol, in the form of a solution or a dry powder, or the like, or by intubation, depending on the nature and severity of the infection being treated. The compounds of the invention may be administered orally, parenterally, or by inhalation or intubation at dosage levels of about $10^{-6}$ mg to about 1000 mg/kg, one or more times a day, to obtain the desired therapeutic effect.

The compounds of the invention will typically be administered from 1 to 4 times a day so as to deliver the above-mentioned daily dosage. However, the exact regimen for administration of the compounds and compositions described herein will necessarily be dependent on the needs of the individual host being treated, the type of treatment administered and the judgment of the attending physician, veterinarian or medical specialist.

In view of the inhibitory effect on pneumovirus replication in cell culture produced by the compounds used in the method of the invention, it is anticipated that these compounds will be useful not only for therapeutic treatment of pneumovirus infection, but for pneumovirus prophylaxis, as well. The dosages will be essentially the same, whether for treatment or prophylaxis of pneumovirus infection.

The following examples are provided to describe the invention in further detail. These examples, which set forth the preferred mode presently contemplated for carrying out the invention, are intended to illustrate and not to limit the invention.

Examples 1-30 illustrate the chemical synthesis of representative compounds of the invention.

Example 1

Preparation of 2,2'-[(3-Propylphenyl)methylene]bis[4-[[(5-methyl-1H-tetrazol-1-yl)imino]methyl]]phenol a. 4-Methoxymethoxybenzaldehyde. A solution of 4-hydroxybenzaldehyde (118.20 g, 0.968 mol) in dichloromethane (1.1 L) was stirred mechanically and cooled to 0° C., under argon. N,N-diisopropylethylamine (337.2 ml) was added to the reaction, and the mixture was stirred until homogenous. Chloromethyl methyl ether (101.30 g, 1.94 mol) was added dropwise, maintaining reaction temperature below 10° C. After the addition, the solution was warmed to room temperature, then stirred for 1 hour. The reaction was quenched with water (500 ml), and the aqueous phase was separated from the organic phase. The organic layer was washed with water, 5% glacial acetic acid, and saturated aqueous NaCl. The solution was dried with sodium sulfate, filtered, and rotary evaporated, yielding 170 g of the pure product.

b. 2-(4Methoxymethoxyphenyl)-5,5-dimethyl-1,3-dioxane. A solution of 4-methoxymethoxybenzaldehyde, neopentyl glycol (10.3 g, 98.9 mmol), pyridinium para-toluenesulfonate (1.0 g, 3.98 mmol), and benzene (500 ml) was refluxed with azeotropic removal of water for several hours, under argon. The cooled reaction mixture was quenched with 2 ml of triethylamine, and concentrated on rotary evaporator. The product was chromatographed (silica gel, 5% ethyl acetate in hexanes), yielding about 14.83 g of the product.

c. Preparation of:

1(c)

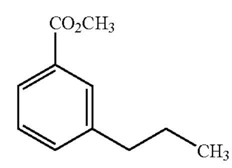

Pd catalyst ([1,1'-Bis(diphenylphosphino)ferrocene] dichloropalladium(II), complex with dichloromethane (1:1), 14.75 g, 58 mmol) and propyl zinc bromide (345 ml of 0.5M, 174 mmol) were added to a mixture of methyl 3-bromobenzoate (25.00 g, 116 mmol) in tetrahydrofuran (500 ml). The reaction was stirred at room temperature for 3 hours, and then quenched with a 20% aqueous $NH_4Cl$ solution. The organic solvents were removed in vacuo, and the remaining aqueous mixture was extracted with t-butyl methyl ether. The organic layer was washed with saturated aqueous NaCl, dried with magnesium sulfate, filtered through Celite, and concentrated on a rotary evaporator. The residue was chromatographed (silica gel, 2-5% ethyl acetate in hexanes), yielding 17.53 g of the desired product.

d. Preparation of:

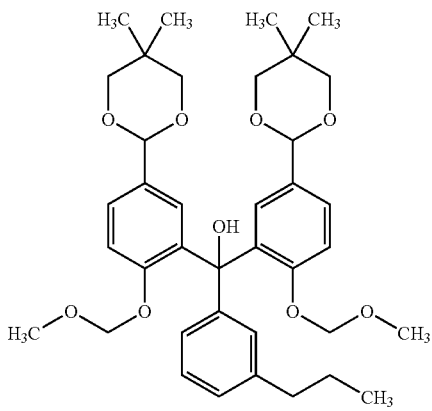

2-(4Methoxymethoxyphenyl)-5,5-dimethyl-1,3-dioxane (46.6 g, 185 mmol), prepared according to step b, above, was mixed with dry tetrahydrofuran (600 ml) in a 3-neck flask, under argon. N,N,N',N'-Tetramethylethylenediamine (27.9 ml, 185 mmol) was added to the solution, and the resulting mixture was cooled to around −5° C. in an ice/NaCl bath. Sec-butyllithium (156 ml, 1.3M in cyclohexane) was added via a syringe pump, maintaining the temperature of the reaction around 0° C. The reaction was stirred for 15 minutes, then a solution of compound 1(c) (10.97 g, 62 mmol) in dry tetrahydrofuran (250 ml) was added dropwise to the reaction. After this addition, the solution was stirred for 2 hours at 0° C. The reaction was then quenched with 20% aqueous $NH_4Cl$ (200 ml), and the organic solvents were removed in vacuo. An additional amount of 20% $NH_4Cl$ solution (200 ml) was added to the aqueous mixture, and then the mixture was extracted two times with ethyl acetate (400 ml). The organic layers were combined, washed with saturated aqueous NaCl, dried with magnesium sulfate, filtered, and concentrated on rotary evaporator. The crude product was chromatographed (silica gel, 15-20% ethyl acetate in hexanes), yielding 13.12 g of the desired product.

e. Preparation of:

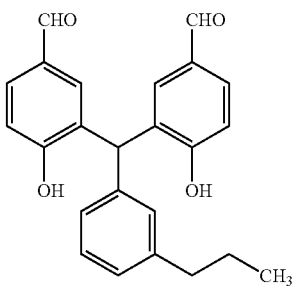

Hydriodic acid (18 ml, 58 wt % in water) was added to a solution of compound 1(d) (11.90 g, 18 mmol) in glacial acetic acid (180 ml). The reaction was stirred at room temperature for 2 hours. The reaction mixture was poured over ice and water, than extracted with ethyl acetate. The organic layer was washed with 10% aqueous $NaHSO_3$ (1 L) and saturated aqueous NaCl solution. The organics were dried over magnesium sulfate, filtered, and rotary evaporated. The resulting solid was purified with charcoal and recrystallized in ethyl acetate/hexanes, yielding 3.71 g of the desired product.

f. 2,2'-[(3-Propylphenyl)methylene]bis[4-[[(5-methyl-1H-tetrazol-1-yl)imino]methyl]]phenol. Compound 1(e) (2.80 g, 7.5 mmol) was dissolved in 75 ml absolute ethanol, and added dropwise to a refluxing solution of 1-amino-5-methyltetrazole (2.22 g, 22 mmol) and pyridinium para-toluenesulfonate (0.18 g, 0.94 mmol) in 75 ml ethanol, under argon. The reaction was heated to reflux for 2 hours, and then cooled to room temperature. A solid was collected by filtration and dried under vacuum, yielding about 4 g of crude product. The solid was recrystallized in hot ethanol and water. A precipitate was isolated by filtration and dried under vacuum to give 2.04 g of the title compound.

Example 2

Preparation of 2,2'-[[(3-Dimethylamino)phenyl]methylene]bis[4-[[(5-methyl-1H-tetrazol-1-yl)imino]methyl]]phenol The title compound was prepared essentially according to the basic procedure described in steps d-f Example 1, above; however, methyl 3-dimethylaminobenzoate was used in step d instead of compound 1(c).

Example 3

Preparation of 2,2'-[[3-(Methylethyl)phenyl]methylene]bis[4-[[(5-methyl-1H-tetrazol-1-yl)imino]methyl]]phenol a. Ethyl 3-isopropylbenzoate. Bromoisopropylbenzene (19.91 g, 0.1 mol) was slowly added to a suspension of magnesium (7.3 g, 0.3 mol) in dry tetrahydrofuran (150 ml), maintaining a mild reflux to form a Grignard reagent. The Grignard reagent was transferred to an addition funnel with a syringe, then added to a cooled solution (around 0° C. in a dry ice bath) of diethylcarbonate (36.35 ml, 0.3 mol) dissolved in tetrahydrofuran. The reaction was warmed to room temperature and stirred for 3 hours. The solution was then diluted with hexanes, and 1N hydrochloric acid was added. The organic layer was separated, washed with water (3×), brine, dried ($MgSO_4$), and concentrated on rotary evaporator. The product was purified via distillation.

b. 3-Bromo-4-hydroxybenzaldehyde. Bromine (319.64 g, 2.0 mol), diluted in dichloromethane, was added to a suspension of 4-hydroxybenzaldehyde in dichloromethane (1800 ml), over a period of 24 hours. The solids were filtered, washed with hexanes, and dried under vacuum. The isolated solid was suspended in hot water and filtered. This crude product was treated with charcoal in hot 3:1 water:methanol (~1500 ml), and a solid crystallized upon cooling providing 233.5 g of the desired product.

c. Preparation of:

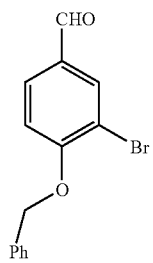

A suspension of 3-bromo-4-hydroxybenzaldehyde (95.5 g, 0.475 mol, which can be prepared according to step 3(b)) and milled potassium carbonate (138.2 g, 1 mol) in dimethyl sulfoxide was heated to 150° C. for 1 hour. The heat source was removed, and benzyl bromide (59.5 g, 0.5 mol) was added. The reaction mixture was stirred for an additional hour, than passed through a pad of silica gel. The solution was diluted with water and filtered. The solids were rinsed with water and air-dried. The crude product was recrystallized in ethanol, providing 120 g of the desired product.

d. Preparation of:

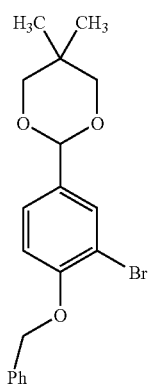

3(d)

A solution of compound 3(c) (60.06 g, 0.206 mol), neopentyl glycol (23.64 g, 0.227 mol), and pyridinium p-toluenesulfonate (catalytic) in benzene (350 ml) was refluxed with azeotropic removal of water for 15.5 hours. The mixture was cooled and partitioned between toluene and water. The organic layer was washed with water, dried (MgSO$_4$), and concentrated in vacuo. The crude product was recrystallized in methanol, providing 58.18 g of the desired product.

e. Preparation of:

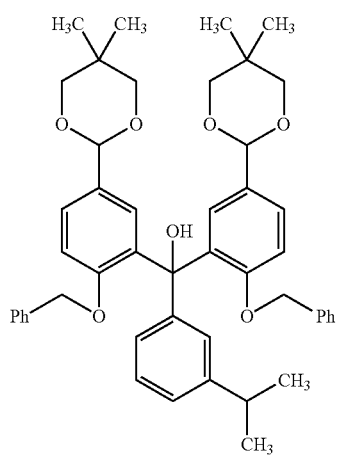

3(e)

N,N,N',N'-Tetramethylethylenediamine (30.18 ml, 0.2 mol) was added to a solution of compound 3(d) (75.45 g, 0.2 mol) in dry tetrahydrofuran (500 ml), under argon. The solution was cooled to −70° C., and n-butyllithium (88 ml, 2.5 M in cyclohexane) was added over 30 minutes. The reaction mixture was stirred at −70° C. for 1.5 hours. Ethyl 3-isopropylbenzoate (17.3 g, 0.09 mol) was added to the solution, and the mixture was stirred at −70° C. for 1 hour, and then slowly warmed to room temperature. The reaction was concentrated on rotary evaporator, and the crude product was dissolved in ethyl acetate, rinsed with water, dried with magnesium sulfate, and concentrated on rotary evaporator. The product was purified via flash chromatography (silica gel, hexanes/ethyl acetate gradient) producing 53.4 g of the desired product.

f. Preparation of:

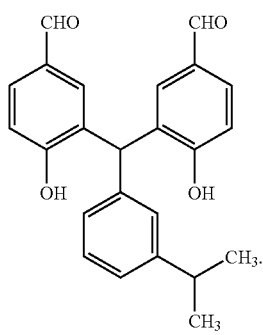

3(f)

Compound 3(e) (22.0 g, 30 mmol) was dissolved in formic acid (500 ml) and heated to reflux for about 6 hours. The reaction was cooled to room temperature, and the solids were filtered, washed with water, and air-dried. Water was added to the mother liquor to produce more precipitate, which was filtered, washed with water, and air-dried. The solids were combined and purified by recrystallization (ethyl acetate/dichloromethane), to give 7.97 g of the desired product g. 2,2'-[[3-(Methlethyl)phenyl]methylene]bis[4-[[5-methyl-1H-tetrazol-1-yl)imino]methyl]]phenol. Compound 3(f) (7.49 g, 20 mmol) was dissolved in absolute ethanol (200 ml) and added dropwise to a refluxing solution of 1-amino-5-methyltetrazole (5.95 g, 60 mmol), p-toluenesulfonic acid monohydrate (0.3 g, 1.6 mmol) and ethanol (300 ml), under argon. An additional amount of ethanol (200 ml) was added after a solid began to form in the reaction vessel. The reaction was heated to reflux for 6 hours, and then cooled to room temperature. A solid was collected by filtration, rinsed with ethanol, and air-dried. The solid was recrystallized in hot ethanol, providing 7.4 g of the desired product.

Example 4

Preparation of 2,2'-[(3-Methylphenyl)methylene]bis [4-[[(5-methyl-1H-tetrazol-1-yl)imino]methyl]]phenol a. 2-(3-Bromo-4-methoxyphenyl)-5,5-dimethyl-1,3-dioxane. A solution of 3-bromo-4-methoxybenzaldehyde (74.65 g, 0.347 mol), neopentyl glycol (43.35 g, 0.416 mol), pyridinium p-toluenesulfonate (0.87 g, 0.035 mol), and benzene (1.8 L) was refluxed with azeotropic removal of water for 6 hours. The reaction mixture was cooled to room temperature and diluted with water. The aqueous phase was extracted with ethyl acetate. The combined organic phases were washed with brine, dried (Na$_2$SO$_4$), charcoaled, filtered through a short column of Florisil™, and concentrated in vacuo. There was obtained 102.8 g (98%) of ketal as a peach colored solid.

b. Preparation of:

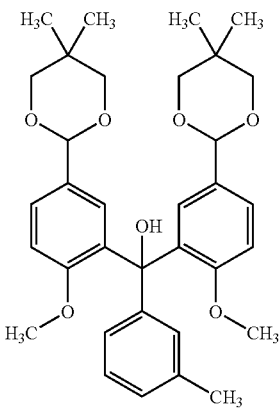

4(b)

N,N,N',N'-Tetramethylethylenediamine (9.05 ml, 60 mmol) was added to a solution of 2-(3-bromo-4-methoxyphenyl)-5,5 dimethyl-1,3-dioxane (15.06 g, 50 mmol) in anhydrous tetrahydrofuran (150 ml) that was cooled to −70° C., followed by the slow addition of n-butyllithium (24 ml, 60 mmol). After 15 minutes, a solution of methyl m-toluate (3.00 g, 20 mmol) was added dropwise over a period of 5 minutes. The mixture was stirred at room temperature for 3 hours, and quenched with 10% NH$_4$Cl (20 ml). t-Butyl methyl ether was added and the layers separated. The organic phase was washed with water (3×150 ml), dried (MgSO$_4$), filtered and concentrated in vacuo. The yellow oil was purified via flash chromatography (silica gel, hexanes/ethyl acetate gradient), followed by a recrystallization in methanol to provide 2.53 g of the desired product.

c. Preparation of:

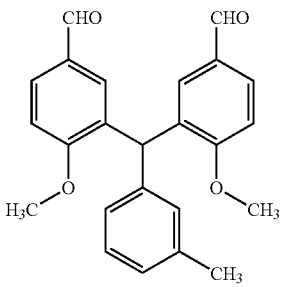

4(c)

Hydriodic acid (5 ml, 58 wt % in water) was added to a solution of compound 4(b) (1.70 g, 30 mmol) dissolved in glacial acetic acid (20 ml). The reaction mixture was stirred at room temperature for 30 minutes, and then concentrated in vacuo, dissolved in ethyl acetate, and washed with water (2×100 ml), Na$_2$SO$_3$ solution (2×100 ml), NaHCO$_3$ solution (2×100 ml), and saturated aqueous NaCl solution. The organics were dried over magnesium sulfate, filtered, and rotary evaporated. The resulting solid was crystallized in ethyl acetate/hexanes, to provide 0.68 g (60%) of the desired product.

d. Preparation of:

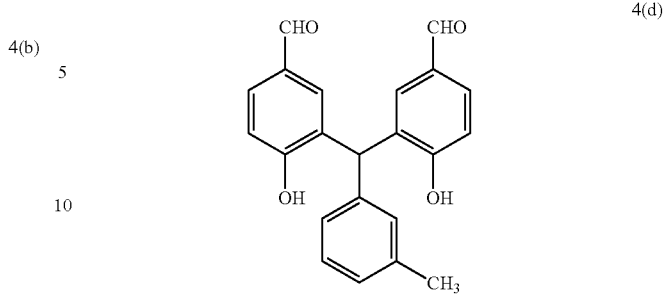

4(d)

A mixture of compound 4(c) (1.40 g, 3.7 mmol) and pyridine hydrochloride (8.67 g, 75 mmol) was heated to 200° C. for 6 hours. The mixture was diluted with water, and a solid was obtained by filtration. The solid was purified via flash chromatography (silica gel, hexanes/acetone gradient) providing the desired product.

e. 2,2'-[(3-Methylphenyl)methylene]bis[4-[[(5-methyl-1H-tetrazol-1-yl)imino]methyl]]phenol. 1-Amino-5-methyltetrazole (0.16 g, 1.6 mmol) and p-toluenesulfonic acid monohydrate (15 mg, 0.08 mmol) were dissolved in ethanol and brought to reflux temperature. Compound 4(d) (0.15 g, 0.40 mmol) was dissolved in ethanol (10 ml) and added to the refluxing solution. The reaction was heated to reflux for 3 hours, and cooled to room temperature. A solid was collected by filtration and dried under vacuum to provide the desired product.

Example 5

Preparation of 2,2'-[(3-Methoxyphenyl)methylene]bis[4-[[(5-methyl-1H-tetrazol-1-yl)imino]methyl]]phenol
a Preparation of:

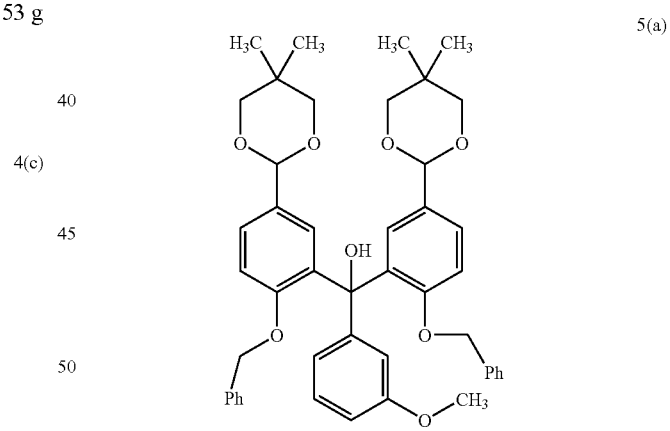

5(a)

N,N,N',N'-Tetramethylethylenediamine (2.10 ml, 14 mmol) was added to a solution of compound 3(d) (5.28 g, 14 mmol, which can be prepared according to example 3, steps b-d, above) in anhydrous tetrahydrofuran (100 ml). The mixture was cooled to −70° C., and n-butyllithium (5.6 ml, 14 mmol) was added slowly. After 1 hour, a solution of methyl 3-methoxybenzoate (1.08 g, 6.5 mmol) in tetrahydrofuran (20 ml) was added dropwise over 10 minutes. The mixture was stirred at room temperature for 2 hours, and quenched with 10% NH$_4$Cl (20 ml). t-Butyl methyl ether was added, and the layers were separated. The organic phase was washed with water (3×150 ml), dried (MgSO$_4$), filtered, and concentrated in vacuo. The crude product was purified via flash chromatography (silica gel, hexanes/ethyl acetate gradient), to provide 3.28 g of the desired product.

b. Preparation of:

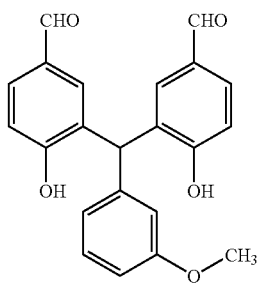

5(b)

A solution of compound 5(a) (1.0 g, 1.4 mmol) in formic acid (20 ml) was heated to reflux for 7 hours. After cooling, the mixture was poured over ice water, and a solid was isolated via filtration. The blue/green solid was purified via flash chromatography (silica gel, hexanes/ethyl acetate gradient), followed by a recrystallization in acetic acid to provide 0.79 g of the desired product.

c. 2,2'-[(3-Methoxyphenyl)methylene]bis[4-[[(5-methyl-1H-tetrazol-1-yl)imino]methyl]]phenol. The title compound was obtained essentially according to step e in Example 4, above, however compound 5(b) was used instead of compound 4(d).

Example 6

Preparation of 2,2'-[(3-Ethoxyphenyl)methylene]bis[4-[[(5-methyl-1H-tetrazol-1-yl)imino]methyl]]phenol The title compound was prepared essentially according to the basic procedure described in Example 5, above; however, methyl 3-ethoxybenzoate was used in step a instead of methyl 3-methoxybenzoate.

Example 7

Preparation of 2,2'-[(3-Chlorophenyl)methylene]bis[4-[[(5-methyl-1H-tetrazol-1-yl)imino]methyl]]phenol a. Preparation of:

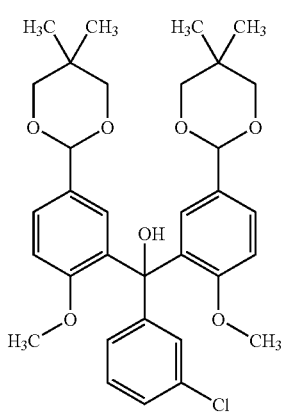

7(a)

N,N,N',N'-Tetramethylethylenediamine (8.95 ml, 0.1 mol) was added to a solution of 2-(3-bromo-4-methoxyphenyl)-5,5-dimethyl-1,3-dioxane (24.09 g, 0.08 mol), prepared according to step a, Example 4 above, in anhydrous tetrahydrofuran (150 ml), and the solution was cooled to −78° C. in a dry ice/isopropanol bath. n-Butyllithium (36 ml, 0.09 mol, 2.5M) was added over 20 minutes. After stirring for 15 minutes, a solution of methyl 3-chlorobenzoate (5.97 g, 0.035 mol) in tetrahydrofuran was added to the reaction. The mixture was warmed to room temperature, quenched with water (5 ml), and concentrated in vacuo. The crude product was diluted with ethyl acetate, rinsed with water, and dried (MgSO$_4$). The solvent was removed by rotary evaporation, and the product was purified via recrystallization from methanol to provide 7.4 g of the desired product.

b. Preparation of:

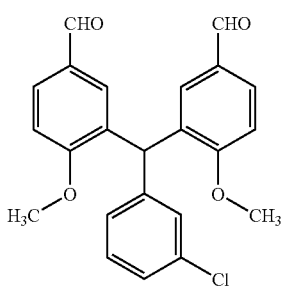

7(b)

Hydriodic acid (10 ml, 57 wt % in water) was added to a solution of compound 7(a) (5.83 g, 10 mmol) dissolved in glacial acetic acid (50 ml). The reaction was stirred at room temperature for 1 hour. The acetic acid was removed in vacuo. The crude product was dissolved in ethyl acetate and rinsed with water, saturated Na$_2$SO$_3$ (2×), and brine. The solution was dried (MgSO$_4$) and concentrated. The desired product (3.6 g) was isolated via recrystallization in ethyl acetate/hexanes.

c. Preparation of:

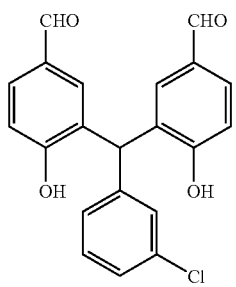

7(c)

A mixture of compound 7(b) (1.97 g, 5 mmol) and pyridine hydrochloride (11.26 g, 100 mmol) was heated to 190-210° C. for 2 hours. The mixture was cooled to room temperature and diluted with water. A solid was obtained by filtration. Since the reaction was incomplete, the solid was resubjected to reaction conditions, and then cooled to room temperature, diluted with water, and filtered. The isolated solid was purified via recrystallization in acetic acid/ethanol, providing the desired product.

d. 2,2'-[(3-Chlorophenyl)methylene]bis[4-[[(5-methyl-1H-tetrazol-1-yl)imino]methyl]]phenol. A solution of compound 7(c) (0.15 g, 0.4 mmol), dry N,N-dimethylformamide, and 1-amino-5-methyltetrazole (0.24 g, 2.4 mmol) was heated to reflux for 12 hours. The reaction mixture was cooled to room temperature, diluted with water, and filtered. The isolated solid was recrystallized in tetrahydrofuran/ethanol to provide the titled compound.

Example 8

Preparation of 2,2'-[(3-Bromophenyl)methylene]bis [4-[[(5-methyl-1H-tetrazol-1-yl)imino]methyl]]phenol a. Preparation of:

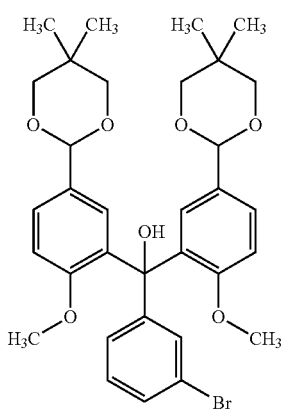

8(a)

N,N,N',N'-Tetramethylethylenediamine (45.28 ml, 0.3 mol) was added to a solution of 2-(3-bromo-4-methoxyphenyl)-5,5-dimethyl-1,3-dioxane (90.35 g, 0.3 mol), prepared according to step a, Example 4 above, in anhydrous tetrahydrofuran. The solution was cooled to −78° C. in a dry ice/isopropanol bath and n-butyllithium (120 ml, 0.3 mol, 2.5M) was added. After stirring for 15 minutes, a solution of methyl 3-bromobenzoate (32.07 g, 0.14 mol) in tetrahydrofuran was added to the reaction. The mixture was warmed to room temperature, quenched with water, and concentrated in vacuo. The crude product was diluted with ethyl acetate, and a solid precipitated after rinsing with water. The solid was isolated via filtration, and recrystallized in chloroform and ethyl acetate to provide the desired product (64.4 g).
b. Preparation of:

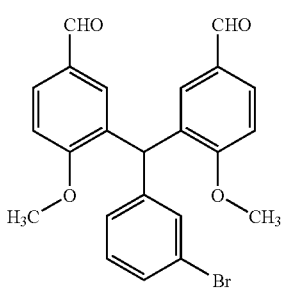

8(b)

Hydriodic acid (88 ml, 57 wt % in water) was added to a solution of compound 8(a) (55.1 g, 88 mmol) dissolved in glacial acetic acid (200 ml). The reaction was stirred at room temperature for 1 hour. The acetic acid was removed in vacuo. The crude product was dissolved in ethyl acetate and rinsed with water, saturated $Na_2SO_3$ (2×), and brine. The solution was dried with $MgSO_4$, but began to crystallize. The solids were dissolved in chloroform, filtered, and concentrated, providing the desired product (22.2 g).
c. Preparation of:

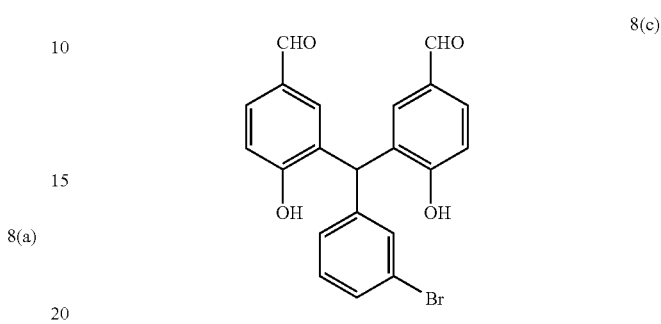

8(c)

A mixture of compound 8(b) (7.0 g, 0.016 mol) and pyridine hydrochloride (18.5 g, 0.16 mol) was heated to 200-220° C. for 2 hours, under argon. The mixture was cooled to room temperature and diluted with water. A solid was obtained by filtration. The solid was purified via flash chromatography (silica gel, acetone/hexanes gradient), followed by recrystallization in ethyl acetate and methanol, providing 1.75 g of the desired product.

d. 2,2'-[(3-Bromophenyl)methylene]bis[4-[[(5-methyl-1H-tetrazol-1-yl)imino]methyl]]phenol. Compound 8(c) (0.3 g, 0.73 mmol), 1-amino-5-methyltetrazole (0.398 g, 4.0 mmol), and catalytic p-toluenesulfonic acid monohydrate were mixed with dry N,N-dimethylformamide, under argon. The reaction was heated to reflux until completion, diluted with water, and filtered to provide the desired product.

Example 9

Preparation of 2,2'-[[3-(2-Ethylbutyl)phenyl]methylene]bis[4-[[(5-methyl-1H-tetrazol-1-yl)imino]methyl]]phenol a. Preparation of:

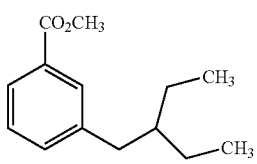

9(a)

Palladium catalyst ([1,1'-bis(diphenylphosphino)ferrocene]dichloropalladium(II), complex with dichloromethane (1:1), 0.69 g, 0.85 mmol) was added to a solution of methyl-3-bromobenzoate (3.66 g, 17 mmol) in distilled tetrahydrofuran (80 ml). Next, 2-ethylbutyl zinc bromide (5.76 g, 25 mmol) was added, and the reaction mixture was stirred at room temperature overnight. The reaction was quenched with $NH_4Cl$ and extracted with ethyl acetate (3×). The organic layers were combined, washed with brine, dried ($MgSO_4$), filtered, and concentrated. The product was purified via HPLC (silica gel, ethyl acetate/hexanes gradient), providing 2.04 g (54.4%) of the desired product.

b. Preparation of:

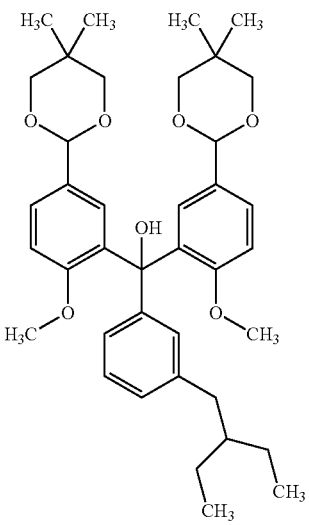

9(b)

A solution of 2-(3-bromo-4-methoxyphenyl)-5,5-dimethyl-1,3-dioxane (5.41 g, 18 mmol), prepared according to step a, Example 4 above, in anhydrous tetrahydrofuran (60 ml) was cooled to −65° C. n-Butyllithium (8.2 ml of 2.5M in hexanes) was added via syringe pump. After 15 minutes, a solution of compound 9(a) (1.8 g, 8.17 mmol) in tetrahydrofuran (10 ml) was added dropwise. The mixture was stirred at −65° C. for 1 hour and then at room temperature overnight. The reaction mixture was quenched with saturated NH$_4$Cl, and the layers were separated. The aqueous phase was extracted with ethyl acetate (2×). The combined organic phases were washed with brine, dried (MgSO$_4$), filtered, and concentrated in vacuo. The oil obtained was dissolved in hot hexanes, and cooled to room temperature. The resulting white solid was isolated and dried in vacuo to provide 2.29 g (44.3%) of the desired product.

c. Preparation of:

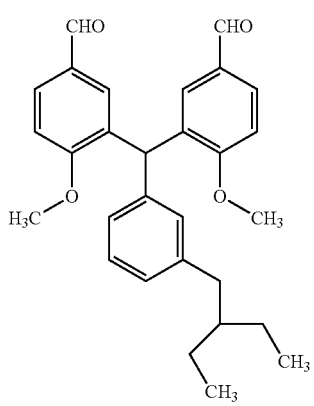

9(c)

Hydriodic acid (2.5 ml, 57 wt % in water) was added dropwise to a solution of compound 9(b) (1.6 g, 2.53 mmol) in glacial acetic acid (38 ml). The reaction was stirred at room temperature for 4 hours, under argon. The acetic acid was removed by rotary evaporation, and the remaining oil was dissolved in ethyl acetate. The solution was washed with saturated aqueous NaHSO$_3$, dried over magnesium sulfate, and rotary evaporated. The resulting solid was purified via flash chromatography (silica gel, ethyl acetate/hexanes), then recrystallized in hexanes to provide 408 mg (36.4%) of the desired product as a white solid.

d. Preparation of:

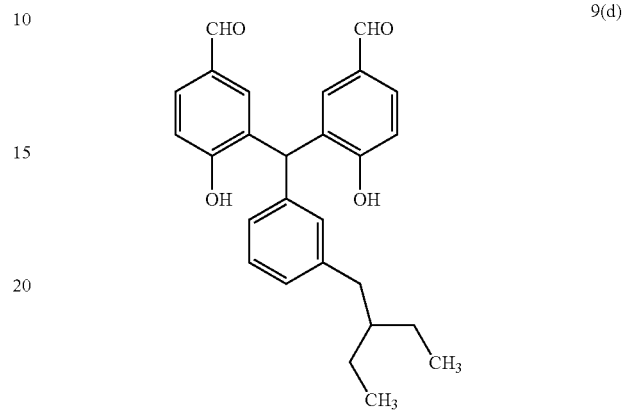

9(d)

Boron tribromide solution (5.3 ml of 1M in dichloromethane) was added dropwise to a solution of compound 9(c) (0.395 g, 0.88 mmol) in dry dichloromethane (7.0 ml) at 0° C. After stirring about 18 hours at room temperature, the reaction mixture was poured onto crushed ice and stirred until the ice melted. The resulting solid was extracted into ethyl acetate. The ethyl acetate solution was dried over MgSO$_4$, filtered, and evaporated. The crude product was purified via flash chromatography (silica gel, 30% ethyl acetate in hexanes) to provide 235 mg (63.5%) of the pure product.

e. 2,2'-[[3-(2-Ethylbutyl)phenyl]methylene]bis[4-[[(5-methyl-1H-tetrazol-1-yl)imino]methyl]]phenol. The title compound was obtained essentially according to step e in Example 4, above; however compound 9(d) was used instead of compound 4(d).

Example 10

Preparation of 2,2'-[[3-Cyclohexylphenyl]methylene]
bis[4-[[(5-methyl-1H-tetrazol-1-yl)imino]methyl]]
phenol The title compound was prepared essentially according to the basic procedure described Example 9, above; however, cyclohexylzinc bromide was used in step a instead of 2-ethylbutylzinc bromide.

Example 11

Preparation of 2,2'-[(3-Butylphenyl)methylene]bis[4-
[[(5-methyl-1H-tetrazol-1-yl)imino]methyl]]phenol The title compound was prepared essentially according to the basic procedure described in Example 9, above; however, butylzinc bromide was used in step a instead of 2-ethylbutylzinc bromide.

Example 12

Preparation of 2,2'-[(3-Fluorophenyl)methylene]bis[4-[[(5-methyl-1H-tetrazol-1-yl)imino]methyl]]phenol The title compound was prepared essentially according to the basic procedure described in steps b-e, Example 9, above; however, ethyl 3-fluorobenzoate was used in step b instead of compound 9(a).

Example 13

Preparation of 2,2'-[(3-Pentylphenyl)methylene]bis[4-[[(5-methyl-1H-tetrazol-1-yl)imino]methyl]]phenol The title compound was prepared essentially according to the basic procedure described in Example 9, above; however, pentylzinc bromide was used in step a instead of 2-ethylbutylzinc bromide.

Example 14

Preparation of 2,2'-[[3-(1-Methylpropyl)phenyl]methylene]bis[4-[[(5-methyl-1H-tetrazol-1-yl)imino]methyl]]phenol The title compound was prepared essentially according to the basic procedure described in Example 9, above; however, sec-butylzinc bromide was used in step a instead of 2-ethylbutylzinc bromide.

Example 15

Preparation of 2,2'-[[3-(2-Methylpropyl)phenyl]methylene]bis[4-[[(5-methyl-1H-tetrazol-1-yl)imino]methyl]]phenol a. Preparation of:

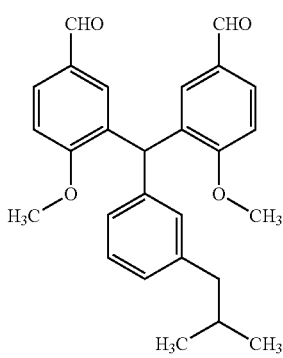

15(a)

The compound 15(a) was prepared essentially according to steps a-c, Example 9, above; however, isobutylzinc bromide was used in step a instead of 2-ethylbutylzinc bromide.

b. Preparation of:

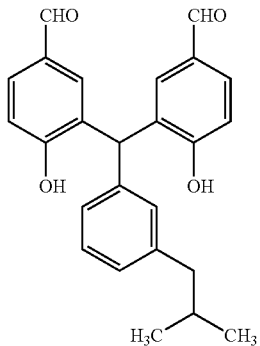

15(b)

A mixture of compound 15(a) (0.25 g, 0.6 Mmol) and pyridine hydrochloride (1.39 g, 12 mmol) was heated to 180° C. for 1.5 hours. The mixture was cooled to room temperature, diluted with water, and sonicated with 1N hydrochloric acid. A solid was obtained by filtration, and purified by triturating with dichloromethane, ethyl acetate, and tetrahydrofuran, separately, to extract the desired product (0.131 g).

c. 2,2'-r[3-(2-Methylpropyl)phenyl]methylene]bis[4-[[(5-methyl-1H-tetrazol-1-yl)imino]methyl]]phenol. Compound 15(b) (0.13 g, 0.34 mmol) was mixed with 1-amino-5-methyltetrazole (0.10 g, 1.01 mmol), pyridinium para-toluenesulfonate (catalytic) and absolute ethanol (15 ml), and stirred at room temperature overnight. The ethanol was removed by rotary evaporation, and the remaining solid was sonicated with water. The solid was collected by filtration and dried under vacuum. The crude product was recrystallized in hot ethanol to give 0.056 g of the title compound.

Example 16

Preparation of 2,2'-[[(3-Methoxyethyl)phenyl]methylene]bis[4-[[(5-methyl-1H-tetrazol-1-yl)imino]methyl]]phenol a. N-methoxy-N,N',N'-trimethylurea. A mixture of dimethylhydroxylamine hydrochloride (150.0 g, 1.54 mol), 4-dimethylaminopyridine (9.4 g, 0.076 mol), and dichloromethane (1.35 L) was chilled to −20° C., under argon. Dimethylcarbamyl chloride (135 ml, 1.46 mol) and pyridine (315 ml) were added consecutively over 25 minutes. The reaction was slowly warmed to room temperature and agitated for about 18 hours. The reaction mixture was filtered to remove pyridine hydrochloride and concentrated by rotary evaporator. The mixture was diluted with t-butyl methyl ether, and the solids were removed by filtration. The filtrate was concentrated by rotary evaporation. Vacuum distillation provided desired product (135.10 g, 69%) as a colorless oil.

b. Preparation of:

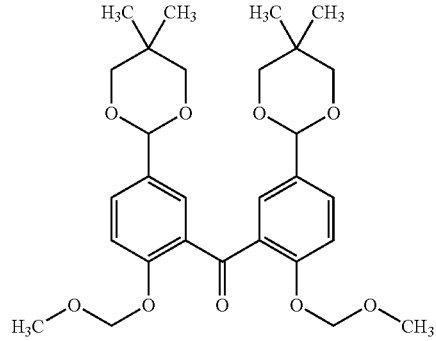

16(b)

A mixture of 2-(4-methoxymethoxyphenyl)-5,5-dimethyl-1,3-dioxane, prepared according to Example 1, step b above, (62.7 g, 189.3 mmol) and t-butyl methyl ether (400 ml) was cooled to −20° C. n-Butyllithium (130 ml, 208.0 mmol, 1.6 M in hexanes) was added slowly. After 10 minutes, a solution of N-methoxy-N,N',N'-trimethylurea (11.0 g, 83.2 mmol) in t-butyl methyl ether (115 ml) was added dropwise. The mixture was stirred at −20° C. for 1.5 hours and at 0° C. overnight. The reaction mixture was quenched with saturated NH$_4$Cl (125 ml), and the layers were separated. The combined organic phases were washed with water (200 ml) and brine (200 ml) and concentrated in vacuo. The orange oil was purified via several chromatography columns (silica gel, ethyl acetate/hexanes), then crystallized in ethanol/water, providing the desired product (30.22 g).

c. Preparation of:

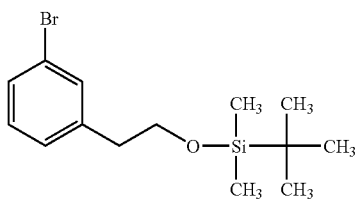

16(c)

3-Bromophenethyl alcohol (5.18 g, 25.8 mmol) was mixed with tert-butyldimethylsilyl chloride (4.24 g, 28.16 mmol), imidazole (1.91 g, 28.16 mmol), and N,N-dimethylformamide (15 ml), and stirred at room temperature for about 18 hours. The product was partitioned between ethyl acetate and water. The aqueous layer was washed with ethyl acetate, and the organics were combined, washed with brine, dried over MgSO$_4$, and filtered. The filtrate was concentrated in vacuo to provide 8.07 g of the desired product.

d. Preparation of:

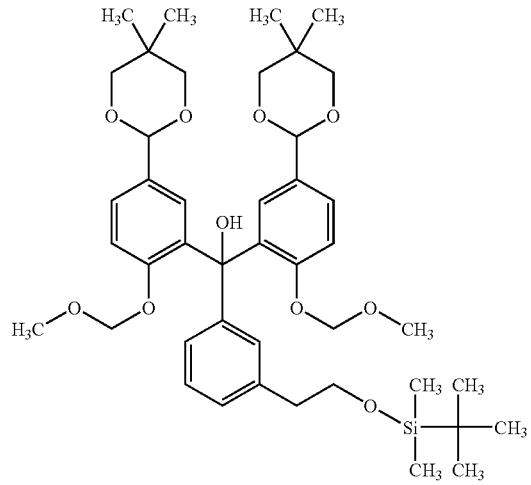

16(d)

A solution of compound 16(c) (3.27 g, 10.36 mmol) in anhydrous tetrahydrofuran was cooled to −78° C., under argon. n-Butyllithium (3.76 ml of 2.5M) was added slowly. After 5 minutes, a solution of compound 16(b) (5.00 g, 9.42 mmol) in tetrahydrofuran (40 ml) was added dropwise. The mixture was slowly warmed to room temperature, stirred overnight, and quenched with 10% NH$_4$Cl (1 L). The solution was extracted with ethyl acetate (2×60 ml). The combined organic phases were washed with brine, dried (MgSO$_4$), filtered and concentrated in vacuo. The crude product was purified via flash chromatography (silica gel, 30% ethyl acetate in hexanes), providing 7.22 g (46%) of the desired product.

e. Preparation of:

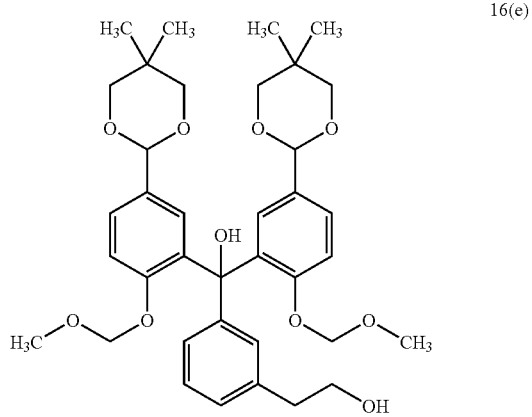

16(e)

Tetrabutylammonium fluoride (4.5 ml of 1.0M in tetrahydrofuran) was added to a solution of compound 16(d) (3.13 g, 4.08 mmol) in tetrahydrofuran (15 ml). The reaction mixture was stirred at room temperature, under argon, overnight. The solution was partitioned between ethyl acetate and water, and the layers were separated. The aqueous layer was extracted with ethyl acetate (2×50 ml), and the combined organics were washed with brine, dried (MgSO$_4$), filtered, and concentrated in vacuo. The crude product was purified via dry-flash chromatography (silica gel, 10% ethyl acetate in hexanes), providing 2.05 g of the desired product.

f. Preparation of:

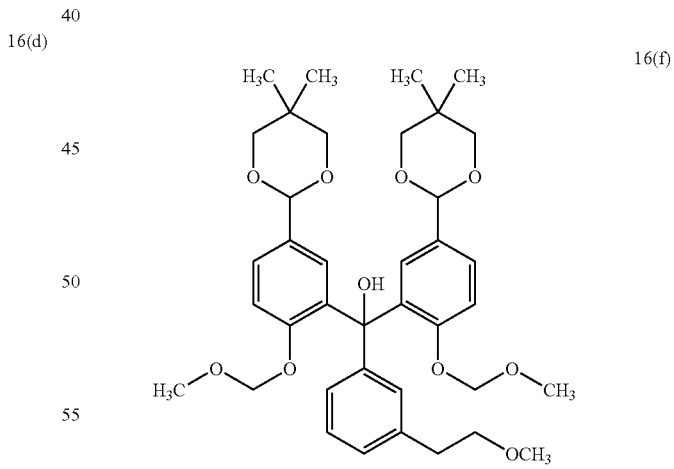

16(f)

Compound 16(e) (0.69 g, 1.06 mmol) was added dropwise to a refluxing suspension of sodium hydride (86 mg, 3.59 mmol) in tetrahydrofuran. After completion of addition and cessation of hydrogen evolution, iodomethane (0.99 ml, 1.59 mmol) was added. The reaction mixture was stirred for 2 hours at refluxing temperature, then cooled to room temperature. The reaction was quenched slowly with water and extracted with ethyl acetate (2×50 ml). The combined organic layers were washed with brine, dried (MgSO$_4$), filtered, and concentrated in vacuo. The product was purified via flash chromatography (silica gel, 25% ethyl acetate in hexanes), providing 0.32 g (45%) of the desired product.

g. Preparation of:

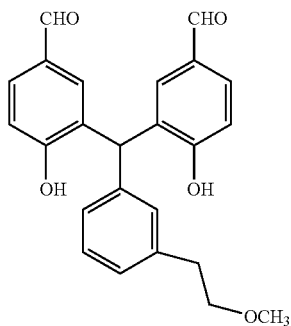

16(g)

Hydriodic acid (0.4 ml, 1 ml/mmol) was added to a solution of compound 16(f) (0.26 g, 0.381 mmol) dissolved in glacial acetic acid (3 ml). The reaction was stirred at room temperature for 3 hours. The reaction mixture was quenched with water (50 ml), and then extracted with ethyl acetate (2×50 ml). The combined organic layers were washed with 10% aqueous NaHSO₃ and saturated aqueous NaCl solution. The organics were dried over magnesium sulfate, filtered, and rotary evaporated. This crude product was purified via flash chromatography (silica gel, 40% hexanes in ethyl acetate) to provide 0.296 g of the desired product.

h. 2,2'-[[(3-Methoxyethyl)phenyl]methylene]bis[4-[[(5-methyl-1H-tetrazol-1-yl)imino]methyl]]phenol. Compound 16(g) (0.21 g, 0.53 mmol) was added dropwise to a refluxing solution of 1-amino-5-methyltetrazole (0.16 g, 1.59 mmol) and pyridinium para-toluenesulfonate (13 mg, 0.053 mmol) in ethanol, under argon. The reaction was heated to reflux for 2 hours, and then cooled to room temperature. The solid was isolated via filtration, washed with ethanol, and dried to provide 0.23 g of the title compound.

Example 17

Preparation of 2,2'-[(3-Ethylphenyl)methylene]bis[4-[[(5-methyl-1H-tetrazol-1-yl)imino]methyl]]phenol a. Preparation of:

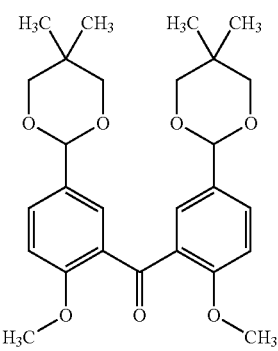

17(a)

A solution of 2-(3-bromo-4-methoxyphenyl)-5,5-dimethyl 1,3-dioxane (75.30 g, 0.25 mol), prepared according to step a, Example 4 above, in anhydrous tetrahydrofuran (500 ml) was cooled to −78° C., under argon. n-Butyllithium (104 ml, 0.26 mol, 2.5M) was added over 60 minutes. After 15 minutes, a solution of N-methoxy-N,N',N'-trimethylurea, (13.22 g, 0.10 mol), prepared according to step a, Example 16, in tetrahydrofuran (50 ml) was added dropwise. The reaction mixture was warmed to room temperature, quenched with 10% NH₄Cl (300 ml), diluted with t-butyl methyl ether, and the layers were separated. The organic phase was washed with water (4×), dried (MgSO₄), and concentrated in vacuo. The residue was purified via crystallization in ethyl acetate, providing the desired product (28.5 g).

b. Preparation of:

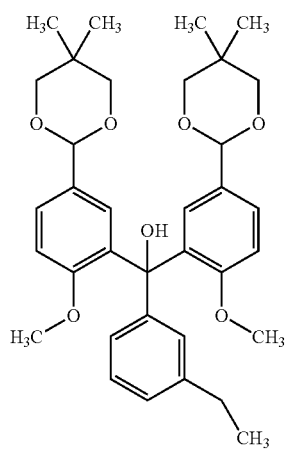

17(b)

N,N,N',N'-Tetramethylethylenediamine (8.16 ml, 54 mmol) was added to a solution of 1-bromo-3-ethyl-benzene (10.0 g, 54 mmol) in dry tetrahydrofuran (600 ml), under argon. The solution was cooled to −70° C., and n-butyllithium (21.6 ml, 54 mmol) was added slowly, and the reaction was stirred at −70° C. for 1.5 hours. Compound 17(a) (23.06 g, 49 mmol), dissolved in tetrahydrofuran (100 ml) was added to the solution. The mixture was stirred at −70° C. for 1 hour, and then slowly warmed to room temperature. The reaction was quenched with aqueous NH₄Cl (30 ml) and concentrated on a rotary evaporator. The crude product was dissolved in t-butyl methyl ether and rinsed with water (2×250 ml), dried with magnesium sulfate, filtered, and concentrated on a rotary evaporator. The product was recrystallized from methanol to provide 16.01 g of the desired product.

b. Preparation of:

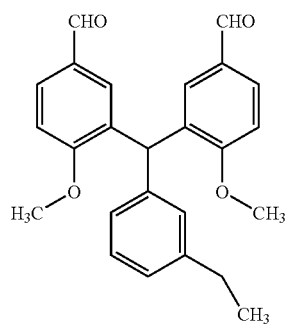

17(c)

Hydriodic acid (30 ml, 58 wt % in water) was added to a solution of compound 17(b) (9.28 g, 7 mmol) dissolved in glacial acetic acid (90 ml). The reaction was stirred at room temperature for 1.5 hours. The acetic acid was removed in vacuo. The crude product was dissolved in t-butyl methyl ether and rinsed with saturated aqueous $Na_2SO_3$ (2×250 ml), aqueous $NaHCO_3$, and brine. The solution was dried ($MgSO_4$), filtered, and concentrated. The crude product was then purified via column chromatography (silica gel, ethyl acetate/hexanes gradient) to provide 2.88 g of the desired product as a white solid.

d. Preparation of:

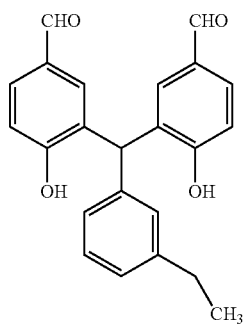

17(d)

A mixture of compound 17(c) (2.15 g, 6 mmol) and pyridine hydrochloride (13.86 g, 120 mmol) was heated to reflux, under argon, for 3.5 hours. The mixture was cooled to room temperature and diluted with water. A solid was obtained by filtration, and purified via column chromatography (silica gel, ethyl acetate/hexanes gradient), providing 0.34 g of the desired product.

e. 2,2'-[(3-Ethylphenyl)methylene]bis[4-[[(5-methyl-1H-tetrazol-1-yl)imino]methyl]]phenol. Compound 17(d) (0.15 g, 0.4 mmol) was dissolved in warm ethanol (6 ml) and added to a refluxing solution of 1-amino-5-methyltetrazole (0.24 g, 2.4 mmol) and p-toluenesulfonic acid monohydrate (0.038 g, 0.2 mmol) in 5 ml ethanol, under argon. The reaction was heated to reflux for 2 hours, and then cooled to room temperature. A white solid was collected by filtration and dried under vacuum, yielding 0.178 g of the titled compound.

Example 18

Preparation of 2,2'-[[3-[Ethyl(methylethyl)amino] phenyl]methylene]bis[4-[[(5-methyl-1H-tetrazol-1-yl)imino]methyl]]phenol a. Preparation of:

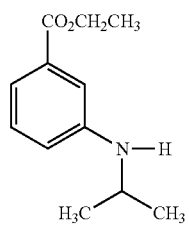

18(a)

Ethyl 3-aminobenzoate hydrochloride (27.70 g, 137 mmol) was suspended and mechanically stirred in tetrahydrofuran (350 ml) under argon. Acetone (20.17 ml, 275 mmol) and sodium borohydride (5 20 g, 137 mmol) were added to the mixture. The suspension was cooled in an ice/ethanol bath, and a solution of tetrahydrofuran (10 ml) and water (5 ml) was added dropwise. The mixture was allowed to stir at room temperature overnight.

Water (25 ml) was slowly added to the reaction to quench the sodium borohydride. A saturated aqueous solution of sodium chloride (400 ml) was added, and the layers were separated. The aqueous layer was extracted with t-butyl methyl ether. The organic layers were combined, dried with saturated sodium chloride and sodium sulfate, and concentrated on rotary evaporator to provide 28.6 g of the desired product as an oil.

b. Preparation of:

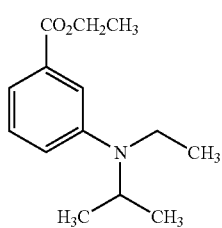

18(b)

N,N-Diisopropylethylamine (37.61 g, 291 mmol) and ethyl iodide (151.2 g, 970 mmol) were added to a mixture of compound 18(a) (20.0 g, 97 mmol) in acetonitrile (300 ml). The mixture was heated to reflux for about 10 hours. The reaction was cooled to room temperature, and the solvent was removed in vacuo. Water was added, and the product was extracted with ethyl acetate (3×250 ml). The organic layers were combined and dried with saturated aqueous NaCl and $MgSO_4$, filtered, and concentrated in vacuo. The crude product was purified via column chromatography (25% ethyl acetate in hexanes) to provide 20.4 g of the desired product.

c. Preparation of:

18(c)

2-(4-Methoxymethoxyphenyl)-5,5-dimethyl-1,3-dioxane (30.06 g, 119 mmol), prepared according to Example 1, step b, above, was mixed with dry tetrahydrofuran (385 ml) in a 3-neck flask, under argon. N,N,N',N'-Tetramethylethylenediamine (17.9 ml, 119 mmol) was added to the solution, and the resulting mixture was cooled to around −5° C. in an ice/NaCl bath. Sec-butyllithium (100 ml, 1.3M in cyclohexane) was added via a syringe pump, maintaining the temperature of the reaction around 0° C. The reaction was stirred for 15 minutes, then a solution of compound 18(b) (9.32 g, 40 mmol) in dry tetrahydrofuran (160 ml) was added dropwise to the reaction. After this addition, the solution was stirred for 2 hours at 0° C. The reaction was then quenched with 20% aqueous $NH_4Cl$ (100 ml), and the organic solvents were removed in vacuo. The mixture was extracted two times with ethyl acetate (400 ml). The organic layers were combined, washed with saturated aqueous NaCl, dried with magnesium sulfate, filtered, and concentrated on rotary evaporator. The crude product was chromatographed (silica gel, 15-20% ethyl acetate in hexanes), yielding 8.77 g of the desired product.

d. Preparation of:

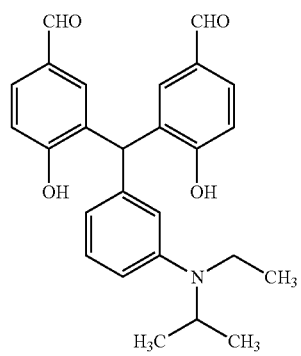

18(d)

Hydriodic acid (7.2 ml, 58 wt % in water) was added to a solution of compound 18(c) (5.00 g, 7.2 mmol) in glacial acetic acid (72 ml). The reaction was stirred at room temperature for 2 hours. The acetic acid was removed in vacuo. The residue was dissolved in 10% sodium bisulfite solution and ethyl acetate, and NaHCO$_3$ was added until pH 7. The solution was extracted with ethyl acetate (2×200 mL). The organics were dried over magnesium sulfate, filtered, and rotary evaporated. The crude product was chromatographed (silica gel, 50-100% ethyl acetate in hexanes) yielding 0.78 g of the desired product.

e. 2,2'-[[[3-Ethyl(methylethyl)amino]phenyl]methylene] bis[4-[[(5-methyl-1H-tetrazol-1-yl)imino]methyl]]phenol. Compound 18(d) (0.5 g, 1.2 mmol) was dissolved in 12 ml absolute ethanol, and added dropwise to a refluxing solution of 1-amino-5-methyltetrazole (0.36 g, 3.6 mmol) and pyridinium para-toluenesulfonate (0.33 g, 1.3 mmol) in 12 ml ethanol, under argon. The reaction was heated to reflux for 2 hours, and then cooled to room temperature. Tert-butyl methyl ether was added to precipitate the tosylate salt which was collected by filtration. The solid was suspended in water and ethyl acetate and NaHCO$_3$ was added. The solution was extracted with ethyl acetate (2×50 ml). The organics were dried over magnesium sulfate, filtered, and rotary evaporated to yield 0.43 g of the title compound.

Example 19

Preparation of 2,2'-[[3(Ethylpropylamino)phenyl] methylene]bis[4-[[(5-methyl-1H-tetrazol-1-yl)imino] methyl]]phenol a. Preparation of:

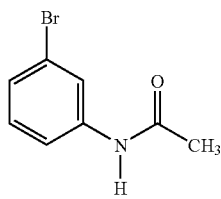

19(a)

Triethylamine (18.73 ml, 134.4 mmol) was added to a solution of 2-bromoaniline (11.56 g, 97.2 mmol) in dichloromethane (100 ml). Acetic anhydride (7.61 ml, 80.64 mmol) was slowly added to the mixture. An exothermic reaction caused the solution to gently reflux for about 15 minutes. The reaction was stirred for two hours, diluted with dichloromethane (70 ml), washed with HCl (1M), washed with saturated aqueous NaCl, dried over MgSO$_4$, and filtered. The resulting filtrate was passed through a plug of silica gel and concentrated in vacuo, providing 12.1 g of the pure product.

b. Preparation of:

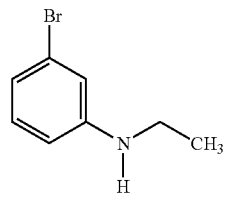

19(b)

A solution of compound 19(a) (17.29 g, 80.8 mmol) in tetrahydrofuran (100 ml) was added dropwise to LiAlH$_4$ (162 ml, 1M, 161.6 mmol), which was cooled to 0° C. under argon. The reaction was stirred at 0° C. for one hour, and then stirred at room temperature for 2.5 hours. The reaction vessel was placed in an ice-bath, and the reaction was quenched with the slow addition of water (6.4 ml), followed by the dropwise addition of 15% NaOH and an additional amount of water (19 ml). Potassium carbonate was added until the reaction became more free-flowing. The solids were removed via filtration and rinsed with tetrahydrofuran. The filtrate was concentrated to provide the product as a brown oil.

c. Preparation of:

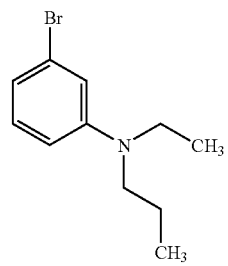

19(c)

A mixture of diisopropylethylamine (5.23 ml, 30 mmol) and 1-iodopropane (2.93 ml, 30 mmol) was added to a solution of compound 19(b) (2.0 g, 10.0 mmol) dissolved in acetonitrile (25 ml). The solution was allowed to reflux for 5 days. The reaction was cooled to room temperature, and the acetonitrile was removed in vacuo. The resulting solid was mixed with water (40 ml) and extracted into ethyl acetate. The organic layer was dried over MgSO$_4$ and concentrated in vacuo. The product was purified via flash chromatography, providing 2.16 g of the product.

d. Preparation of:

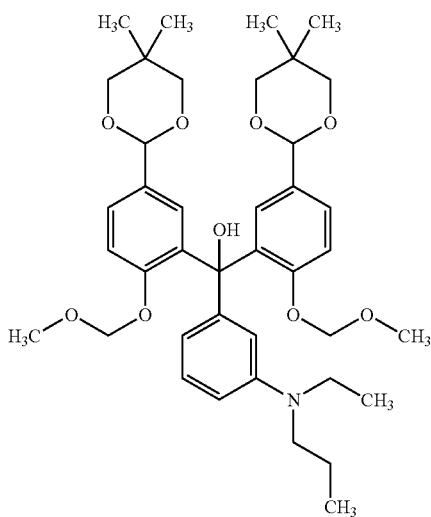

19(d)

Compound 19(c) (2.16 g, 8.92 mmol) was dissolved in tetrahydrofuran (30 ml) and cooled to −78° C., under argon. N-Butyllithium (4.05 ml, 10.12 mmol, 2.5M in hexanes) was added dropwise. The mixture was stirred at −78° C. for 15 to 25 minutes. Compound 16(b) (3.16 g, 5.95 mmol) in tetrahydrofuran (25 ml) was added dropwise to the reaction mixture. The resulting solution was stirred overnight while slowly warming to room temperature. The reaction was quenched with saturated aqueous $NH_4Cl$, extracted with ethyl acetate (2×30 ml), washed with saturated aqueous NaCl, dried over $MgSO_4$, and concentrated in vacuo. The product was purified via column chromatography (silica gel, 25% ethyl acetate in hexanes) to provide 2.9 g of the desired product.

e. Preparation of:

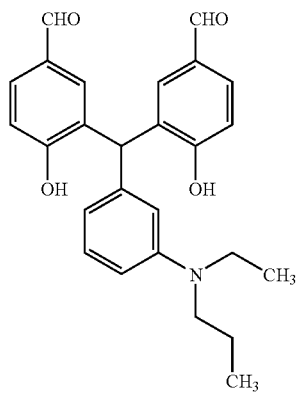

19(e)

Compound 19(d) (0.306 g, 0.441 mmol) was dissolved in acetic acid (10 ml) then treated with hydriodic acid (1.0 ml, 57 wt % in water). The reaction mixture was stirred 20 hours then treated with a saturated aqueous sodium sulfate solution (4 ml). A saturated aqueous sodium carbonate solution (80 ml) was slowly added until the reaction mixture reached pH=8.0, then the aqueous layer was extracted with ethyl acetate. The organic layers were concentrated in vacuo to give 0.25 g of the desired product as a light yellow solid.

f. 2,2'-[[3-(Ethylpropylamino)phenyl]methylene]bis[4-[[(5-methyl-1H-tetrazol-1-yl)imino]methyl]]phenol, tosylate salt. 1-Amino-5-methyltetrazole (0.18 g, 1.8 mmol) and pyridinium para-toluenesulfonate (0.17 g, 0.66 mmol) were dissolved in ethanol (10 ml) and brought to reflux temperature. Compound 19(e) (0.25 g, 0.60 mmol) was dissolved in ethanol (10 ml) and added to the refluxing solution. The reaction was maintained at refluxing temperature for two hours and stirred at room temperature overnight. The solution was concentrated in vacuo, and solid was precipitated with the addition of water. The desired product was isolated as a tosylate salt via filtration, rinsed with water (2×), and dried under vacuum.

g. 2,2'-[[3-Ethylpropylamino)phenyl]methylene]bis[4-[[(5-methyl-1H-tetrazol-1-yl)imino]methyl]]phenol. The tosylate salt from step f (0.18 g, 0.24 mmol) was added to a solution of sodium bicarbonate (40 mg, 0.48 mmol) in water (10 ml). Ethyl acetate (10 ml) was added, and the mixture was stirred and sonicated for 15 minutes. The layers were separated, and the aqueous layer was washed with ethyl acetate. The combined organics were washed with brine and concentrated. The remaining residue was recrystallized in a mixture of ethyl acetate and hexanes to provide 0.08 g of the product as a pink solid.

Example 20

Preparation of 2,2'-[[(3-Diethylamino)phenyl]methylene]bis[4-[[(5-methyl-1H-tetrazol-1-yl)imino]methyl]]phenol The title compound was prepared essentially according to the basic procedure described Example 19, above; however, ethyl iodide was used in step c instead of 1-iodopropane.

Example 21

Preparation of 2,2'-[[(3-Butylethylamino)phenyl]methylene]bis[4-[[(5-methyl-1H-tetrazol-1-yl)imino]methyl]]phenol The title compound was prepared essentially according to the basic procedure described Example 19, above; however, 1-iodobutane was used in step c instead of 1-iodopropane.

Example 22

Preparation of 2,2'-[[(3-Methylamino)phenyl]methylene]bis[4-[[(5-methyl-1H-tetrazol-1-yl)imino]methyl]]phenol a. Preparation of:

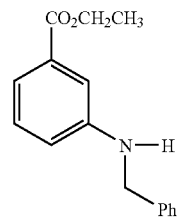

22(a)(i)

-continued

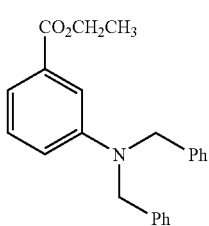

22(a)(ii)

(Ph = phenyl)

A mixture of ethyl 3-aminobenzoate (9.80 g, 59.3 mmol), benzyl chloride (20 mL, 0.17 mol) and potassium carbonate (38 g, 0.27 mol) in dry ethanol (100 mL) was heated at reflux for 124 h. The reaction mixture was concentrated in vacuo, diluted with 100 mL of water, and extracted with ethyl acetate. The organic layers were concentrated in vacuo, and the residue was purified via column chromatography (silica gel, 3% ethyl acetate in hexanes) to provide 5.0 g of compound 22(a)(i) as a white solid, along with 13.1 g of compound 22(a)(ii).

b. Preparation of:

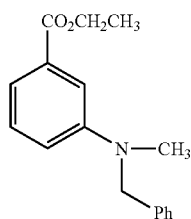

22(b)

Compound 22(a)(i) (2.70 g, 10.6 mmol), iodomethane (3.0 ml, 48 mmol), and potassium carbonate (6.6 g, 48 mmol) were placed in dry ethanol (40 ml) and stirred at reflux for 24 hours. The reaction mixture was concentrated in vacuo, and the residue was treated with water (50 ml) and extracted with ethyl acetate. The organic layers were concentrated in vacuo, and the crude sample was purified via column chromatography (silica gel, 5% ethyl acetate in hexanes) to provide 1.76 g of the desired product as clear oil.

c. Preparation of:

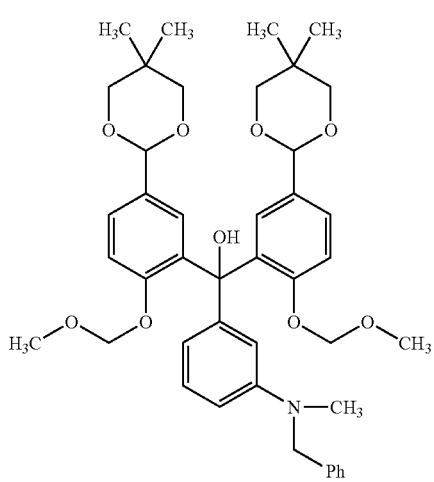

22(c)

Placed 2-(4-Methoxymethoxyphenyl)-5,5-dimethyl-1,3-dioxane (5.00 g, 19.8 mmol) and N,N,N',N'-tetramethylethylenediamine, prepared according to Example 1 step b, above, (3.0 ml, 19.9 mmol) in tetrahydrofuran (65 ml) at 0° C., then added sec-butyl lithium (17.3 ml, 1.3 M in cyclohexane). The deep red reaction mixture was stirred an additional 30 minutes at 0° C., then a solution of compound 22(b) (1.76 g, 6.53 mmol) in tetrahydrofuran (35 ml) was added dropwise over a 30 minute period. The reaction mixture was stirred an additional 90 minutes at 0° C., then quenched with a saturated aqueous mixture of ammonium chloride (7 ml). The reaction mixture was extracted with ethyl acetate, and the organic layers were concentrated in vacuo. The sample was purified via column chromatography (silica gel, 25% ethyl acetate in hexanes) to provide 3.58 g of the desired product as a white solid.

d. Preparation of:

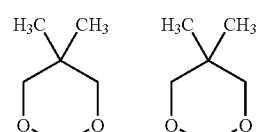

22(d)

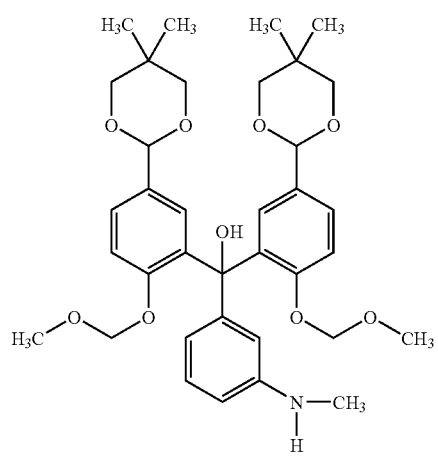

Compound 22(c) (3.58 g, 4.92 mmol) was dissolved in dry methanol (100 ml) with 10% palladium on carbon (0.5 g). The reaction mixture was placed under 55 psi of hydrogen gas and agitated for 16 hours. The mixture was filtered through Celite, rinsing the pad with methanol, and then the filtrate was concentrated in vacuo. The crude product was purified via column chromatography (silica gel, 25% ethyl acetate in hexanes) to provide 2.85 g of the desired product as a white solid.

e. Preparation of:

22(e)

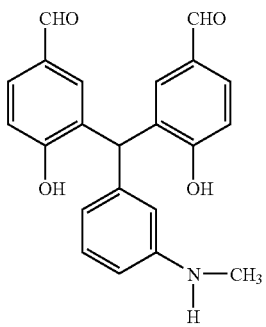

Hydriodic acid (1.5 ml, 57 wt % in water) was added to a solution of compound 22(d) (0.40 g, 0.627 mmol) in glacial acetic acid (20 ml). The reaction was stirred at room temperature for several hours. The reaction mixture was diluted with water and extracted with ethyl acetate. The combined organic layers were washed with saturated aqueous $NaHSO_3$ and brine, and rotary evaporated. The resulting solid was purified via flash chromatography (silica gel, ethyl acetate/hexanes gradient), resulting in 100 mg of the desired product.

f. 2,2'-[[(3-Methylamino)phenyl]methylene]bis[4-[[(5-methyl-1H-tetrazol-1-yl)imino]methyl]]phenol. A solution of compound 22(e) (90 mg, 0.249 mmol) in ethanol (7 ml) was added dropwise to a refluxing solution of 1-amino-5-methyltetrazole (74 mg, 0.747 mmol) and pyridinium para-toluenesulfonate (6 mg, 0.025 mmol) in ethanol (7 ml). The reaction was heated to reflux for 1.5 hours, and then cooled to room temperature overnight. The mixture was concentrated in vacuo until about 2 ml of ethanol remained. Water (6 ml) was added to the solution, and the mixture was sonicated. The solid was isolated via filtration and dried to provide 55 mg of the title compound.

Example 23

Preparation of 3-[[Bis[[5-(5-methyl-1H-tetrazol-1-yl)imino]methyl]-2-hydroxyphenyl]methylene]-N,N-diethylbenzenesulfonamide a. Preparation of:

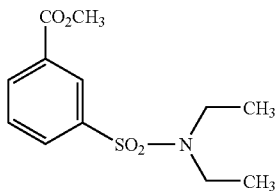

23(a)

A solution of 3-chlorosulfonylbenzoic acid (5.00 g, 22.7 mmol) in tetrahydrofuran (30 ml) was dropwise added to a solution of diethylamine (3.0 ml, 29 mmol) and triethylamine (3.8 ml, 27.2 mmol) in tetrahydrofuran (30 ml) over 40 min. The reaction mixture was stirred for 16 hours, and then concentrated in vacuo to a crude solid. The crude solid was stirred in 6N HCl (50 ml) for 1 hour then filtered and washed with 1N HCl. The solids were collected, dried, dissolved in dry methanol (100 ml) and treated with thionyl chloride (2 ml). The solution was refluxed for 4 hours then concentrated in vacuo to a crude solid, which was purified via column chromatography (silica gel, ethyl acetate/hexanes gradient) to provide 4.60 g of the desired product as a white solid.

b. Preparation of:

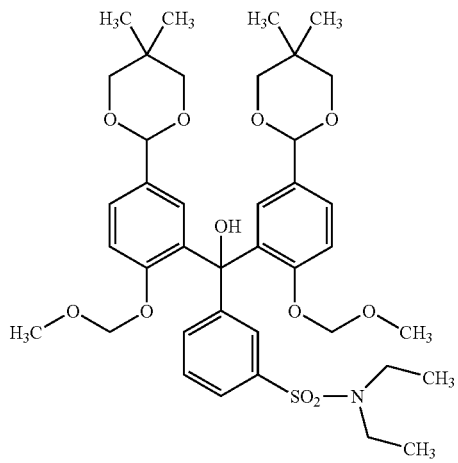

23(b)

2-(4-Methoxymethoxyphenyl)-5,5-dimethyl-1,3-dioxane, prepared according to Example 1 step b, above (6.56 g, 26.0 mmol), and N,N,N',N'-tetramethylethylenediamine (3.92 ml, 26.0 mmol) were placed in tetrahydrofuran (85 ml) at 0° C. Sec-butyl lithium (22.0 ml, 1.3 M in cyclohexane) was added to the mixture. The deep red reaction mixture was stirred an additional 30 minutes at 0° C., then a solution of compound 23(a)(2.35 g, 8.67 mmol) in tetrahydrofuran (35 ml) was added dropwise over a 30 minute period. The reaction mixture was stirred an additional 2 hours at 0° C., then quenched with a saturated aqueous mixture of ammonium chloride (5 ml). The reaction mixture was extracted with ethyl acetate, then the organic layers were concentrated in vacuo. The sample was purified via column chromatography (silica gel, ethyl acetate/hexanes gradient) to provide 4.40 g of the desired product as a light yellow solid.

c. Preparation of:

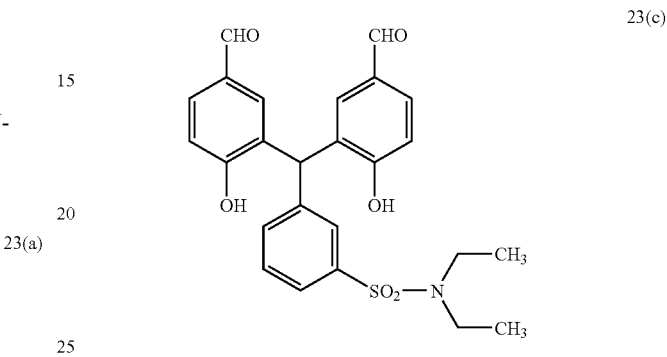

23(c)

Hydriodic acid (3.0 ml, 57 wt % in water) was added to a solution of compound 23(b) (2.50 g, 3.36 mmol) in glacial acetic acid (30 ml). The reaction was stirred at room temperature for 6 hours then poured into water and extracted with ethyl acetate. The combined organic layers were washed with saturated aqueous NaHSO$_3$, then brine, and concentrated by rotary evaporation. The crude solid was purified via flash chromatography (silica gel, ethyl acetate/hexanes gradient), resulting in 0.70 g of the desired product as a light yellow solid.

d. 3-[[Bis[[5-(5-methyl-1H-tetrazol-1-yl)imino]methyl]-2-hydroxyphenyl]methylene]-N,N-diethylbenzenesulfonamide. A solution of compound 23(c) (0.400 g, 0.856 mmol) in ethanol (12 ml) was dropwise added to a refluxing solution of 1-amino-5-methyltetrazole (0.25 g, 2.6 mmol) and pyridinium para-toluenesulfonate (22 mg, 0.088 mmol) in ethanol (12 ml). The reaction was heated to reflux for 2 hours, and then cooled to room temperature overnight. A white precipitate was filtered and washed with cold ethanol then dried under high vacuum to give 0.47 g of the desired product as a pale yellow solid.

Example 24

Preparation of 2,2'-[[3-(2-Dimethylaminoethoxy)phenyl]methylene]bis[4-[[(5-methyl-1H-tetrazol-1-yl)imino]methyl]]phenol a. Preparation of:

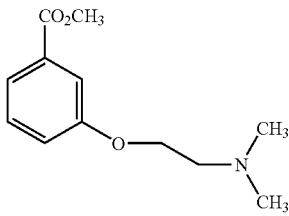

24(a)

A solution of methyl 3-hydroxybenzoate (4.50 g, 29.6 mmol), N,N-dimethylethanolamine (3.27 ml, 32.5 mmol)

and triphenylphosphine (9.31 g, 35.5 mmol) in tetrahydrofuran (75 ml) was treated with diethyl azodicarboxylate (7.00 ml, 44.4 mmol). An exothermic reaction caused the solution to reflux for 2 min then cooled to 22° C. The reaction mixture was stirred for 16 hours, then concentrated in vacuo. The residue was diluted with ethyl acetate and washed with water and brine. The organic layers were concentrated in vacuo, and the crude sample was purified via column chromatography (silica gel, methanol and dichloromethane gradient) to provide 2.77 g of the desired product as pale yellow oil.

b. Preparation of:

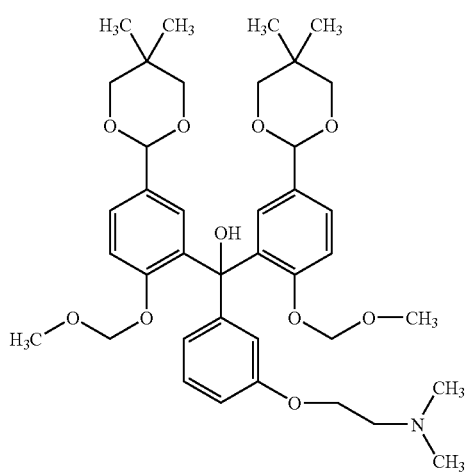

24(b)

A mixture of 2-(4-Methoxymethoxyphenyl)-5,5-dimethyl-1,3-dioxane (6.56 g, 26.0 mmol), prepared according to Example 1 step b, above, and N,N,N',N'-tetramethylethylenediamine (3.92 ml, 26.0 mmol) was mixed with tetrahydrofuran (85 ml) at 0° C. Sec-butyl lithium (22.0 ml, 1.3 M in cyclohexane) was added to the mixture. The deep red reaction mixture was stirred an additional 30 min at 0° C., then a solution of compound 24(a) (1.94 g, 8.67 mmol) in tetrahydrofuran (35 ml) was added dropwise over 30 min. The reaction mixture was stirred an additional 2 hours at 0° C., then quenched with a saturated aqueous mixture of ammonium chloride (5 ml). The reaction mixture was extracted with ethyl acetate, and the organic layers were concentrated in vacuo. The sample was purified via column chromatography (silica gel, methanol and dichloromethane gradient) to provide 6.56 g of the desired product as a white solid.

c. Preparation of:

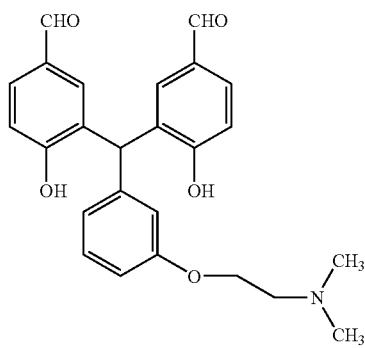

24(c)

Hydriodic acid (1.5 ml, 57 wt % in water) was added to a solution of compound 24(b) (0.75 g, 1.08 mmol) in glacial acetic acid (15 ml). The reaction was stirred at room temperature for 6 hours then poured into water and extracted with ethyl acetate. The combined organic layers were washed with saturated aqueous $NaHSO_3$, brine, and concentrated by rotary evaporation. The crude solid was purified via flash chromatography (silica gel, ethyl acetate/hexanes gradient), resulting in 400 mg of the desired product.

d. 2,2'-[[3-(2-Dimethylaminoethoxy)phenyl]methylene]bis[4-[[(5-methyl-1H-tetrazol-1-yl)imino]methyl]]phenol. A solution of compound 24(c) (0.40 g, 0.95 mmol) in ethanol (10 ml) was dropwise added to a refluxing solution of 1-amino-5-methyltetrazole (0.31 g, 3.1 mmol) and pyridinium para-toluenesulfonate (22 mg, 0.088 mmol) in ethanol (20 ml). The reaction was heated to reflux for 1.5 hours, and then cooled to room temperature overnight. The mixture was concentrated in vacuo until about 2 ml of ethanol remained. Water (6 ml) was added to the solution, and the mixture was sonicated for 10 minutes. The crude solid was, isolated via filtration and purified via column chromatography (silica gel, 20% methanol in ethyl acetate) to provide 0.215 g of the desired product as a white solid.

Example 25

Preparation of N-[[3-[Bis[[5-(5-methyl-1H-tetrazol-1-yl)imino]methyl]-2-hydroxylphenyl]methylene]phenyl]-2,2-dimethylpropanamide a. Preparation of:

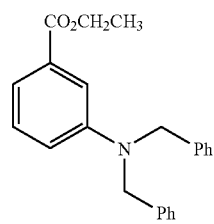

25(a)(I)

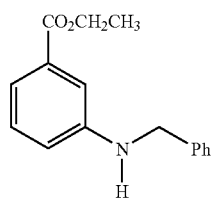

25(a)(ii)

(Ph = phenyl)

A solution of ethyl 4-aminobenzoate (9.80 g, 59.3 mmol), benzyl chloride (20 ml, 0.174 mol) and potassium carbonate (38 g, 0.27 mol) in dry ethanol (100 mL) was heated at reflux for 124 hours. The reaction mixture was concentrated in vacuo to a residue, diluted with 100 ml of water then extracted with ethyl acetate. The organic layers were concentrated in vacuo, and the crude sample was purified via column chromatography (silica gel, 3% ethyl acetate in hexanes) to provide 13.1 g of compound 25(a)(i) as a white solid along with 5.0 g of compound 25(a)(ii).

b. Preparation of:

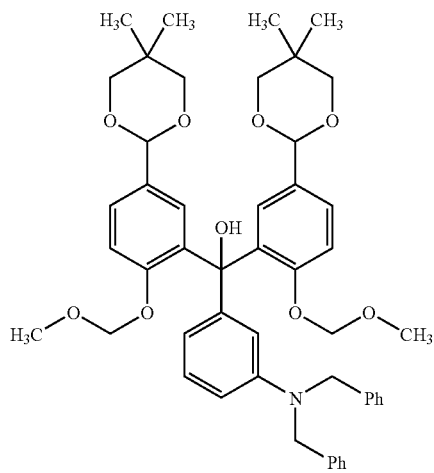

(Ph = phenyl)

Sec-butyl lithium (30.0 ml, 1.3 M in cyclohexane) was added to a mixture of 2-(4-methoxymethoxyphenyl)-5,5-dimethyl-1,3-dioxane, prepared according to Example 1 step b, above, (8.80 g, 34.9 mmol) and N,N,N',N'-tetramethylethylenediamine (5.3 ml, 35 mmol) mixed with tetrahydrofuran (100 ml) at 0° C. The deep red reaction mixture was stirred an additional 30 minutes at 0° C., then a solution of compound 25(a)(i) (4.0 g, 11.6 mmol) in tetrahydrofuran (40 ml) was added dropwise over 30 min. The reaction mixture was stirred an additional 2 hours at 0° C. then quenched with a saturated aqueous mixture of ammonium chloride (7 ml). The reaction mixture was extracted with ethyl acetate, then the organic layers were concentrated in vacuo. The sample was purified via column chromatography (silica gel, ethyl acetate/hexanes gradient) to provide 6.98 g of the desired product as a white solid.

c. Preparation of:

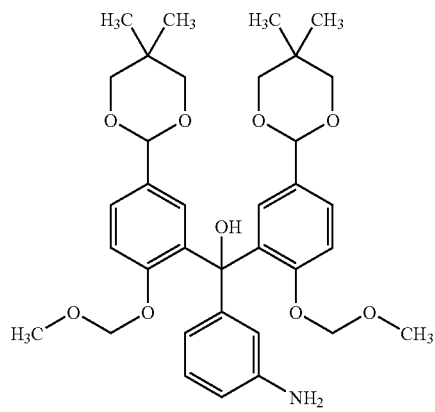

A mixture of compound 25(b) (2.40 g, 2.99 mmol) and 10% Palladium on carbon (0.24 g) in methanol (70 ml) was placed on a Parr-shaker apparatus with 55 psi of hydrogen gas and shaken for 4 hours. The solution was filtered through a pad of Celite and concentrated by rotary evaporation. The crude solid was purified via flash chromatography (silica gel, ethyl acetate/hexanes gradient), resulting in 1.56 g of the desired product as a white solid.

d. Preparation of:

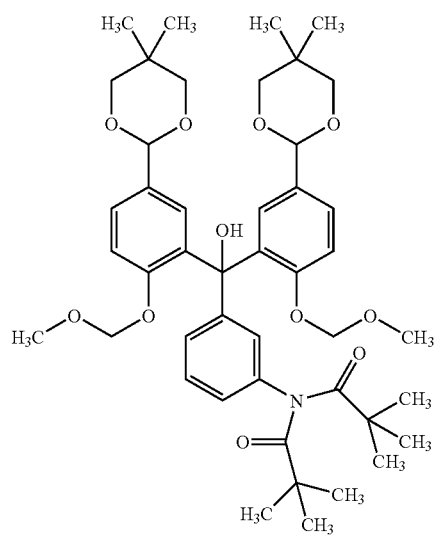

To a solution of compound 25(c) (0.300 g, 0.481 mmol) and diisopropylethylamine (0.30 ml, 1.7 mmol) was added trimethylacetyl chloride (0.30 ml, 2.4 mmol). The reaction mixture was stirred for 1 hour then concentrated in vacuo. The residue was diluted in ethyl acetate and washed with saturated NH$_4$Cl aqueous solution and brine, and concentrated by rotary evaporation. The crude solid was purified via flash chromatography (silica gel, ethyl acetate/hexanes gradient), resulting in 360 mg of the desired product as a tan solid.

e. Preparation of:

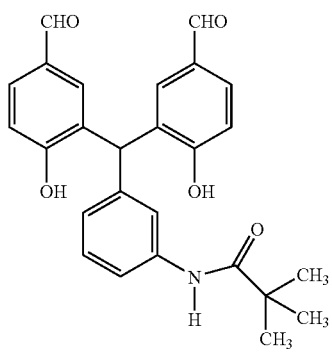

Hydriodic acid (1.0 ml, 57 wt % in water) was added to a solution of compound 25(d) (0.36 g, 0.46 mmol) in glacial acetic acid (15 ml). The reaction was stirred at room temperature for 6 hours then poured into water and extracted with ethyl acetate. The combined organic layers were washed with saturated aqueous NaHSO$_3$, then brine, and concentrated by rotary evaporation. The crude solid was purified via flash chromatography (silica gel, ethyl acetate/hexanes gradient), resulting in 200 mg of the desired product as a tan solid.

f. N-[3-[[Bis[[5-(5-methyl-1H-tetrazol-1-yl)imino]methyl]-2-hydroxylphenyl]methylene]phenyl]-2,2-dimethyl-propanamide. A solution of compound 25(e) (0.15 g, 0.35 mmol) in ethanol (5 ml) was dropwise added to a refluxing solution of 1-amino-5-methyltetrazole (0.10 g, 1.0 mmol) and pyridinium para-toluenesulfonate (9.0 mg, 0.035 mmol) in ethanol (5 ml). The reaction was heated at reflux for 2 hours, and then cooled to room temperature overnight. The mixture was concentrated in vacuo, and the crude solid was sonicated in ethanol then filtered and rinsed with ethanol. The sample was recrystallized with ethanol to give 0.11 g of the desired product as a white solid.

Example 26

Preparation of N-[[3-[Bis[[5-(5-methyl-1H-tetrazol-1-yl)imino]methyl]-2-hydroxylphenyl]methylene]phenyl]butanesulfonamide a. Preparation of:

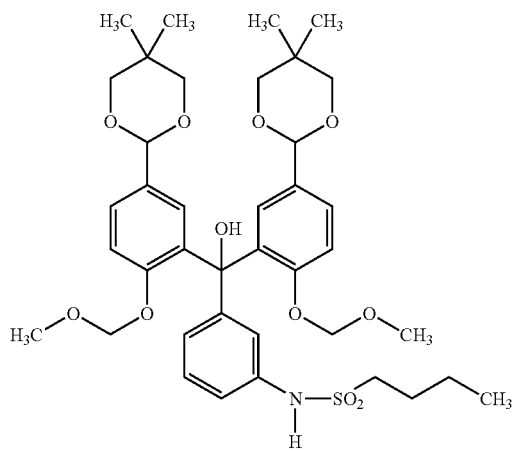

26(a)

To a solution of compound 25(c) (0.660 g, 1.06 mmol) and triethylamine (0.30 ml, 2.2 mmol) in dichloromethane (20 ml) was added 1-butanesulfonyl chloride (0.225 ml, 1.74 mmol). The reaction mixture was stirred for 3 hours then concentrated in vacuo to a paste. The residue was diluted with ethyl acetate and washed with water and brine. The combined organic layers were concentrated by rotary evaporation, and the resulting solid was purified via flash chromatography (silica gel, ethyl acetate/hexanes gradient), resulting in 0.61 g of the desired product as a white solid.

b. Preparation of:

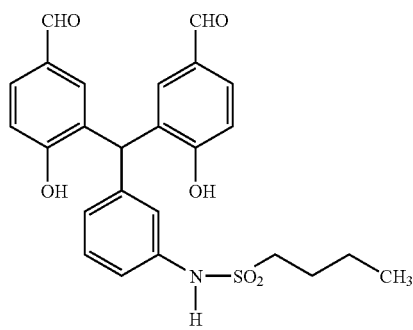

26(b)

Hydriodic acid (1.0 ml, 57 wt % in water) was added to a solution of compound 26(a) (0.60 g, 0.81 mmol) in glacial acetic acid (8 ml). The reaction was stirred at room temperature for 6 hours then poured into water and extracted with ethyl acetate. The combined organic layers were washed with saturated aqueous $NaHSO_3$ and brine and concentrated by rotary evaporation. The crude solid was purified via flash chromatography (silica gel, ethyl acetate/hexanes gradient), resulting in 0.17 g of the desired product as a light yellow solid.

c. N-[[3-[Bis[[5-(5-methyl-1H-tetrazol-1-yl)imino]methyl]-2-hydroxylphenyl]methylene]phenyl]butanesulfonamide. A solution of compound 26(b) (0.158 g, 0.338 mmol) in ethanol (7 ml) was dropwise added to a refluxing solution of 1-amino-5-methyltetrazole (0.100 g, 1.01 mmol) and pyridinium para-toluenesulfonate (9.0 mg, 0.035 mmol) in ethanol (7 ml). The reaction was heated to reflux for 2 hours, and then cooled to room temperature overnight. The reaction mixture was concentrated in vacuo down to 3 ml resulting in the formation of a white precipitate. The solids were filtered and washed with cold ethanol then dried to give 0.18 g of the desired product as a pale yellow solid.

Example 27

Preparation of 2,2'-[(3-Nitrophenyl)methylene]bis[4-[[(5-methyl-1H-tetrazol-1-yl)imino]methyl]]phenol a. Preparation of:

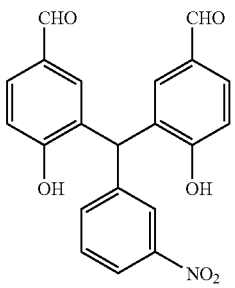

27(a)

3-Nitrobenzaldehyde (2.99 g, 19.8 mmol), 4-hydroxbenzaldehyde (6.10 g, 50 mmol), and concentrated hydrochloric acid (8.2 ml, 99 mmol) were sealed in a Carius tube and heated to 135° C. for several hours. The vessel was cooled to room temperature, and the solid material was washed with water, which was then decanted. The material was dissolved in N,N-dimethylformamide, and a precipitate formed upon addition of water. The solid was isolated by filtration, and purified via column chromatography (silica gel, 50% ethyl acetate in hexanes), providing 0.299 g (4%) of the desired product.

b. 2,2'-[(3-Nitrophenyl)methylene]bis[4-[[(5-methyl-1H-tetrazol-1-yl)imino]methyl]]phenol. The title compound was obtained essentially according to step f, in Example 1, above; however compound 27(a) was used instead of compound 1(e).

Example 28

Preparation of 2,2'-[(3-Methylthiophenyl)methylene]bis[4-[[(5-methyl-1H-tetrazol-1-yl)imino]methyl]]phenol a. Preparation of:

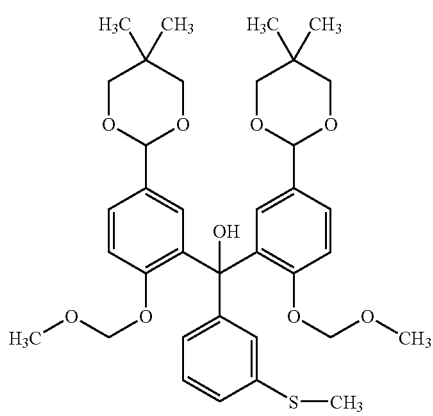

28(a)

3-Bromothioanisole (0.71 g, 3.5 mmol) was dissolved in diethylether (30 ml) and cooled to −15° C., under argon. N-Butyllithium (1.5 ml, 3.8 mmol, 2.5M in hexanes) was added dropwise. The mixture was stirred at −15° C. for 3 hours. Compound 16(b) (1.5 g, 2.8 mmol) in diethylether (15 ml) was added dropwise to the reaction mixture. The resulting solution was stirred overnight while slowly warming to room temperature. The reaction was quenched with saturated aqueous NH$_4$Cl, extracted with ethyl acetate (2×30 ml), washed with saturated aqueous NaCl, dried over MgSO$_4$, and concentrated in vacuo. The product was purified via column chromatography (silica gel, 20% ethyl acetate in hexanes) to provide 0.48 g of the desired product.

b. Preparation of:

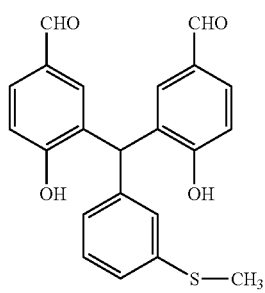

28(b)

Hydriodic acid (0.7 ml, 58 wt % in water) was added to a solution of compound 28(a) (0.46 g, 0.7 mmol) in glacial acetic acid (7 ml). The reaction was stirred at room temperature for 2 hours. The acetic acid was removed in vacuo, and the residue was dissolved in water and ethyl acetate. The organic layer was washed with 10% aqueous sodium thiosulfate and saturated aqueous NaCl solution. The organics were dried over magnesium sulfate, filtered, and rotary evaporated. The product was purified via column chromatography (silica gel) to provide 0.25 g of the desired product.

c. 2,2'-[(3-Methylthiophenyl)methylene]bis[4-[[(5-methyl-1H-tetrazol-1-yl)imino]methyl]]phenol. Compound 28(b) (0.05 g, 0.13 mmol) was dissolved in 2 ml of absolute ethanol, and added dropwise to a refluxing solution of 1-amino-5-methyltetrazole (0.04 g, 0.40 mmol) and pyridinium para-toluenesulfonate (0.003 g, 0.013 mmol) in 2 ml ethanol, under argon. The reaction was heated to reflux for 2 hours, and then cooled to room temperature. A solid was collected by filtration and dried under vacuum, yielding about 0.042 g of the title product.

Example 29

Preparation of 2,2'-[(3-Methylsulfinylphenyl)methylene]bis[4-[[(5-methyl-1H-tetrazol-1-yl)imino]methyl]]phenol a. Preparation of:

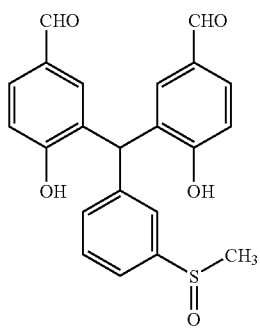

29(a)

NaIO$_4$ (0.073 g, 0.34 mmol) was added to a solution of compound 28(b) (0.13 g, 0.34 mmol) dissolved in ethanol (12 ml) and water (12 ml). The reaction was stirred at room temperature for 5 hours. The solvents were removed in vacuo. The residue was dissolved in ethyl acetate and washed with water (2×10 ml). The organics were dried over magnesium sulfate, filtered, and rotary evaporated to yield 0.12 g of the desired product.

b. 2,2'-[(3-Methylsulfinylphenyl)methylene]bis[4-[[(5-methyl-1H-tetrazol-1-yl)imino]methyl]]phenol. Compound 29(a) (0.075 g, 0.19 mmol) was dissolved in absolute ethanol (4 ml), and added dropwise to a refluxing solution of 1-amino-5-methyltetrazole (0.057 g, 0.57 mmol) and pyridinium para-toluenesulfonate (0.005 g, 0.019 mmol) in 2.5 ml of ethanol, under argon. The reaction was heated to reflux for 2 hours, and then cooled to room temperature. The solvent was removed in vacuo. The residue was suspended in water, collected by filtration, and dried by vacuum to yield 0.096 g of the title product.

Example 30

Preparation of 2,2'-[(3-Methylsulfinylphenyl)methylene]bis[4-[[(5-methyl-1H-tetrazol-1-yl)imino]methyl]]phenol a. Preparation of:

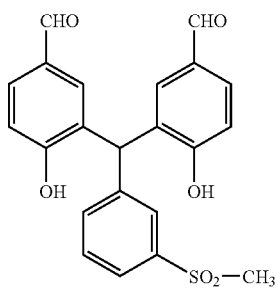

30(a)

Compound 29(a) (0.036 g, 0.09 mmol) was dissolved in ethanol (2 ml) and water (2 ml) then cooled to 0° C. Meta-chloroperbenzoic acid (0.017 g, 0.09 mmol) was added to the solution. The reaction mixture was stirred at room temperature overnight. The solvents were removed in vacuo. The residue was dissolved in ethyl acetate (50 ml) and washed with saturated aqueous NaCl solution and 5% $NaHCO_3$ solution. The organics were dried over magnesium sulfate, filtered, and rotary evaporated to yield 0.024 g of the desired product.

f. 2,2'-[(3-Methylsulfonylphenyl)methylene]bis[4-[[(5-methyl-1H-tetrazol-1-yl)imino]methyl]]phenol. Compound 30(a) (0.024 g, 0.058 mmol), 1-amino-5-methyltetrazole (0.017 g, 0.17 mmol) and pyridinium para-toluenesulfonate (0.002 g, 0.006 mmol) were dissolved in 3 ml absolute ethanol under argon and refluxed for 2 hours. The reaction was cooled to room temperature. A solid was collected by filtration and dried under vacuum, yielding about 0.015 g of the title product.

Other compounds of the invention having anti-pneumovirus activity may be prepared following the various synthetic routes described hereinabove. Examples include, without limitation the compounds of Table 1:

TABLE 1

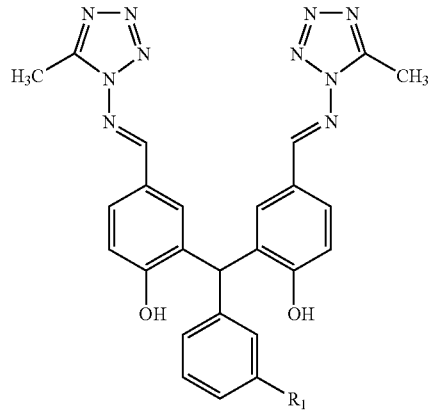

| Example Number | $R_1$ | Name |
|---|---|---|
| 1. | —$CH_2CH_2CH_3$ | 2,2'-[(3-Propylphenyl)methylene]bis[4-[[(5-methyl-1H-tetrazol-1-yl)imino]methyl]]phenol |
| 2. | —N(CH$_3$)(CH$_3$) | 2,2'-[[(3-Dimethylamino)phenyl]methylene]bis[4-[[(5-methyl-1H-tetrazol-1-yl)imino]methyl]]phenol |
| 3. | —CH(CH$_3$)(CH$_3$) | 2,2'-[[3-Methylethyl)phenyl]methylene]bis[4-[[(5-methyl-1H-tetrazol-1-yl)imino]methyl]]phenol |
| 4. | —$CH_3$ | 2,2'-[(3-Methylphenyl)methylene]bis[4-[[(5-methyl-1H-tetrazol-1-yl)imino]methyl]]phenol |
| 5. | —$OCH_3$ | 2,2'-[(3-Methoxyphenyl)methylene]bis[4-[[(5-methyl-1H-tetrazol-1-yl)imino]methyl]]phenol |
| 6. | —$OCH_2CH_3$ | 2,2'-[(3-Ethoxyphenyl)methylene]bis[4-[[(5-methyl-1H-tetrazol-1-yl)imino]methyl]]phenol |
| 7. | —Cl | 2,2'-[(3-Chlorophenyl)methylene]bis[4-[[(5-methyl-1H-tetrazol-1-yl)imino]methyl]]phenol |
| 8. | —Br | 2,2'-[(3-Bromophenyl)methylene]bis[4-[[(5-methyl-1H-tetrazol-1-yl)imino]methyl]]phenol |

TABLE 1-continued

| | | |
|---|---|---|
| 9. | 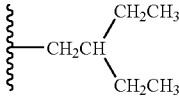 -CH₂CH(CH₂CH₃)CH₂CH₃ | 2,2'-[[3-(2-Ethylbutyl)phenyl]methylene]bis[4-[[(5-methyl-1H-tetrazol-1-yl)imino]methyl]]phenol |
| 10. | 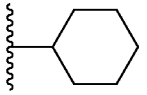 cyclohexyl | 2,2'-[[3-Cyclohexyl)phenyl]methylene]bis[4-[[(5-methyl-1H-tetrazol-1-yl)imino]methyl]]phenol |
| 11. | —CH₂CH₂CH₂CH₃ | 2,2'-[(3-Butylphenyl)methylene]bis[4-[[(5-methyl-1H-tetrazol-1-yl)imino]methyl]]phenol |
| 12. | —F | 2,2'-[(3-Fluorophenyl)methylene]bis[4-[[(5-methyl-1H-tetrazol-1-yl)imino]methyl]]phenol |
| 13. | —CH₂CH₂CH₂CH₂CH₃ | 2,2'-[(3-Pentylphenyl)methylene]bis[4-[[(5-methyl-1H-tetrazol-1-yl)imino]methyl]]phenol |
| 14. | 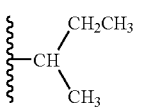 -CH(CH₂CH₃)CH₃ | 2,2'-[[3-(1-Methylpropyl)phenyl]methylene]bis[4-[[(5-methyl-1H-tetrazol-1-yl)imino]methyl]]phenol |
| 15. | 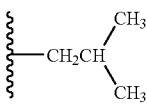 -CH₂CH(CH₃)CH₃ | 2,2'-[[3-(2-Methylpropyl)phenyl]methylene]bis[4-[[(5-methyl-1H-tetrazol-1-yl)imino]methyl]]phenol |
| 16. | —CH₂CH₂OCH₃ | 2,2'-[[(3-Methoxyehtyl)phenyl]methylene]bis[4-[[(5-methyl-1H-tetrazol-1-yl)imino]methyl]]phenol |
| 17. | —CH₂CH₃ | 2,2'-[(3-Ethylphenyl)methylene]bis[4-[[(5-methyl-1H-tetrazol-1-yl)imino]methyl]]phenol |
| 18. | 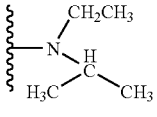 -N(CH₂CH₃)CH(CH₃)CH₃ | 2,2'-[[[3-Ethyl(methylethyl)amino]phenyl]methylene]bis[4-[[(5-methyl-1H-tetrazol-1-yl)imino]methyl]]phenol |
| 19. | 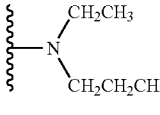 -N(CH₂CH₃)CH₂CH₂CH₃ | 2,2'-[[(3-Ethylpropylamino)phenyl]methylene]bis[4-[[(5-methyl-1H-tetrazol-1-yl)imino]methyl]]phenol |
| 20. | 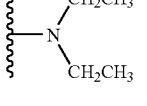 -N(CH₂CH₃)CH₂CH₃ | 2,2'-[[(3-Diethylamino)phenyl]methylene]bis[4-[[(5-methyl-1H-tetrazol-1-yl)imino]methyl]]phenol |
| 21. | 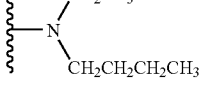 -N(CH₂CH₃)CH₂CH₂CH₂CH₃ | 2,2'-[[(3-Butylethylamino)phenyl]methylene]bis[4-[[(5-methyl-1H-tetrazol-1-yl)imino]methyl]]phenol |
| 22. | —NHCH₃ | 2,2'-[[(3-Methylamino)phenyl]methylene]bis[4-[[(5-methyl-1H-tetrazol-1-yl)imino]methyl]]phenol |
| 23. | 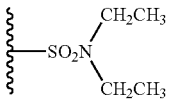 -SO₂N(CH₂CH₃)CH₂CH₃ | 3-[[Bis[[5-(5-methyl-1H-tetrazol-1-yl)imino]methyl]-2-hydroxyphenyl]methylene]-N,N-diethylbenzenesulfonamide |
| 24. | 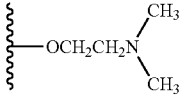 -OCH₂CH₂N(CH₃)CH₃ | 2,2'-[[3-(2-Dimethylaminoethoxy)phenyl]methylene]bis[4-[[(5-methyl-1H-tetrazol-1-yl)imino]methyl]]phenol |
| 25. | 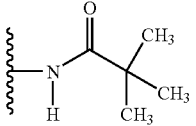 -NHC(O)C(CH₃)₃ | N-[[3-[Bis[[5-(5-methyl-1H-tetrazol-1-yl)imino]methyl]-2-hydroxyphenyl]methylene]phenyl]-2,2-dimethylpropanamide |

TABLE 1-continued

| 26. | [structure: -N(H)-SO₂CH₂CH₂CH₂CH₃] | N-[[3-[Bis[[5-(5-methyl-1H-tetrazol-1-yl)imino]methyl]-2-hydroxyphenyl]methylene]phenyl]butanesulfonamide |
| --- | --- | --- |
| 27. | —NO₂ | 2,2'-[(3-Nitrophenyl)methylene]bis[4-[[(5-methyl-1H-tetrazol-1-yl)imino]methyl]]phenol |
| 28. | [structure: -S-CH₃] | 2,2'-[(3-Methylthiophenyl)methylene]bis[4-[[(5-methyl-1H-tetrazol-1-yl)imino]methyl]]phenol |
| 29. | [structure: -S(=O)-CH₃] | 2,2'-[(3-Methylsulfinylphenyl)methylene]bis[4-[[(5-methyl-1H-tetrazol-1-yl)imino]methyl]]phenol |
| 30. | [structure: -SO₂CH₃] | 2,2'-[(3-Methylsulfonylphenyl)methylene]bis[4-[[(5-methyl-1H-tetrazol-1-yl)imino]methyl]]phenol |
| 31. | [structure: -SO₂N(CH₃)₂] | 3-[[Bis[[5-(5-methyl-1H-tetrazol-1-yl)imino]methyl]-2-hydroxyphenyl]methylene]-N,N-dimethylbenzenesulfonamide |
| 32. | —NHCH₂CH₂CH₃ | 2,2'-[(3-Propylaminophenyl)methylene]bis[4-[[(5-methyl-1H-tetrazol-1-yl)imino]methyl]]phenol |
| 33. | [structure: -OCH₂CH₂CH₂N(CH₂CH₃)₂] | 2,2'-[[3-[2-Dimethylaminopropoxy)phenyl]methylene]bis[4-[[(5-methyl-1H-tetrazol-1-yl)imino]methyl]]phenol |
| 34. | [structure: -N(H)-C(=O)CH₃] | N-[[3-[Bis[[5-(5-methyl-1H-tetrazol-1-yl)imino]methyl]-2-hydroxyphenyl]methylene]phenyl]acetamide |
| 35. | [structure: -N(CH₂CH₂CH₃)-C(=O)CH₃] | N-[[3-[Bis[[5-(5-methyl-1H-tetrazol-1-yl)imino]methyl]-2-hydroxyphenyl]methylene]phenyl]-N-propylacetamide |
| 36. | [structure: -N(CH(CH₃)₂)-C(=O)CH₃] | N-[[3-[Bis[[5-(5-methyl-1H-tetrazol-1-yl)imino]methyl]-2-hydroxyphenyl]methylene]phenyl]-N-(methylethyl)acetamide |
| 37. | [structure: -N(CH₂CH₂CH₃)-C(=O)CH₂CH(CH₃)₂] | N-[[3-[Bis[[5-(5-methyl-1H-tetrazol-1-yl)imino]methyl]-2-hydroxyphenyl]methylene]phenyl]-3-methyl-N-propylbutanamide |

TABLE 1-continued

| | | |
|---|---|---|
| 38. | [structure: N-acyl with isobutyryl and isopropyl groups] | N-[[3-[Bis[[5-(5-methyl-1H-tetrazol-1-yl)imino]methyl]-2-hydroxyphenyl]methylene]phenyl]-3-methyl-N-(methylethyl)butanamide |
| 39. | [structure: N-methyl-N-isobutyrylamide] | N-[[3-[Bis[[5-(5-methyl-1H-tetrazol-1-yl)imino]methyl]-2-hydroxyphenyl]methylene]phenyl]-3-methyl-N-methylbutanamide |
| 40. | [structure: N-ethyl-N-acetyl] | N-[[3-[Bis[[5-(5-methyl-1H-tetrazol-1-yl)imino]methyl]-2-hydroxyphenyl]methylene]phenyl]-N-ethylacetamide |
| 41. | [structure: N-H sulfonamide with SO$_2$CH$_2$CH$_2$CH$_3$] | N-[[3-[Bis[[5-(5-methyl-1H-tetrazol-1-yl)imino]methyl]-2-hydroxyphenyl]methylene]phenyl]propanesulfonamide |
| 42. | [structure: N-methyl-N-isopropyl amine] | 2,2'-[[3-Methyl(methylethyl)aminophenyl]methylene]bis[4-[[(5-methyl-1H-tetrazol-1-yl)imino]methyl]]phenyol |

| Example Number | NMR Data* | Mass Spec. |
|---|---|---|
| 1. | $^1$H NMR in DMSO 10.51(s, 2H); 9.15(s, 2H); 7.79(dd, 2H, J=1.76, 8.21 Hz); 7.47(d, 2H, J=2.34 Hz); 7.23(t, 1H, J=7.62 Hz); 7.06(d, 1H, J=7.62 Hz); 6.99(d, 2H, J=8.21 Hz); 6.92(m, 2H); 6.06(s, 1H): 2.49(m, 2H); 2.46(s. 6H), 1.54(m, 2H); 0.85(t, 3H, J=7.62 Hz) | 535 |
| 2. | $^1$H NMR in DMSO 10.48(s, 2H); 9.15(s, 2H); 7.78(dd, 2H, J=2.38, 8.5 Hz); 7.51(2H, d, J=2.3 Hz); 7.12(t, 1H, J=8.2, 7.6 Hz); 6.98(d, 2H, J=8.79 Hz); 6.59(dd, 1H, J=1.76, 5.86 Hz); 6.47(1H, s); 6.38(6, 1H, J=7.62 Hz); 6.01(1H, s); 2.82(6H, s); 2.47(6H, s) | 537.93 (M + H)+ |
| 3. | $^1$H NMR in DMSO-d6; 10.497(s, 2H); 9.132(s, 2H); 7.774(dd, 2H, J=8.2, 1.75 Hz); 7.447(d, 2H, J=1.75 Hz); 7.220(t, 1H, J=7.62 Hz); 7.097(d, 1H, J=8.21 Hz); 6.993(obscured, 1H); 6.979(d, 2H, J=8.2 Hz); 6.903(d, 1H, J=7.62 Hz); 6.067(s, 1H); 2.804(septet, 1H, J=7.04 Hz); 2.434(s, 6H); 1.136(d, 6H, J=7.04 Hz) $^{13}$C in DMSO-d6; 159.956, 158.841, 149.200, 148.367, 142.123, 131.021, 130.918, 129.970, 128.264, 127.303, 126.700, 123.957, 122.162, 115.829, 42.920, 33.433, 23.921, 8.024 | 536 |
| 4. | — | 508 |
| 5. | $^1$H NMR in DMSO: 10.524(s, 2H); 9.155(s, 2H); 7.822(dd, 2H); 7.478(cm, 2H); 7.246(t, 1H); 7.996(cm. 2H); 6.825(cm, 1H); 6.679 (cm, 1H); 6.616(s, 1H); 6.052(s, 1H); 3.693(s, 3H); 2.467(s, 6H) | 523 |
| 6. | $^1$H NMR in DMSO: 10.52(s, 2H); 9.16(s, 2H); 7.79(6, 2H, J=8.21 Hz); 7.48 s, 2H), 7.22(t, 1H, J=7.62 Hz); 7.07(d, 2H, J=8.21 Hz); 6.80(6, 1H, J=7.62 Hz); 6.67(d, 1H, J=7.62 Hz); 6.57(s, 1H); 6.04(s, 1H); 3.95(q, 2H, J=6.45 Hz); 2.47(s, 6H); 1.27(t, 3H, J=6.45 Hz) | 539 |
| 7. | — | — |

TABLE 1-continued

| | | |
|---|---|---|
| 8. | ¹H NMR in DMSO-d6<br>10.608(s, 2H); 9.180(s, 2H); 7.834(dd, 2H, J=8.21, 2.35 Hz); 7.476(d, 2H, J=2.35 Hz); 7.440(complex, 1H); 7.303(t, 1H, J=7.62 Hz); 7.227(complex, 1H); 7.132(d, 1H, J=7.62 HZ); 7.015(d, 2H, J=8.21 Hz); 6.059(s, 1H); 3.3(s, 2H); 2.477(s, 6H)<br>¹³C NMR:<br>159.738, 158.712, 149.213, 145.213, 131.405, 131.111, 130.457, 129.893, 129.841, 129.200, 128.226, 122.277, 121.675, 115.944, 42.702, 8.049 | 573 |
| 9. | ¹H-NMR(300 MHz, DMSO)<br>10.52(s, 2H), 9.13(s, 2H), 7.80(dd, J=1.76, 8.35, 2H); 7.43(d, J=1.76, 2H); 7.22(T, J=7.91, 7.47, 1H); 7.03(d, J=7.91, 1H); 6.99(d, J=8.35, 2H); 6.90(s, 1H); 6.86(d, J=7.47, 1H); 6.05(s, 1H); 2.45-2.42(m, 8H); 1.46-1.40 (m, 1H); 1.19(d, J=7.47, 4H); 0.75(T, J=7.47, 6H)<br>¹³C-NMR(75.0 MHz, DMSO)<br>159.86, 158.87, 149.12, 141.90, 140.92, 130.95, 130.86, 129.84, 127.99, 126.83, 126.24, 122.02, 115.74, 42.67, 41.80, 24.37, 10.53, 7.99 | 579 |
| 10. | ¹H -NMR(300 MHz, DMSO)<br>10.51(s, 2H); 9.12(s, 2H); 7.79(dd, J=1.76, 8.35, 2H); 7.50(d, J=2.20, 2H); 7.23(T, J=7.91, 7.47, 1H); 7.10 (d, J=7.47, 1H); 6.99(d, J=8.35, 2H); 6.98(m, 1H); 6.92(d, J=7.47, 1H); 6.06(s, 1H); 2.46-2.43(m, 7H); 1.76-1.64(m, 5H); 1.41-1.20(m, 5H)<br>¹³C-NMR(75.0 MHz, DMSO)<br>159.82, 158.87, 149.12, 147.44, 141.99, 130.89, 130.74, 130.01, 128.21, 127.50, 126.69, 124.28, 122.04, 115.74, 43.72, 42.81, 40.33, 38.67, 34.02, 26.20, 25.48, 7.98 | 577 |
| 11. | ¹HNMR(300 MHz, DMSO);<br>10.55(s, 2H); 9.15(s, 2H); 7.82(dd, 2H, J=10.5); 7.47(s, 2H); 7.23(t, 1H, J=7.6); 7.08-6.88(m, 3H); 7.00(d, 2H, J=8.2); 6.06(s, 1H); 2.68(t, 2H, J=15.2); 2.46(s, 6H); 1.55-1.45(m, 2H); 1.32-1.20(m, 2H); 0.84(t, 3H, J=14.6)<br>¹³C NMR(75 MHz, DMSO)<br>160.56, 159.57, 149.85, 142.89, 142.77, 131.66, 131.58, 130.59, 129.78, 128.85, 127.10, 122.79, 116.48, 43.46, 35.48, 33.87, 22.32, 14.34, 8.74 | 550 |
| 12. | ¹HNMR(300 MHz, DMSO)<br>10.59(s, 2H); 9.26(s, 2H); 7.85(d, 2H, J=1.8); 7.48(s, 2H); 7.41-6.87(m, 6H); 6.09(s, 1H); 2.47(s, 6H) | 511 |
| 13. | ¹H NMR(300 MHz, DMSO)<br>10.56(s, 2H); 9.16(s, 2H); 7.82(dd, 2H, J=2, 10); 7.46(d 2H, J=2); 7.26(t, 1H, J=15); 7.08(d, 1H, J=7); 7.01(d, 2H, J=7); 6.93-6.87(m, 2H); 6.05(s, 1H); 2.54(t, 2H, J=10); 1.58-1.49(m, 2H); 1.23-1.20(m, 4H); 0.79(t, 3H, J=13) | 565 |
| 14. | ¹H NMR(300 MHz, DMSO)<br>10.54(s, 2H); 9.16(s, 2H); 7.83(d, 2H, J=7); 7.49(s, 2H); 7.25(t, 1H, J=8); 7.08=6.90(m, 3H); 7.03(d, 2H, J=8); 6.09(s, 1H); 2.56=2.52(m, 1H); 1.59-1.48(m, 2H); 1.28 (d, 3H, J=7); 0.88(t, 3H, J=16)<br>¹³C NMR(75 MHz, DMSO)<br>160.56, 159.57, 149.84, 142.89, 142.77, 131.67, 131.58, 130.57, 129.78, 128.85, 127.10, 122.79, 116.48, 43.45, 35.49, 33.87, 22.33, 14.36, 8.74 | 550 |
| 15. | ¹H(DMSO)<br>10.52(s, 2H); 9.14(s, 2H); 7.79(dd, 2H, J=2.34, 8.21 Hz); 7.45(d, 2H, J=1.76 Hz); 7.23(t, 1H, J=7.10 Hz); 7.01(m, 3H); 6.89(m, 2H); 6.05(s, 1H); 2.45(s, 6H); 2.39(d, 2H, J=7.03 Hz); 1.75(m, 1H); 0.81(d, 6H, J=6.45 Hz) | 549 |
| 16. | ¹H DMSO<br>10.52(s, 2H); 9.15(s, 2H); 7.80(dd, J=1.8, 2.3, 8.5 Hz, 2H); 7.47(d, J=23 Hz, 2H); 7.23(t, J=7.0, 7.6 Hz. 1H); .11(d, J=7.6 Hz, 1H); 7.00(sn, 3H); 6.93(d, J=7.6 Hz, 1H); 6.06(s, 1H); 3.49(t, 7.0, 6.4 Hz, 2H); 3.18(s, 3H); 2.76(t, 2H); 2.46(s, 6H) | 553 |
| 17. | — | 522 |
| 18. | ¹H-NMR(DMSO)<br>10.49(s, 2H); 9.16(s, 2H); 7.77(d, 2H, J=8.21 Hz); 7.55 (s, 2H); 7.09(t, 1H, J=7.62 Hz); 6.98(d, 2H, J=8.21 Hz); 6.60(d, 1H, J=8.21 Hz); 6.46(s, 1H); 6.34(d, 1H, J=7.62 Hz); 6.00(s, 1H); 3.95(m, 1H); 3.12(m, 2H); 2.46(s, 6H); 1.07(d, 6H, J=6.45 Hz) | 578 |

TABLE 1-continued

| | | |
|---|---|---|
| 19. | ¹H NMR(300 MHz, DMSO)<br>10.49(brs, 2H); 9.15(s, 2H); 7.78(dd, 2H, J=8.21, 1.76); 7.55(d, 2H, J=1.76); 7.07(t, 1H, J=8.21); 6.98(d, 2H, J=8.79); 6.51(d, 1H, J=8.21); 6.33(m, 2H); 6.00(s, 1H); 3.26(q, 2H, J=7.03); 3.08(t, 2H, J=7.62); 2.46(s, 6H); 1.43(m, 2H); 0.99(t, 3H, J=7.03); 0.74(t, 3H, J=7.03) | 580 |
| 20. | ¹H NMR(DMSO)<br>10.48(s, 2H); 9.15(s, 2H); 7.77(dd, 2H, J=1.76, 8.21 Hz); 7.54(d, 2H, J=1.76 Hz); 7.08(t, 1H, J=7.62 Hz); 6.98(d, J=8.21 Hz); 6.52(d, 1H, J=8.21 Hz); 6.39(s, 1H); 6.31 (d, 1H, J=7.62 Hz); 5.99(s, 1H); 3.23(m, 4H); 2.46(s, 6H); 0.99(t, 6H, J=7.03 Hz) | 564 |
| 21. | ¹H NMR(DMSO);<br>10.48(s, 2H); 9.15(s, 2H); 7.80(dd, J=2.34, 8.21 Hz, 1H); 7.55(d, J=1.76 Hz, 2H); 7.10(t, J=8.21,7.62 Hz, 1H); 7.00 (d, J=8.21 Hz, 2H); 6.51(dd, J=2.34, 8.21 Hz, 1H); 6.35(d, J=7.62 Hz, 2H); 6.01(s, 1H); 3.26(m, 2H); 3.12(t, J=7.62 7.62 Hz, 2H); 2.45(s, 6H); 1.39(m, 2H); 1.20(m, 2H); 1.02(t, J=7.03, 7.03 Hz, 3H); 0.762(t, J=7.62, 7.03 Hz, 3H) | 592 |
| 22. | ¹H NMR(300 MHz, DMSO)<br>10.46(s, 2H); 9.12(s, 2H); 7.77(dd, 2H, J=8.21, 1.76); 7.48(s, 2H); 7.04(m, 1H); 6.97(d, 2H, J=8.79); 6.42(m, 1H); 6.32(m, 2H); 5.95(s, 1H); 2.60(s, 3H); 2.44(s, 6H) | 522 |
| 23. | ¹H -NMR(300 MHz, DMSO)<br>10.66(brs, 2H); 9.17(s, 2H); 7.85(dd, 2H, J=8.21, 2.34); 7.68(d, 1H, J=7.62); 7.56(t, 1H, J=7.62); 7.46(d, 2H, J=2.34); 7.40(m, 2H); 7.04(d, 2H, J=8.21); 6.14(s, 1H); 3.08(q, 4H, J=7.03) 2.46(s, 6H); 0.92(t, 6H, J=7.03)<br>¹³C NMR(75 MHz, DMSO)<br>160.55, 159.47, 149.91, 144.67, 140.65, 133.79, 131.64, 130.94, 130.40, 130.12, 127.34, 125.28, 123.01, 116.66, 43.69, 42.04, 14.22, 8.76 | 629 |
| 24. | ¹H NMR(300 MHz, DMSO)<br>9.14(s, 2H); 7.78(dd, J=8.2, 2.0Hz, 2H); 7.47(s, 2H); 7.22(t, J=7.8 Hz, 1H); 6.97(d, J=8.8 Hz, 1H); 6.81(dd, J=8.2, 2.4 Hz, 1H); 6.67(d, J=7.6 Hz, 1H); 6.58(s, 1H); 6.02(s, 1H); 3.97(t, J=5.4 Hz, 2H); 2.62(t, J=5.4 Hz, 2H); 2.45(s, 6H); 2.19(s, 6H) | 582<br>(M + H) |
| 25. | ¹H NMR(300 MHz, DMSO)<br>10.54(s, 2H); 9.16(s, 2H); 9.12(s, 1H); 7.81(dd, 2H, J=8.79, 2.34); 7.58(d, 1H, J=9.37); 7.49(d, 2H, J=2.34); 7.47(s, 1H); 7.22(t, 1H, J=7.62); 7.00(d, 2H, J=8.79); 6.73(d, 1H, J=7.62); 6.04(s, 1H); 2.46(s, 6H); 1.18(s, 9H)<br>¹³C NMR(75 MHz, DMSO)<br>176.99, 160.47, 159.47, 149.81, 143.39, 140.12, 131.65, 131.20, 130.58, 128.75, 124.25, 122.75, 121.48, 118.85, 116.44, 43.46, 39.73, 27.79, 8.69 | (M − H)− =<br>592 |
| 26. | ¹H NMR(300 MHz, DMSO)<br>10.57(brs, 2H); 9.66(s, 1H); 9.16(s, 2H); 7.82(d, 2H, J=8.21); 7.44(s, 2H); 7.27(t, 1H, J=7.62); 7.10(d, 1H, J=7.62); 7.01(d, 2H, J=8.21); 6.97(s, 1H); 6.80(d, 1H, J=8.21); 6.03(s, 1H); 2.96(t, 2H, J=7.03); 2.46(s, 6H); 1.54(m, 2H); 1.20(m, 2H); 0.68(t, 3H, J=7.03) | (M − H)− =<br>628 |
| 27. | ¹H NMR(300 MHz, DMSO)<br>10.68(s, 2H); 9.20(s, 2H); 8.14(dt, J=2.3, 7.0 Hz, 1H); 7.89(d, J=1.8 Hz, 1H); 7.86(bs, 2H); 7.65(t, J=7.6 Hz, 1H); 7.63(s, 1H); 7.49(d, J=1.8 Hz, 2H); 7.04(d, J=8.2 Hz, 2H); 6.19(s, 1H); 2.48(s, 6H)<br>¹³C NMR(75 MHz, DMSO, 39.5 ppm);<br>159.73, 158.71, 149.23, 147.87, 144.72, 135.86, 131.54, 129.85, 129.74, 129.25, 122.93, 122.41, 121.45, 116.08, 42.87, 8.04 | 539 |
| 28. | ¹H NMR(DMSO)<br>10.56(s, 2H); 9.17(s, 2H); 7.81(d, 2H, J=8.2 Hz); 7.48(d, 2H, J=1.76 Hz); 7.29(t, 1H, J=7.62 Hz); 7.15(d, 1H, J=7.03 Hz); 7.00(d, 2H, J=8.21 Hz); 6.97(s, 1H); 6.89(d, 1H, J=7.62 Hz); 6.05(s, 1H); 2.47(s, 6H); 2.41(s, 3H) | (M − H)−<br>538.8 |
| 29. | ¹H NMR(DMSO)<br>10.65(s, 2H); 9.19(s, 2H); 7.84(d, 2H, J=8.19 Hz); 7.49 (m, 5H); 7.28(m, 1H); 7.02(d, 2H, J=8.43 Hz); 6.16(s, 1H); 2.72(s, 3H); 2.47(s, bb) | (M + H)+<br>557.1 |
| 30. | ¹H NMR(DMSO);<br>10.66(s, 2H); 9.19(s, 2H); 7.85(m, 3H); 7.62(m, 2H); 7.48(m, 3H); 7.03(d, 2H, J=8.21 Hz); 6.18(s, 1H); 3.20 (s, 3H); 2.47(s, 6H) | (M + H)+<br>573.1 |

TABLE 1-continued

| | | |
|---|---|---|
| 31. | ¹H NMR(300 MHz, DMSO)<br>10.66(s, 2H); 9.18(s, 2H); 7.85(dd, 2H, J=8.21, 1.76); 7.63(m, 2H); 7.47(d, 2H, J=1.76); 7.44(m, 1H); 7.37(s, 1H); 7.04(d, 2H, J=8.21); 6.15(s, 1H); 2.52(s, 6H); 2.46 (s, 6H)<br>¹³C NMR(75 MHz, DMSO)<br>160.56, 159.49, 149.90, 144.65, 135.05, 134.33, 131.56, 131.06, 130.37, 130.12, 128.15, 126.11, 123.05, 116.64, 43.81, 38.19, 8.77 | 602 |
| 32. | ¹H-NMR(300 MHz, DMSO)<br>10.47(s, 2H); 9.14(s, 2H); 7.78(dd, 2H, J=8.21, 1.76); 7.50(d, 2H, J=1.76); 6.99(m, 3H); 6.41(d, 1H, J=8.21); 6.34(s, 1H); 6.26(d, 1H, J=8.21); 5.95(s, 1H); 5.57(m, 1H); 2.89(t, 2H, J=7.03); 2.46(s, 6H); 1.50(m, 2H); 0.87 (t, 3H, J=7.03)<br>¹³C-NMR(75MHz, DMSO)<br>160.53, 159.61, 149.79, 149.66, 143.35, 131.76, 131.61, 130.45, 129.37, 122.65, 117.24, 116.35, 114.19, 109.92, 45.42, 43.34, 22.53, 12.29, 8.70 | 552 |
| 33. | ¹H NMR(300 MHz, DMSO)<br>9.11(s, 2H); 7.75(dd, J=8.2, 2.0 Hz, 2H); 7.49(s, 2H); 7.22(t, J=8.2 Hz, 1H); 6.93(d, J=8.0 Hz, 2H); 6.78(d, J=8.2 Hz, 1H); 6.64(d, J=8.0 Hz, 1H); 6.57(s, 1H); 5.95(s 1H); 3.92(t, J=6.5 Hz, 2H); 2.44(m, 12H); 1.75(pentet, J=6.5 Hz, 2H); 0.85(t, J=7.0 Hz, 6H) | 624<br>(M + H) |
| 34. | ¹H NMR(300 MHz, DMSO)<br>10.66(brs, 2H); 9.88(s, 1H); 9.15(s, 2H); 7.80(d, 2H, J=7.62); 756(d, 1H, J=7.03); 7.48(s, 2H); 7.28(s, 1H); 7.22(t, 1H, J=7.62); 7.05(d, 2H, J=8.21); 6.75(d, 1H, J=7.62); 6.03(s, 1H); 2.46(s, 6H); 1.97(s, 3H) | (M − H)− = 550 |
| 35. | ¹H NMR(300 MHz, DMSO)<br>10.57(brs, 2H); 9.14(s, 2H); 7.80(dd, 2H, J=8.21, 1.76); 7.43(s, 2H); 7.39(t, 1H, J=7.62); 7.16(m, 1H); 7.04(d, 1H, J=7.62); 7.00(d, 2H, J=8.79); 6.91(s, 1H); 6.07(s, 1H); 3.50(t, 2H, J=7.03); 2.43(s, 6H); 1.67(brs, 3H); 1.32(m, 2H); 0.70(t, 3H, J=7.03) | (M − H)− = 592 |
| 36. | ¹H NMR(300 MHz, DMSO)<br>10.57(brs, 2H); 9.13(s, 2H); 7.80(dd, 2H, J=8.21, 1.76); 7.00(d, 2H, J=8.79); 6.80(s, 1H); 6.08(s, 1H); 4.73(m, 1H); 2.42(s, 6H); 1.58(brs, 3H); 0.87(brs, 6H)<br>¹³C NMR(75 MHz, DMSO)<br>168.89, 160.62, 159.61, 149.84, 144.40, 139.49, 131.33, 131.26, 131.21, 131.10, 129.79, 129.48, 128.66, 122.87, 116.46, 45.50, 43.52, 23.89, 21.43, 8.74 | (M − H)−= 592 |
| 37. | ¹H NMR(300 MHz, DMSO)<br>10.6(s, 2H); 9.15(s, 2H); 7.83(d, 2H, J=8.79); 7.43(m, 3H); 7.14(d, 1H, J=8.21); 7.07(d, 1H, J=7.62); 7.02(d, 2H, J=8.21); 6.86(s, 1H); 6.10(s, 1H); 3.54(t, 2H, J=7.03); 2.46(s, 6H); 1.78(bm, 3H); 1.37(m, 2H); 0.74 (t, 3H, J=7.03); 0.59(d, 6H, J=5.86)<br>¹³ C NMR(75 MHz, DMSO)<br>171.30, 160.58, 159.57, 149.84, 144.70, 143.13, 131.67, 130.99, 130.74, 130.22, 129.94, 128.74, 126.57, 122.88, 116.57, 50.39, 43.33, 42.98, 25.85, 22.75, 21.23, 11.69, 8.74 | (M − H)− = 634 |
| 38. | ¹H-NMR(300 MHz, DMSO)<br>10.57(brs, 2H); 9.12(s, 2H); 7.79(d, 2H, J=8.79); 7.40(s, 3H); 7.10(m, 1H); 7.04(m, 1H); 7.00(d, 2H, J=8.79); 6.74(s, 1H); 6.08(s, 1H); 4.76(brm, 1H); 2.42(s, 6H); 1.81(brs, 1H); 1.63(brs, 2H); 0.90(brm, 6H); 0.56(brm, 6H) | (M − H)− = 634 |
| 39. | ¹H NMR(300 MHz, DMSO)<br>10.57(brs, 2H); 9.14(s, 2H); 7.80(dd, 2H, J=8.21, 1.76); 7.44(s, 2H); 7.39(t, 1H, J=7.62); 7.16(d, 1H, J=8.21); 7.02(m, 3H); 6.90(s, 1H); 6.08(s, 1H); 3.12(s, 3H); 2.44 (s, 6H); 1.80(brs, 3H); 0.58(brs, 6H)<br>¹³C NMR(75 MHz, DMSO)<br>171.59, 160.54, 159.31, 149.86, 144.72, 131.74, 130.99, 130.67, 130.20, 128.78, 128.55, 125.64, 122.89, 116.58, 43.35, 42.66, 37.47, 25.82, 22.79, 8.77 | M+ = 607 |
| 40. | ¹H NMR(300 MHz, DMSO)<br>10.57(brs, 2H); 9.14(s, 2H); 7.80(dd, 2H, J=8.21, 1.76); J=8.21); 7.06(d, 1H, J=8.21); 7.00(d, 2H, J=8.21); 6.90 (s, 1H); 6.08(s, 1H); 3.56(q, 2H, J=7.03); 2.43(s, 6H); 1.66(brs, 3H); 0.92(t, 3H, J=7.03)<br>¹³C NMR(75 MHz, DMSO)<br>169.03, 160.58, 159.60, 149.85, 144.70, 143.17, 131.45, 130.99, 130.19, 129.39, 128.98, 126.51, 122.89, 116.51, 43.51, 23.15, 13.59, 8.74 | (M + H)+ = 580 |

TABLE 1-continued

| | | |
|---|---|---|
| 41. | ¹H NMR(300 MHz, DMSO) 10.57(brs, 2H); 9.67(s, 1H); 9.16(s, 2H); 7.82(dd, 2H, J=8.21, 1.76); 7.44(d, 2H, J=1.76); 7.27(t, 1H, J=7.62); 7.10(d, 1H, J=8.21); 7.01(d, 2H, J=8.21); 6.97(s, 1H); 6.80(d, 1H, J=8.21); 6.03(s, 1H); 2.97(t, 2H, J=7.03); 2.47(s, 6H); 1.59(m, 2H); 0.81(t, 3H, J=7.03) | (M − H)− = 614 |
| 42. | ¹H NMR(DMSO): 10.48(s, 2H); 9.15(s, 2H); 7.80(d, J=7.33 Hz, 2H) 7.52(s, 2H); 7.13(t, J=8.2, 7.62 Hz, 1H); 7.00(d, J=8.79 Hz, 2H); 6.67(d, J=8.21 Hz, 1H) 6.54(s, 1H) 6.37(d, J=7.62 Hz, 1H); 6.01(s, 1H); 3.99(m, 1H); 2.60 (s, 3H); 2.46(s, 6H); 1.06(d, J=6.45 Hz, 6H) | 564 |

*¹H NMR and ¹³C NMR spectra were acquired on a Varian Mercury VX 300 Spectrometer and referenced to tetramethylsilane (TMS) unless indicated otherwise. Chemical shifts and coupling constants are reported in parts per million (ppm) and ¹Hertz (¹Hz) respectively.

Illustrative examples of the preparation of prodrugs in accordance with the present invention are provided below.

Example 31

Preparation of Prodrugs a. A solution of 2,2'-[(3-propylphenyl)methylene]bis[4-[[(5-methyl-1H-tetrazol-1-yl)imino]methyl]]phenol (200 mg, 0.37 mmol), prepared as described in Example 1, above, in anhydrous pyridine (1 ml) and propionic anhydride (0.234 ml) was warmed gently with a heat gun, and then kept at room temperature for 2 hours. The solvent was removed and water (5 ml) was added to the residue. The mixture was sonicated, and a solid was collected, washed with water, and then dried to give 225 mg of the desired dipropionate prodrug.

b. A solution of 2,2'-[(3-propylphenyl)methylene]bis[4-[[(5-methyl-1H-tetrazol-1-yl)imino]methyl]]phenol (200 mg, 0.37 mmol), prepared according to Example 1, above, in anhydrous pyridine (1 ml) and acetyl chloride (0.106 ml) was stirred at room temperature for 3 hours. The solvent was removed, and water was added to the residue. After sonication, a solid formed, which was filtered and dried to give 216 mg of the desired diacetate prodrug.

Scheme 1 illustrates an aspect of the invention regarding methods of preparing the compound of Formula III.

Scheme 1

Y, $R_a$, $R_b$, M, X″, $R_3$, and P are defined and selected in accordance with the description of the invention above.

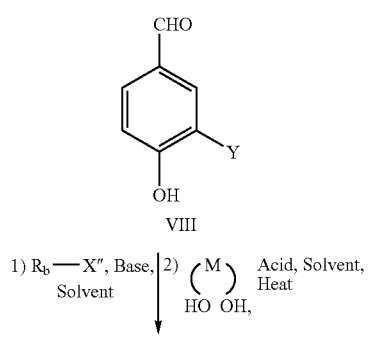

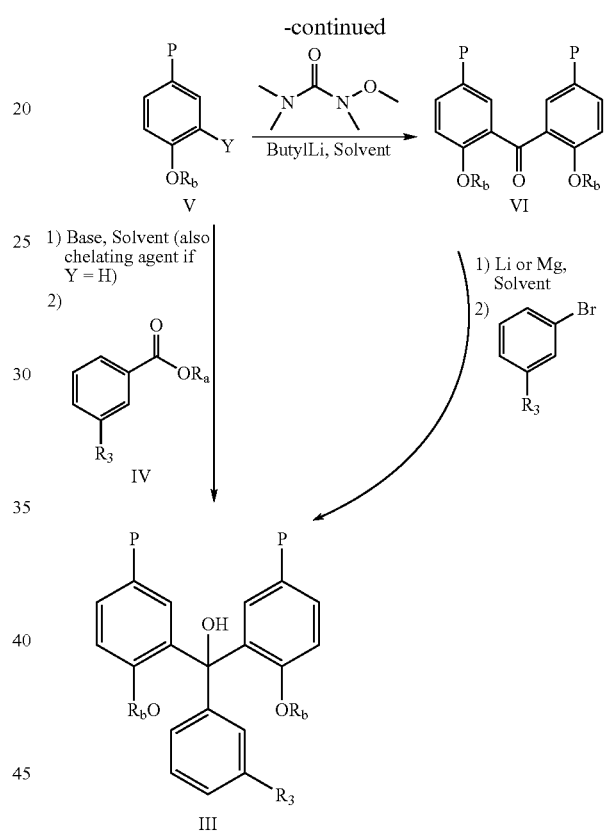

Example 32 illustrates the effectiveness of the compounds used in the method of the invention in inhibiting the viral replication of RSV in cell culture.

Example 32

Cell Culture Assay for Inhibition of Pneumovirus Replication

The replication of many viruses may be quantitatively assessed in the laboratory in various cell or tissue culture systems. Such in vitro culture methodologies are available and useable by those skilled in the art for the propagation and quantitative measurement of the replication of pneumoviruses. The following procedure was used for the in vitro quantitative measure of RSV replication.

Using the procedure described in this example, compounds of the present invention were evaluated for their ability to inhibit the replication of the virus in cell culture. By adding compounds at various concentrations to the culture medium, a dose response effect of the compound on virus replication was determined. A useful quantitative measure of the inhibition of RSV replication in this assay is the concentration of the compound at which virus replication in cell culture is inhibited by 50% in comparison to that observed in the absence of the compound (50% Inhibitory Concentration, $IC_{50}$). In the case of RSV, $IC_{50}$ values are defined as the concentration of compound that protected 50% of the cell monolayer from virus-induced cytopathic effect (syncytia formation).

Anti-pneumovirus compounds of the invention were screened for antiviral activity against RSV (strain Long) on cultured HEp2 cells. Standard 96-well culture plates were seeded with $4 \times 10^4$ HEp2 cells in 200 µL of Minimal Essential Medium with Earles salts (EMEM) supplemented with 10% fetal bovine serum (FBS). Twenty-four to 30 hours later, the cells were infected with a dilution of RSV in Medium 199 (GIBCO/BRL) with 5% FBS that had been titrated to yield >85% destruction of the cell monolayer in 60 hours. After 1 hour at 37° C., compounds were added to wells of the plate in a final DMSO concentration of 0.5% as a series of 10 two-fold dilutions of the compound.

Virus control wells (VC, no test compound) and cell culture control wells (CC, no virus, no test compound) were also included on each plate. Plates were incubated in a humidified atmosphere at 37° C. and 5% carbon dioxide. After 60 hours, 100 µL of a 5% solution of glutaraldehyde in water was added to each well, and the wells were incubated at room temperature for 1 hour. The fixative was removed, and the cells were stained with a 0.1% solution of crystal violet in water for 15-30 minutes. After rinsing and drying the plates, the optical density of the wells was measured at 570 nm ($OD_{570}$).

To determine $IC_{50}$ values for the test compounds, the mean value of the $OD_{570}$ readings of the virus control wells (VC) on a plate was subtracted from the $ODS_{70}$ readings of all wells on that plate. The $IC_{50}$ values were then calculated according to the following formula:

$$IC_{50} = [(Y-B)/(A-B)] \times (H-L) + L$$

where Y represents the mean $OD_{570}$ reading of the cell control wells (CC) divided by 2; B represents the mean $OD_{570}$ reading of wells of the compound dilution nearest to and below Y; A represents the mean $OD_{570}$ reading of wells of the compound dilution nearest to and above Y; L represents the compound concentration at B; and H represents the compound concentration at A.

A similar assay is useful for various strains of human RSV, including subtype A and subtype B viruses, as well as other pneumoviruses.

The $IC_{50}$ results of the cell culture assay for inhibition of the replication of several pneumoviruses for representative compounds used in the method of the invention range from 0.1 nM to 1 µM. The low concentrations of test compounds required to achieve 50% inhibition of RSV replication in cell culture indicate that the compounds used in the method of the invention are effective at inhibiting the pneumovirus replication process. It is also demonstrated here that the compounds of the invention are dramatically more potent than Ribavirin at inhibiting viral replication.

Example 33 demonstrates that the compounds of the invention are not toxic or detrimental to the health of normal cells at concentrations well above those needed to inhibit pneumovirus replication.

Example 33

Assay for Cytotoxicity of Inhibitors of Pneumovirus Replication

To demonstrate that the compounds of the invention are not toxic or detrimental to the health of normal cells, compounds of the invention were evaluated in an in vitro cytotoxicity assay. One useful assay for determining the cytotoxic effects of compounds on the growth of cells is a tetrazolium-based calorimetric method (Mossman, T., J. Immun. Methods, 65 (1-2): 55-63 (1983)). This assay measures cell viability, and therefore cytotoxicity, by quantitatively detecting the in situ reduction of 3-(4,5-dimethylthiazol-2-yl)-2,5-diphenyltetrazolium bromide (MTT) by viable cells. Cells are seeded in 96-well plates in DMEM containing 5% PBS at a density of $4 \times 10^3$ cells per well. After incubation for 4 hours at 37° C. and 5% $CO_2$, 2-fold dilutions of compound in 1% DMSO (or solvent alone) are added to quadruplicate wells, and the plates are incubated for an additional 68 hours at 37° C. and 5% $CO_2$, which is equivalent to 3 to 4 cell doublings. The culture medium is removed, and the cells are treated with 1 mg/ml of MTT in phosphate-buffered saline, pH 7.2 for 4 hours at 37° C. and 5% $CO_2$. After removal of the unreduced MTT, the reduced blue formazan crystals produced by the viable cells are solubilized by the addition of 0.04N HCl in isopropanol. The optical density at 570 nm ($OD_{570}$) of each well is read using a suitable microplate reader. Cell viability is expressed as the percentage of optical density for compound-treated cells relative to the optical density of solvent alone-treated control wells. The highest compound concentration resulting in an optical density of $\geq 75\%$ of the control is represented as the cellular cytotoxicity value ($CC_{75}$).

The results of the MTT cytotoxicity assay using compounds prepared, range from 3 to >50 (µM).

The cellular cytotoxicity ($CC_{75}$) values for the representative compounds are considerably higher than the antiviral ($IC_{50}$) values for these compounds. These results indicate that the compounds of the invention are highly selective and, at therapeutically effective doses, they do not detrimentally affect the health of normal cells. A measure of this selectivity is provided by the high selective index value (SI), which is defined as $CC_{75}/IC_{50}$. The high SI values exhibited by compounds of the invention indicate very desirable attributes of the compounds.

Example 34

To demonstrate that the compounds of the invention have improved solubility characteristics, Table 2 lists solubility measurements of representative compounds of the invention as compared to their para-substituted isomers. The solubilities are measured in ethanol/propylene glycol/water (85:10:5) (proportions are by volume).

TABLE 2

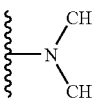

| Example Number | $R_1$ | Meta Position Solubiity (mg/ml) | Para Position Solubility (mg/ml) |
|---|---|---|---|
| 1 | $—CH_2CH_2CH_3$ | 1.9 | 0.18 |
| 2 | 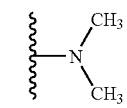  | 2.10 | 0.09 |
| 6 | $—OCH_2CH_3$ | 1.85 | 0.30 |
| 16 | $—CH_2CH_2OCH_3$ | 1.14 | 0.29 |
| 20 | 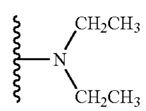  | 1.45 | 0.21 |
| 27 | $—NO_2$ | 0.98 | 0.16 |
| 31 | 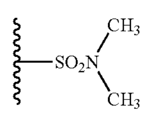  | 0.08 | 0.03 |

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A pharmaceutical composition for treating pneumovirus infection comprising a compound, selected from the group consisting of:
2,2'-[(3-Propylphenyl)methylene]bis[4-[[(5-methyl-1H-tetrazol-1-yl) imino]methyl]]phenol;
2,2'-[[(3-Dimethylamino)phenyl]methylene]bis[4-[[(5-methyl-1H-tetrazol-1-yl) imino]methyl]]phenol;
2,2'-[(3-Ethoxyphenyl)methylene]bis[4-[[(5-methyl-1H-tetrazol-1-yl)imino]methyl]]phenol;
2,2'-[[(3-Methoxyethyl)phenyl]methylene]bis[4-[[(5-methyl-1H-tetrazol-1-yl) imino]methyl]]phenol;
2,2'-[[(3-Diethylamino)phenyl]methylene]bis[4-[[(5-methyl-1H-tetrazol-1-yl) imino]methyl)]phenol;
2,2'-[(3-Nitrophenyl)methylene]bis[4-[[(5-methyl-1H-tetrazol-1-yl)imino]methyl]]phenol;

3-[[Bis[[5-(5-methyl-1H-tetrazol-1-yl)imino]methyl]-2-hydroxyphenyl]methylene]-N,N-dimethylbenzene-sulfonamide; and pharmaceutically acceptable salts of said compound in an amount effective to attenuate infectivity of said virus, and a pharmaceutically effective carrier medium, wherein said carrier medium comprises about 85% ethanol, about 10% propylene glycol and about 5% water.

2. The pharmaceutical composition according to claim 1, wherein the compound is 2,2'-[(3-Propylphenyl)methylene]bis[4-[[(5-methyl-1H-tetrazol-1-yl)imino]methyl]]phenol.

3. The pharmaceutical composition according to claim 1, wherein the compound is 2,2'-[[(3-Dimethylamino)phenyl]methylene]bis[4-[[(5-methyl-1H-tetrazol-1-yl)imino]methyl]]phenol.

4. The pharmaceutical composition according to claim 1, wherein the compound is 2,2'-[[(3-Methoxyethyl)phenyl]methylene]bis[4-[[(5-methyl-1H-tetrazol-1-yl)imino]methyl]]phenol.

5. The pharmaceutical composition according to claim 1, wherein the compound is 2,2'-[[(3-Diethylamino)phenyl]methylene]bis[4-[[(5-methyl-1H-tetrazol-1-yl)imino]methyl]]phenol.

6. The pharmaceutical composition according to claim 1, further comprising at least one supplemental active agent selected from the group consisting of interferon, ribavirin an immunomodulator, an immunoglobulin, an anti-inflammatory agent, an antibiotic, an anti-viral and an anti-infective.

7. The pharmaceutical composition according to claim 1, wherein said pharmaceutical composition comprises less than 5% water.

8. A method of treatment of pneumovirus infection in a patient in need of said treatment, said method comprising administering to said patient a therapeutically effective amount of a compound according to claim 1.

9. A method according to claim 8, wherein said compound is administered through inhalation.

10. A method according to claim 8, wherein said compound is administered by an electrostatic delivery device.

11. A method according to claim 10, wherein said electrostatic delivery device is hand-held.

12. A method as according to claim 10, wherein said electrostatic delivery device is disposable.

13. A method according to claim 10, wherein said electrostatic delivery device is for a single user.

14. A method according to claim 10, wherein said electrostatic delivery device comprises a removable mouthpiece.

15. A method according to claim 10, wherein said electrostatic delivery device comprises a mask.

* * * * *